(12) United States Patent
Landa et al.

(10) Patent No.: US 11,266,578 B2
(45) Date of Patent: Mar. 8, 2022

(54) COMPOSITION, KIT AND METHOD FOR COLORING KERATINOUS FIBERS

(71) Applicant: Henkel AG & Co. KGaA, Duesseldorf (DE)

(72) Inventors: Benzion Landa, Nes Ziona (IL); Sagi Abramovich, Ra'anana (IL); Tamar Asher, Tel Aviv (IL); Meir Soria, Jerusalem (IL); Yishai Karton, Nes Ziona (IL)

(73) Assignee: HENKEL AG & CO. KGAA, Duesseldorf (DE)

( * ) Notice: Subject to any disclaimer, the term of this patent is extended or adjusted under 35 U.S.C. 154(b) by 221 days.

(21) Appl. No.: 16/476,940

(22) PCT Filed: Jan. 11, 2018

(86) PCT No.: PCT/IB2018/000146
§ 371 (c)(1),
(2) Date: Jul. 10, 2019

(87) PCT Pub. No.: WO2018/130912
PCT Pub. Date: Jul. 19, 2018

(65) Prior Publication Data
US 2019/0350823 A1   Nov. 21, 2019

(30) Foreign Application Priority Data

Jan. 11, 2017 (GB) ..................................... 1700510
Dec. 5, 2017 (GB) ..................................... 1720256

(51) Int. Cl.
| | | |
|---|---|---|
| A61Q 5/00 | (2006.01) |
| A61K 8/06 | (2006.01) |
| A61K 8/25 | (2006.01) |
| A61K 8/892 | (2006.01) |
| A61K 8/898 | (2006.01) |
| A61Q 5/10 | (2006.01) |

(52) U.S. Cl.
CPC ................ *A61K 8/062* (2013.01); *A61K 8/25* (2013.01); *A61K 8/892* (2013.01); *A61K 8/898* (2013.01); *A61Q 5/10* (2013.01); *A61K 2800/43* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| | | |
|---|---|---|
| 2009/0183320 A1 | 7/2009 | Benabdillah |
| 2010/0247785 A1* | 9/2010 | Martz .................. C09D 183/04 427/387 |
| 2012/0145177 A1 | 6/2012 | Thompson et al. |
| 2013/0149358 A1 | 6/2013 | Colaco et al. |
| 2014/0308229 A1 | 10/2014 | Bouzeloc et al. |
| 2014/0356309 A1 | 12/2014 | Ozaki et al. |
| 2016/0235658 A1 | 8/2016 | Herrlein et al. |
| 2016/0310378 A1 | 10/2016 | Herrlein et al. |

FOREIGN PATENT DOCUMENTS

| | | |
|---|---|---|
| EP | 2415797 A1 | 2/2012 |
| EP | 3058934 A1 | 8/2016 |
| WO | 2011128255 A1 | 10/2011 |
| WO | 2016133806 A1 | 8/2016 |

OTHER PUBLICATIONS

EPO, International Search Report issued in International Application No. PCT/IB2018/000146, dated May 18, 2018.

* cited by examiner

*Primary Examiner* — Jyothsna A Venkat
(74) *Attorney, Agent, or Firm* — Lorenz & Kopf, LLP

(57) ABSTRACT

There is disclosed a method of coating mammalian hair, the method comprising applying, on the external surface of individual hairs of the mammalian hair, an oil-in-water emulsion comprising: (i) an aqueous phase containing water; and (ii) an oil phase containing at least one water-insoluble reactive condensation-curable film-forming amino-silicone pre-polymer that, subsequent to condensation curing, forms an elastomer. The reactive oil phase may further contain a plurality of sub-micronic pigment particles dispersed therein. Suitable compositions and kits including the same are also disclosed, as well as methods for preparing the compositions.

12 Claims, 4 Drawing Sheets

COMPOSITION, KIT AND METHOD FOR COLORING KERATINOUS FIBERS

CROSS-REFERENCE TO RELATED APPLICATION

This application is a U.S. National-Stage entry under 35 U.S.C. § 371 based on International Application No. PCT/IB2018/000146, filed Jan. 11, 2018, which was published under PCT Article 21(2), which claims priority to Great Britain Application No. 1720256.5, filed Dec. 5, 2017 and which claims priority to Great Britain Application No. 1700510.9, filed Jan. 11, 2017 which are all hereby incorporated in their entirety by reference.

TECHNICAL FIELD

The present disclosure relates to compositions and kits for coloring keratinous fibers, such as hair. Methods for preparing and using the same are also disclosed.

BACKGROUND

Natural hair color is the pigmentation of hair follicles due to two types of melanin: eumelanin and pheomelanin. Generally, if more eumelanin is present, the color of the hair is darker; if less eumelanin is present, the hair shade is lighter. Levels of melanin can vary over time causing hair color to change.

Melanin production decreases in the hair roots of humans with ageing, causing lightening of the hair, and finally ceases. Once melanin production ceases, new hairs grow out gray or white when light reflects through them.

Hair coloring is the practice of changing the color of hair. The main reasons for this practice are cosmetic (e.g., to cover gray hair, to change to a color regarded as more fashionable or desirable, or to restore the original hair color after it has been discolored, for instance by hairdressing processes or sun bleaching). Hair coloring is achieved by use of coloring compositions comprising chemical, organic, herbal or natural coloring agents. The coloring agents generally fall into two categories, a) soluble dyes that may penetrate the hair (but can also remain external) and may be reacted to induce the desired coloring effect, and b) water-insoluble pigments, which in view of their dimensions are typically restricted to external coloring of hair fibers.

Based on how long the effect lasts, coloring may be permanent, demi-permanent, semi-permanent or temporary.

Permanent hair coloring typically involves penetration of direct dye or oxidation dye precursor deep into the hair shaft, generally preceded by the removal of any existing melanin, requiring bleaching, and sealing of the coloring agent into the hair cortex. Permanent coloring further requires an oxidizing agent or coupler in order for the color to fully develop. The color does not wash out with shampoo for at least about 30 shampoo washes. However, such permanent coloration may severely damage the hair.

Demi-permanent hair coloring compositions are also known as deposit-only hair colors. These are chemically milder than permanent hair coloring compositions, penetrate only partially into the hair shaft, and typically do not remove the hair's natural pigment. Demi-permanent hair color washes out after about 10-30 shampoo washes.

Semi-permanent hair coloring compositions are chemically milder than either permanent or demi-permanent coloring compositions, involving only a small extent of penetration into the hair shaft. Semi-permanent coloring compositions remain on the hair for only 4-10 shampoo washes.

Permanent, demi-permanent or semi-permanent coloring processes are known to damage keratin fibers. Moreover, certain processes raise health concerns, some compositions being possibly carcinogenic.

Temporary hair coloring compositions do not penetrate into the hair shaft, but remain on the outer surface of the hair shaft. Such coloring compositions may easily be washed out by a single shampoo, resisting at most 2-3 shampoos under favorable circumstances.

There remains a need for coloring compositions for coloring keratin fibers, such as hair, which exhibit reduced penetration and impact on the integrity of the fibers being colored as compared to known coloring compositions, while providing long-lasting coloration of the fibers.

There further remains a need for coloring compositions for dark-colored keratin fibers, wherein such coloring compositions provide a lighter color than that of the native keratin fiber, wherein such coloring compositions are used without the need for bleaching of the keratin fiber.

In addition, other objects, desirable features and characteristics will become apparent from the subsequent summary and detailed description, and the appended claims, taken in conjunction with the accompanying drawings and this background.

BRIEF SUMMARY

The present disclosure relates to compositions for coloring keratinous fibers, such as human hair, and more particularly to compositions comprising a reactive, condensation-curable amino functional silicone pre-polymer and a pigment, in an aqueous medium.

Pre-polymers generally refer to materials (e.g., uncured/curable monomers, oligomers and/or polymers) that can be cross-linked to form larger macro molecules through cross-linkable groups, also termed reactive groups, by techniques known as curing processes. As used herein, the pre-polymers are deemed reactive (being still able to participate in polymerization or curing) when they lack a glass transition (Tg) temperature. A variety of curing processes exist depending on the chemical composition of the pre-polymers to be cross-linked, their reactive groups and the curing auxiliary factors (cross-linkers, curing accelerators or catalysts, and the like). The present disclosure is concerned with silicone pre-polymers being condensation-curable, namely bearing cross-linkable groups able to react with one another so as to form by condensation a siloxane bond, while liberating in the process a molecule of alcohol, oxime or water. Condensation-curable amino functional silicones are further characterized by the presence of amino groups attached via carbon atoms to the backbone of the silicone pre-polymers. These amino groups or side chains are further capable of attaching to or interacting with other molecules through nucleophilic reactions or interactions (for example, but not limited, on carboxylic, anhydride or epoxy functional molecules or substrates). Therefore, while some of the silicone pre-polymers disclosed herein are termed "reactive" or "condensation-curable" amino functional silicones, this terminology is not intended to be limiting the curing process exclusively through condensation of the reactive groups, the amino groups being capable of curing also through "non-condensation" processes, such as resulting in the formation of nitrogen-carbon bonding. The products of such curing processes are networks of cross-linked oligomers or polymers termed elastomers or elastomeric networks (rubber like), in reference to their viscoelastic properties. As such cured networks (preferably three-dimensional to enhance cohesivity) may form a continuous film, the pre-polymers participating in such formation, alone or in combination with additional film-forming agents, can also be termed film-forming pre-polymers.

Such amino functional silicones (alternatively referred to as amino-silicones or amine-silicones), may be considered as positively charged or positively chargeable under suitable chemical environment (e.g., relatively low pH above the isoelectric point of the hair). Such materials can in part be characterized by their Amine Number. In some embodiments, the condensation-curable amino-silicone pre-polymer is insoluble or substantially insoluble in water, in which case the pre-polymer can also be said to be hydrophobic. In some embodiments, the solubility of the pre-polymer is of about 5 wt. % or less, about 2 wt. % or less, about 1 wt. % or less, about 0.5 wt. % or less, or about 0.1 wt. % or less, with respect to the weight of the aqueous composition wherein it is disposed. Solubility can be assessed by the naked eye, the composition being typically at about 23° C. A material is water-soluble at or below a threshold concentration, if forming a clear solution in water. When the material is a large macromolecule, such as a polymer, the polymer is said to be water soluble if the micelles formed therefrom are undetectable, the water carrier remaining clear. Conversely, the material (or the polymer) is insoluble if not water-soluble (e.g., forming a visually detectable dispersion or emulsion). Typically, the condensation-curable amino-silicone reactants form a phase separate from water, being substantially non-miscible therewith. Such a distinct phase may also be referred to as an "oil phase", a reactive oil phase or the like.

In one aspect, there is provided a method of coating mammalian hair, the method comprising:
(a) applying, on an external surface of individual hairs of the mammalian hair, an oil-in-water emulsion comprising:
(A) an aqueous phase containing water; and
(B) an oil phase containing at least one reactive condensation-curable film-forming amino-silicone pre-polymer that, subsequent to condensation curing, forms an elastomer;
wherein said oil phase fulfills at least one of the following:
(i) said at least one reactive condensation-curable film-forming amino-silicone pre-polymer includes at least one reactive condensation-curable film-forming amino-silicone monomer having a molecular weight of at most about 1000 g/mole;
(ii) said oil phase further contains a non-amino cross-linking agent adapted or selected to cure said pre-polymer, said non-amino cross-linking agent having a molecular weight in the range of at most about 1000 g/mole;
(b) after partial condensation curing of said pre-polymer has occurred so as to form an at least partially cured film on the external surface of the individual hairs, washing the hair with a rinsing liquid to remove any excess of said oil-in-water emulsion.

In some embodiments, a first amino-silicone pre-polymer of the at least one reactive condensation-curable film-forming amino-silicone pre-polymer has at least 3 silanol and/or hydrolysable groups, so as to form a 3-dimensional network.

In some embodiments, a first concentration of the first amino-silicone pre-polymer, within the oil phase, is at least about 15%, at least about 20%, at least about 30%, at least about 40%, at least about 50%, or at least about 60%, by weight, of said oil phase. In some embodiments, the first concentration is at most about 95%, at most about 90%, at most about 85%, at most about 80%, at most about 75%, or at most about 70%. In some embodiments, the first concentration of the first amino-silicone pre-polymer, within the oil phase, is within a range of from about 20-95%, from about 20-85%, from about 30-95%, from about 30-85%, from about 40-95%, from about 40-85%, from about 40-75%, from about 45-95%, from about 45-85%, from about 50-95%, from about 50-85%, from about 55-95%, from about 55-85%, from about 55-75%, from about 60-95%, from about 60-90%, from about 60-85%, or from about 60-80%.

In some embodiments, a combined concentration of the first amino-silicone pre-polymer and the non-amino cross-linking agent, within the oil phase, is within a range of from about 35-95%, from about 40-95%, from about 40-85%, from about 40-75%, from about 45-95%, from about 45-85%, from about 50-95%, from about 50-85%, from about 55-95%, from about 55-85%, from about 55-75%, from about 60-95%, from about 60-90%, from about 60-85%, or from about 60-80%, by weight, of said oil phase.

In some embodiments, a concentration of the non-amino cross-linking agent within the combined concentration is limited by a condition that the oil-in-water emulsion has a surface zeta potential greater than zero (>0), or at least +1 mV, at least +2 mV, at least +3 mV, at least +5 mV, at least +7 mV, or at least +10 mV.

In some embodiments, within the oil phase, a total concentration of the amino-silicone oil, the non-amino-silicone oil and the at least one reactive condensation-curable film-forming amino-silicone pre-polymer, excluding the first amino-silicone pre-polymer, is within a range of from about 3% to about 65%, from about 3% to about 60%, from about 3% to about 55%, from about 3% to about 50%, from about 3% to about 45%, from about 3% to about 40%, from about 7% to about 40%, from about 10% to about 40%, from about 10% to about 50%, from about 15% to about 50%, from about 15% to about 45%, from about 15% to about 40%, from about 20% to about 45%, from about 25% to about 45%, from about 25% to about 50%, from about 30% to about 45%, from about 30% to about 60%, from about 35% to about 50%, or from about 35% to about 60%, by weight. In some embodiments, the total concentration of the aforesaid different constituents of the oil phase is subject to the oil phase having a viscosity of no more than about 500 mPa·s, as measured at about 25° C.

In some embodiments, the concentration of a terminating pre-polymer having a single silanol or hydrolysable group, within the oil phase, is at most about 7%, at most about 5%, at most about 2%, by weight of the oil phase. In some embodiments, the oil phase is devoid of said terminating pre-polymer.

In some embodiments, the total concentration of organic solvents within the oil phase of the emulsion, on a weight basis, is at most about 10%, at most about 5%, at most about 2%, or at most about 1%. In some embodiments, the oil phase is devoid of any organic solvent.

In some embodiments, the total concentration of water-miscible co-solvents within the aqueous phase of the emulsion, on a weight basis, is at most about 10%, at most about 5%, at most about 2%, or at most about 1%. In some embodiments, the aqueous phase is devoid of any said co-solvent.

In some embodiments, the oil-in-water emulsion further comprises a solid, hydrophobic reactive inorganic filler, said filler disposed or dispersed within the oil phase, said filler selected or adapted to facilitate curing of the condensation-curable film-forming amino-silicone pre-polymer(s).

In some embodiments, the reactive filler includes, mainly includes, or includes, a hydrophobic fumed silica.

In some embodiments, the average particle size ($D_v50$) of the solid, hydrophobic reactive inorganic filler is within a range of from about 5 to about 500 nm, from about 5 to about 250 nm, from about 10 to about 200 nm, from about 20 to about 200 nm, from about 40 to about 300 nm, from about 60 to about 300 nm, from about 60 to about 250 nm, or from about 60 to about 200 nm.

In some embodiments, the concentration of the solid, hydrophobic reactive inorganic filler disposed or dispersed within the oil phase is within a range of from about 0.2% to about 12%, from about 0.2 to about 10%, from about 0.2 to about 8%, from about 0.4 to about 10%, from about 0.4 to about 8%, from about 0.6 to about 10%, from about 0.6 to about 8%, from about 0.8 to about 8%, or from about 0.8 to about 6%, by weight.

In some embodiments, the concentration of the solid, hydrophobic reactive inorganic filler within the oil-in-water emulsion is within a range of from about 0.005% to about 0.5%, from about 0.005% to about 0.3%, by weight.

In some embodiments, the refractive index of the solid, hydrophobic reactive inorganic filler is within a range of ±10%, ±7%, ±5%, or ±3%, of a refractive index of the oil phase, exclusive of any pigment particles disposed therein.

In some embodiments, the at least partially cured film is self-terminated on the external surface of the individual hairs.

In some embodiments, the at least one reactive condensation-curable film-forming amino-silicone pre-polymer has a solubility in water of less than about 1% by weight at about 25° C.

In some embodiments, the at least one reactive condensation-curable film-forming amino-silicone pre-polymer includes a reactive condensation-curable amino-silicone monomer having a solubility in water of less than about 1% by weight at 25° C.

In some embodiments, the partial condensation curing is effected or transpires at a temperature of at most about 38° C., at most about 36° C., at most about 34° C., or at most about 32° C., and optionally, at least about 15° C.

In some embodiments, the washing of the hairs is performed within about 30 minutes, within about 20 minutes, within about 15 minutes, within about 10 minutes, within about 5 minutes, within about 3 minutes, within about 2 minutes, or within about 1 minute, after the application of the oil-in-water emulsion has been completed.

In some embodiments, following the washing, further curing transpires solely by or substantially solely by humidity or ambient humidity.

In some embodiments, within at least two days, at least three days, at least five days, or at least a week of said washing, all further curing proceeds in the absence of any non-cationic surfactant added to the hair.

In some embodiments, within at least two days, at least three days, at least five days, or at least a week of the washing, treating the hair can be performed with a hair formulation containing a cationic surfactant.

In some embodiments, the said oil-in-water emulsion has a surface zeta potential greater than zero, or at least about +1 mV, at least about +2 mV, at least about +3 mV, at least about +5 mV, at least about +7 mV, at least about +10 mV, at least about +15 mV, at least about +20 mV, at least about +30 mV, at least about +40 mV, or at least about +60 mV; optionally, at most about +100 mV, or at most about +80 mV.

In some embodiments, the oil-in-water emulsion has a surface zeta potential greater than zero and below about 90 mV, or within a range of from about 1-50 mV, from about 1-30 mV, from about 1-20 mV, from about 1-15 mV, from about 2-100 mV, from about 2-30 mV, from about 3-100 mV, from about 3-50 mV, from about 3-30 mV, from about 3-20 mV, from about 5-100 mV, from about 5-50 mV, from about 5-30 mV, from about 5-20 mV, from about 7-100 mV, from about 10-80 mV, from about 15-80 mV, from about 20-80 mV, or from about 20-60 mV.

In some embodiments, the surface zeta potential of the oil-in-water emulsion is measured at a pH of about 10. In other embodiments, the surface zeta potential is measured at a native pH of said oil-in-water emulsion.

In some embodiments, the rinsing liquid is (i) water, or (ii) a cationic rinsing liquid containing a cationic surfactant, or (iii) a rinsing liquid devoid of non-cationic surfactants, degreasing agents and/or swelling agents, the degreasing and swelling agent respectively able to degrease and swell the at least partially cured film.

In some embodiments, the cationic surfactant is a cosmetically-acceptable primary, secondary, tertiary, or quaternary ammonium compound or polymer.

In some embodiments, the total concentration of reactive condensation-curable amino-silicone components within the oil phase is at least about 45%, at least about 55%, at least about 60%, or at least about 65%, by weight, on a pigment-less basis. In some embodiments, the total concentration of reactive components within a range of from about 50-100%, from about 50-95%, from about 50-90%, from about 50-85%, from about 50-80%, from about 55-95%, from about 55-85%, from about 60-95%, from about 60-85%, from about 65-95%, from about 65-90%, or from about 70-95%.

In some embodiments, the amino-silicone pre-polymer includes reactive groups selected from the group consisting of alkoxy-silane reactive groups, silanol reactive groups and combinations thereof.

In some embodiments, the oil phase, exclusive of all inorganic content, has no glass transition temperature.

In some embodiments, the at least one reactive condensation-curable film-forming amino-silicone pre-polymer is a liquid at about 25° C.

In some embodiments, the viscosity of the at least one reactive condensation-curable film-forming amino-silicone pre-polymer, measured in a suitable rheometer at about 25° C., is in a range of from about 2-1000 milliPascal-second (mPa·s), from about 2-500 mPa·s, 2-300 mPa·s, from about 2-200 mPa·s, from about 5-1000 mPa·s, from about 5-500 mPa·s, from about 5-300 mPa·s, from about 7-500 mPa·s, from about 7-300 mPa·s, or from about 7-200 mPa·s.

In some embodiments, the at least one of, and optionally all of the at least one reactive condensation-curable film-forming amino-silicone pre-polymers, has an Amine Number or weight average Amine Number in a range of from about 3-1000, from about 3-500 or from about 3-200.

In some embodiments, the solubility in water of the at least one reactive condensation-curable film-forming amino-silicone pre-polymer, by weight, is less than 0.5% or less than about 0.25%.

In some embodiments, the total concentration of amino-silicone oil within the oil phase, by weight, is at most about 40%, at most about 35%, at most about 30%, at most about 20%, at most about 15%, at most about 10%, or at most about 5%.

In some embodiments, the total concentration of amino-silicone oil within the oil phase, by weight, is within a range of from about 1% to about 40%, from about 5% to about 40%, from about 10% to about 40%, from about 20% to about 40%, from about 1% to about 30%, from about 5% to about 30%, from about 10% to about 30%, from about 15% to about 30%, from about 20% to about 35%, or from about 20% to about 30%.

In some embodiments, the total concentration of non-amino-silicone oil within the oil phase, by weight, is at most about 15%, at most about 12%, at most about 10%, at most about 7%, or at most about 5%, subject to a surface zeta potential of said oil-in-water emulsion being greater than zero, or at least about +1 mV, at least about +2 mV, at least about +3 mV, at least about +5 mV, at least about +7 mV, or at least about +10 mV.

In some embodiments, the total concentration of non-amino-silicone oil within said oil phase, by weight, is within a range of from about 1% to about 15%, from about 3% to about 15%, from about 5% to about 15%, from about 8% to about 15%, from about 1% to about 12%, from about 3% to about 12%, from about 5% to about 12%, from about 3% to about 10%, from about 3% to about 8%, or from about 2% to about 5%.

In some embodiments, the non-amino cross-linking agent includes, mainly includes, or consists of a reactive condensation-curable film-forming non-amino-silicone monomer.

In some embodiments, the non-amino cross-linking agent includes, mainly includes, or consists of an ethyl silicate, a poly(dimethoxysiloxane), and a poly(diethoxysiloxane).

In some embodiments, the total concentration of the non-amino cross-linking agent within the oil phase is at most about 35%, at most about 30%, at most about 20%, at most about 15%, at most about 10%, or at most about 5%, subject to a surface zeta potential of the oil-in-water emulsion being greater than zero, or at least about +1 mV, at least about +2 mV, at least about +3 mV, at least about +5 mV, at least about +7 mV, or at least about +10 mV.

In some embodiments, the total concentration of the pre-polymer, the non-amino cross-linking agent, the solid, hydrophobic reactive inorganic filler, the amino-silicone oil and the non-amino-silicone oil, including any pigment particles and dispersant for the pigment particles, within the oil phase, is at least about 90%, at least about 93%, at least about 95%, at least about 97%, at least about 98%, or at least about 95%, by weight.

In some embodiments, the aqueous phase further contains an oil-in-water emulsifier that is optionally non-ionic, said oil-in-water emulsifier having an HLB number within a range of from about 12 to about 18, from about 12 to about 17, from about 12 to about 16, from about 12 to about 15, or from about 13 to about 16. In some embodiments, the total concentration of the water and any emulsifier, within the aqueous phase, is at least about 90%, at least about 95%, at least about 97% at least about 99%, on a weight basis.

In some embodiments, the mammalian hair to which the oil-in-water emulsion is applied is dry or non-wetted mammalian hair, or to pre-dyed hair. In some embodiments, the mammalian hair to which said oil-in-water emulsion is applied is at least one of unpre-degreased, unpre-shampooed, and unpre-bleached.

In some embodiments, the oil phase further contains at least one pigment selected from a plurality of sub-micronic pigment particles or a plurality of metallic pigments.

In some embodiments, the oil-in-water emulsion further contains a dispersant, the sub-micronic pigment particles being dispersed within the dispersant.

In some embodiments, the aqueous phase contains, by weight, at most about 20%, at most about 10%, at most about 5%, or at most about 2%, of the amount of the pigment within the oil phase. In some embodiments, the aqueous phase is devoid of said pigment.

In some embodiments, at a relative humidity of from about 30% to about 50%, and at a temperature of about 25° C., the at least partially cured film achieves permanence within from about 24 to about 96 hours after the applying of said oil-in-water emulsion on the hair, and optionally, within from about 24 to about 72 hours, within from about 24 to about 48 hours, within from about 24 to about 36 hours, or within from about 24 to about 30 hours.

In another aspect, there is provided a kit for producing a reactive cosmetic composition for coating an external surface of mammalian hair, the kit comprising:

(a) a first compartment containing an oil phase including at least one of an amino-silicone oil and a non-amino-silicone oil, and optionally, a solid, hydrophobic reactive inorganic filler, disposed within said oil phase;

(b) a second compartment containing a formulation including at least one of:

(i) at least one reactive condensation-curable film-forming amino-silicone monomer having a molecular weight of at most about 1000 g/mole; and (ii) a non-amino cross-linking agent; and optionally, (iii) at least one of said amino-silicone oil and said non-amino-silicone oil;

(c) a compartment containing at least one reactive condensation-curable film-forming amino-silicone pre-polymer that, subsequent to condensation curing, forms an elastomer, said pre-polymer including at least one of a reactive condensation-curable film-forming amino-silicone polymer and a reactive condensation-curable film-forming amino-silicone oligomer;

said filler selected or adapted to facilitate curing of said condensation-curable film-forming amino-silicone pre-polymer; said non-amino cross-linking agent adapted or selected to cure said pre-polymer;

wherein said compartment containing at least one reactive condensation-curable film-forming amino-silicone pre-polymer is one of (A) a third compartment; (B) said second compartment; and, (C) said first compartment, subject to said first compartment being substantially devoid of said solid, hydrophobic reactive inorganic filler.

In some embodiments, the first compartment further contains a plurality of pigment particles.

In some embodiments, the kit is devoid of solid, hydrophobic reactive inorganic filler, and the at least one reactive condensation-curable film-forming amino-silicone pre-polymer is disposed in the first compartment.

In some embodiments, the first compartment further contains solid, hydrophobic reactive inorganic filler, disposed within the oil phase.

In some embodiments, wherein a condensation-curable amino-silicone pre-polymer is relatively soluble in water (or becomes so, as a result of hydrolysis), it may be rendered relatively less soluble and even substantially insoluble in water. For instance, a hydrophilic siloxane can be rendered relatively insoluble by reacting it with a different second material (e.g., a hydrophobic silane) capable of modifying its tendency to solubilize in water, the reaction product of the two resulting in a third material being less soluble ("desolubilized") or substantially insoluble ("insolubilized"). This process, which for simplicity may be termed of "desolubilization" or "insolubilization" of a desired reactant, can be carried out prior to the emulsification of the amino-silicone reactant rendered less soluble with the additional constituents of a condensation-curable amino-silicone formulation according to the present teachings. Water-soluble pre-polymers, typically monomers such as silanes, are to be avoided as they would, at low concentrations of relevance to the cost effectiveness of a composition, only form thin monolayers, unable to build-up a coat of sufficient thickness to attach pigments in a color meaningful manner. Moreover, water-soluble pre-polymers, even if forming a very thin coat, would readily wash away in a subsequent rinsing step. Such situation is expected if the pre-polymers mainly include (about 50 wt. % or more) water-soluble pre-polymers. Minor amounts of water-soluble pre-polymers can nevertheless be tolerated, as long as the mixture of all pre-polymers with any additional component of the reactive phase (e.g., silicone oils, amino-silicone oils, non-amino cross-linking agents, reactive fillers, pigment dispersant, etc.) form a water-insoluble oil blend.

As used herein in the specification and in the claims section that follows, the term "solubility" with respect to a component or mixture of components ("component") and a solvent or solvent mixture ("solvent"), is meant to refer to the solubility of the component in the solvent at the native pH, i.e., at the natural pH attained by adding solely the component to the solvent, in the absence of other components and in the absence of any pH modifiers. When the solvent is water, the definition assumes the water has an initial pH of about 7.

While at least partially cured pre-polymers can also be non-tacky (e.g., if cross-linkers and/or curing accelerators are used), the lack of tackiness to the touch is more generally associated with fully cured polymers. Compositions as used in the present methods, advantageously, are rapidly non-tacky to the touch following their application to the hair fibers, to increase compliance when coloring is performed on a living subject. The problem of tackiness has been differently addressed in the art, for instance, by using in hair care products cross-linked polymers, also known as resins (e.g., silicone resins or polycondensates). While this approach can reduce or prevent an unpleasant touch once dried on hair, it also proscribes reactivity amongst such polymers. Therefore, a layer formed by the deposition of cross-linked polymers cannot have sufficient cohesivity to permit a long lasting attachment to the hair surface nor retention of a pigment, if any is present. In such cases, rinsing is typically avoided, as it may readily wash out any loosely attached pigment, if any.

While some cross-linked polymers can also be purchased under the determination of being possibly only partially cured by their manufacturer, the ability of such commercially available polymers to further cure remains highly hypothetical under typical coloring conditions according to the present teachings. Such condensation reaction, if any, would be very slow at ambient temperature (as suggested by their very long shelf life of almost a year) and would require elevated temperatures to proceed at a fast enough pace (e.g., achieving sufficient curing to maintain coloration in less than a week). However, such elevated temperatures are not practical for living subjects, so that in fact commercially available cross-linked polymers can be considered fully cross-linked were they to be used in methods of the present disclosure.

In contrast, by using in the present disclosure reactive materials (or constituents having substantially retained their reactivity), the cross-linking density of the amino-silicone film can be managed by choosing the suitable pre-polymers and cross-linkers, and their respective amounts, allowing the inventors to control the initial viscosity of the composition, the mechanical properties and the thickness of the cured film, the cohesion of the cured film, the feel, and the tackiness of the coated hair etc.

According to an aspect of some embodiments disclosed herein, there is provided a method of coloring or cosmetically treating an external surface of mammalian hair, the method comprising:
(a) applying, on the external surface of individual hairs of the mammalian hair, a formulation comprising:
(i) water;
(ii) at least one reactive condensation-curable film-forming amino-silicone pre-polymer that, subsequent to condensation curing, forms an elastomer; and optionally,
(iii) a plurality of sub-micronic organic or inorganic pigment particles;
(iv) at least one dispersant for dispersing the sub-micronic pigment particles in the formulation;
(v) at least one cross-linking agent adapted to cure the at least one pre-polymer, the cross-linking agent having a low molecular weight of at most about 1,000 g/mol;
(b) after enabling the partial condensation curing to ensue, at a temperature of up to about 60° C., to form an at least partially cured film on the external surface of the individual hairs, washing the hair with a rinsing liquid to leave the pigmented, at least partially cured film on the external surface of the individual hairs.

In some embodiments, the cross-linking agent of (v) can be an amino-silicone monomer. An amino-silicone monomer can thus be considered either as a pre-polymer or as a cross-linker, the terminological distinction depending on the other reactive constituents of the composition, if any. As used in the present specification, the amino-silicone monomers are sometimes referred to as cross-linkers, for instance, when present in a relatively low amount in a composition additionally comprising reactive amino-silicone oligomers or polymers present in a relatively higher amount, or when the composition is devoid of dedicated (non-amino) cross-linkers, or when the sole pre-polymers are monomers which therefore serve both as building blocks and cross-linkers for the amino-silicone film.

In some embodiments, the amino-silicone pre-polymer(s) consists or consists essentially of amino-silicone monomer(s), including mixture thereof. Amino-silicone monomers are able to condensation-cure more rapidly than their oligomer or polymer counterparts, in view of their smaller size/higher accessibility to reactive groups. Such monomers can form three-dimensional (3D) network with high cross-linking density. In some embodiments, when the amino-silicone pre-polymers are predominantly monomers, the reactive oil phase can further include silicone oils and/or amino-silicone oils.

In some embodiments, the condensation-curable amino-silicone monomer(s) has an Amine Number of at least about 200, at least about 220, at least about 240, at least about 275, at least about 325, or at least about 400. In some embodiments, the amino-silicone monomer(s) has an Amine Number of at most 1500, at most about 1250, at most about 1150, at most about 1050, or at most about 1000. In some embodiments, the amino-silicone monomer(s) has an Amine Number within a range of from about 200 to about 1500, from about 220 to about 1250, from about 200 to about 1250, from about 200 to about 1150, from about 200 to about 1100, from about 220 to about 1250, or from about 220 to about 1150.

In some embodiments, the amino-silicone pre-polymer(s) consists or consists essentially of amino-silicone oligomer(s), including mixture thereof. Amino-silicone oligomers are able to condensation-cure more rapidly than polymer counterparts, while providing a more flexible coat than sole monomers. Such oligomers can form 3D networks with cross-linking lower than monomers and higher than polymers. In some embodiments, when the amino-silicone pre-polymers are predominantly oligomers, the reactive oil phase can further include silicone oils, amino-silicone oils, non-amino cross-linking agents and/or reactive fillers.

In some embodiments, the condensation-curable amino-silicone oligomer(s) has an Amine Number of at least about 20, at least about 40, at least about 60, at least about 75, at least about 85, at least about 100, at least about 125, at least about 150, at least about 200, or at least about 250. In some embodiments, the amino-silicone oligomer(s) has an Amine Number of at most about 600, at most about 500, at most about 450, or at most about 400. In some embodiments, the amino-silicone oligomer(s) has an Amine Number within a range of from about 20 to about 600, from about 40 to about 600, from about 60 to about 500, from about 60 to about 400, or from about 75 to about 500.

In some embodiments, the amino-silicone pre-polymer(s) consists or consists essentially of amino-silicone polymer(s), including mixture thereof. Amino-silicone polymers are able to provide a flexible 3D network with low cross-linking density, as suitable for supple substrates such as hair. In some embodiments, when the amino-silicone pre-polymers are predominantly polymers, the reactive oil phase can further include non-amino cross-linking agents and/or reactive fillers.

In some embodiments, the condensation-curable amino-silicone polymer(s) has an Amine Number of at least about 2, at least about 5, at least about 10, at least about 15, at least about 25, at least about 40, at least about 75, at least about 100, or at least about 125. In some embodiments, the amino-silicone polymer(s) has an Amine Number of at most about 200, at most about 180, at most about 160, or at most about 140. In some embodiments, the amino-silicone polymer(s) has an Amine Number within a range of from about 2 to about 200, from about 5 to about 200, from about 10 to about 200, from about 25 to about 200, from about 5 to about 150, or from about 10 to about 135.

The inventors have found that mixing the different types of pre-polymers or mixing at least a particular type of pre-polymer with additional non-reactive silicones allows tailoring the characteristics of a cured film that may result therefrom, by harvesting the advantages of each type, while reducing their respective drawbacks. For instance, while the following observations may depend on the exact chemical compounds of each sub-type, it is generally observed that monomers, if used alone, can result in the formation of too brittle coats, while polymers alone may be too slow to fully cure or result in coats lacking sufficient cohesivity. Hence, in order to reduce brittleness, it may be desired to reduce the extent of cross-linking amongst the pre-polymers. Such effect can be achieved, for instance, by adding larger pre-polymers, usually condensation-curable amino-silicone polymers. Alternatively or additionally, amino-silicone oils and/or non-amino silicone oils may be added. Such molecules can diminish the cross-linking density, alleviating brittleness.

Too much of such large pre-polymers and silicone oils may reduce cross-linking density and may also compromise various mechanical properties of the film or coating. In addition, too much non-amino silicone oils may reduce the positive charge density of the amino groups, detracting from the electrostatic attraction mechanism, and/or weakening or destroying the self-terminating mechanism of the film.

In some embodiments, the amino-silicone pre-polymers include a mixture of at least two types of pre-polymers selected from condensation-curable amino-silicone monomers, amino-silicone oligomers and amino-silicone polymers. For instance, the pre-polymer mix can comprise condensation-curable amino-silicone monomers (e.g., for their rapidity to cure), condensation-curable amino-silicone oligomers (e.g., for their ability to control the density of the cross-linking) and condensation-curable amino-silicone polymers (e.g., for their contribution to the coat flexibility).

In some embodiments, the condensation-curable amino-silicone monomers are present in a mixture of pre-polymers in an amount greater than the amount of condensation-curable amino-silicone oligomers. In some embodiments, the condensation-curable amino-silicone monomers are present in an amount greater than the amount of condensation-curable amino-silicone polymers. In some embodiments, the condensation-curable amino-silicone monomers are present in an amount greater than the total amount of condensation-curable amino-silicone oligomers and polymers.

When the one or more condensation-curable amino-silicone pre-polymers are present in an oil phase further comprising at least one of the afore-mentioned non-reactive silicones, it is preferred that the oil phase has a positive zeta potential.

In some embodiments, the formulation further comprises a condensation-cure auxiliary, such as a condensation-cure accelerator or catalyst adapted to cure the pre-polymer(s). While temperature can to some extent accelerate the reaction rate of condensation curing, accordingly shortening the time required for partial curing to occur or for curing to complete, this auxiliary factor is not critical for the present disclosure and satisfactory coatings can be obtained at a temperature of up to about 60° C., or up to about 50° C., or up to about 45° C., or up to about 40° C., or up to about 38° C. or up to about 36° C., or up to about 34° C., or up to about 32° C., and optionally at least about 15° C.

Suitable pre-polymers are at ambient temperature (or at any moderate temperature of relevance to the application of the composition) in a liquid state, solids being incompatible for the present purpose. The temperatures of curing (in particular when moderate and of up to about 40° C.) further indicate that the pre-polymers suitable for the present disclosure need not be hot melt polymers.

The amino-silicone pre-polymers suitable for the present disclosure lack a glass transition temperature (Tg). Once applied on the hair fibers and following sufficient curing, a network forms and for the at least partially cured amino-silicone film to behave as a flexible elastomer, lacking brittleness, the pre-polymers preferably cure to form a 3D network having a glass transition temperature (Tg) below about 25° C., namely having a Tg between—about 100° C. and about +20° C., the Tg often not exceeding +10° C., or 0° C., being possibly below about −5° C., below about −15° C., or below about −25° C.; and optionally in the range between about −80° C. and about −20° C. or between about −70° C. and about −30° C. However, brittleness can also be avoided by using very thin coats (e.g., of one micron or less thickness). In such a case, films of cured polymers having a Tg above about 25° C. can also be used. Cured films having a relatively high Tg have a higher cross-linking density than cured films having a comparatively lower Tg. Cured films having a higher Tg/cross-linking density are expected to be more resistant to abrasion, swelling or chemical attacks (e.g., resistant to alcohols).

It should be noted that while silicone polymers are widely used in the field of hair products, for instance for the shine, softness, smoothness, anti-dandruff, hair repair or combability they may provide to hair treated with shampoos or hair conditioners comprising them, such polymers are traditionally elected for their weak and highly reversible attachment to the hair. Such silicones (e.g., polydimethylsiloxanes (PDMS)—non-functional dimethicones) intended to wash away at a first shampoo after their application, some not even resisting natural perspiration, are intrinsically different from the amino-silicone pre-polymers considered for the present disclosure. They are typically non-reactive, or pre-reacted to form a cross-linked polymer ahead of their formulation in a hair care product, hence would lack the ability to form a cohesive film on the hair fiber, achieving at most transient physical deposition.

According to some embodiments, the pigment particles are dispersed in the condensation-curable film-forming amino-silicone pre-polymer and/or in the water (e.g., for metallic pigments). Without wishing to be bound by any particular theory, it is believed that as pigments are being applied in a composition comprising reactive amino-silicones able to complete condensation-curing on the hair fiber, such reaction would "entrap" the pigments in the growing 3D-network of the amino-silicone film. As an amino-silicone film formed according to the present teachings displays at least cohesivity (cross-linking between the pre-polymers to form the film coating the hair), the entrapped pigments cannot wash away significantly, as in the case of mere physical deposition.

The formulations according to the present disclosure including the condensation-curable amino-silicone pre-polymers can be applied on dry hair or on wet hair, indifferently. Preferably, the hair fibers are clean. Application can be made with any appropriate brush, comb or applicator known in the art of hair coloring and even with fingers, if so desired.

According to some embodiments, the method further comprises, subsequent to the formation of an at least partially cured film, optionally pigmented, on the external surface of the individual hairs, further curing the at least partially cured film for a period of at least 4 hours, at least about 6 hours, at least about 12 hours, or at least about 24 hours at a temperature of at least about 15° C. and of at most about 38° C., at most about 36° C., at most about 34° C., or at most about 32° C., so as to obtain full curing of the film, the period optionally being at most about 3 weeks, at most about 2 weeks, at most about 10 days, at most about 7 days, at most about 5 days, at most about 3 days, or at most about 2 days. In various embodiments, the period may be within a range of from about 6 to about 36 hours, from about 6 to about 24 hours, from about 6 to about 18 hours, or from about 6 to about 12 hours.

According to some such embodiments, further curing over the specified period (for the duration of the period) is effected or transpires solely by or substantially solely by humidity or ambient humidity. According to alternative embodiments, further curing over the specified period is effected or occurs in the absence of any added non-cationic surfactant. In some embodiments, shampooing of the hair during the period of the further curing is effected with a cationic shampoo, and within at least two days, at least three days, at least five days, or at least a week of the original liquid rinsing.

According to some embodiments, the reactive condensation-curable amino-silicone pre-polymer, the cross-linking agent and the optional catalyst are present in a same formulation each separately dispersed in the carrier in the form of emulsion droplets. Emulsions are known two-phase systems, and in some embodiments oil-in-water emulsions are preferred. Emulsions typically requires emulsifiers (when the constituents lack self-emulsifying properties), which can be ionic or non-ionic.

According to some embodiments, the method further comprises combining at least first and second sub-formulations to produce the formulation, the first sub-formulation including water, the pre-polymer, the plurality of sub-micronic pigment particles and the dispersant; and the second sub-formulation including the cross-linking agent. In particular embodiments, the cross-linking agent, if consisting for instance of non-amino condensation-curable monomers or oligomers, may be disposed in the second sub-formulation as a negatively-charged emulsion in water.

In some embodiments, the method further comprises combining with at least one of the afore-said sub-formulations, a third sub-formulation comprising a 3D network former, which in one embodiment can be a reactive filler, such as hydrophobic fumed silica, having an amorphous structure.

The combination of the at least two sub-formulations can result in an emulsion, typically an oil-in-water emulsion. The hydrophobic fumed silica, also referred to as a reactive filler, if present, is typically disposed within the oil phase of the oil-in-water emulsion. In some embodiments, the concentration of the hydrophobic fumed silica within the oil phase is within a range of from about 0.2 to about 12 wt. %, from about 0.2 to about 10 wt. %, from about 0.2 to about 8 wt. %, from about 0.4 to about 10 wt. %, from about 0.4 to about 8 wt. %, from about 0.6 to about 10 wt. %, from about 0.6 to about 8 wt. %, from about 0.8 to about 8 wt. % or from about 0.8 to about 6% by total weight of the oil phase.

In some embodiments, the concentration of the hydrophobic fumed silica within the oil-in-water emulsion is within a range of from about 0.005 to about 0.5 wt. % or from about 0.005 to about 0.3 wt. % by total weight of the emulsion.

In some embodiments, the hydrophobic fumed silica has an average particle size ($D_V50$) within a range of from about 20 to about 500 nm, from about 20 to about 250 nm, from about 20 to about 200 nm, from about 40 to about 300 nm, from about 60 to about 300 nm, from about 60 to about 250 nm or from about 60 to about 200 nm.

In some embodiments, the refractive index of the hydrophobic fumed silica is within a range of ±10%, ±7%, ±5% or ±3% of a refractive index of the oil phase, not including any pigment particles disposed therein.

It is believed that fumed silica, if disposed in the non-reactive phase of the composition during application, would not only deprive the reactive oil phase of the composition from its contribution to the formation of the amino-silicone film, but may further interact with the droplets of amino-silicone pre-polymers reducing their attachment to the hair fibers. Hydrophilic fumed silica, typically used as thickeners of aqueous compositions, would therefore be detrimental to compositions according to the present teachings. For instance, aggregates of fumed silica, as generally used for thickening purposes, may additionally affect the gloss and the feel of the hair. In contrast, reactive hydrophobic fumed silica well dispersed in oil are size reduced to have dimensions compatible with the desired reactive surface area intended to promote the 3D network formation and the thickness of the coatings, thus avoiding any negative impact on hair appearance and touch.

According to some such embodiments, the method further comprises mixing together the at least first and second sub-formulations at most about 4 hours, at most about 2 hours, at most about 60 minutes, at most about 45 minutes, at most about 30 minutes, at most about 20 minutes, or at most about 10 minutes prior to applying. The mixing of the sub-formulations (if two or more) can be performed a few seconds before application to the hair, at least about 10 seconds, at least about 30 seconds, at least about 60 seconds or at least about 5 minutes prior to applying the formulation combined therefrom. In some embodiments, when two or more sub-formulations are mixed for the preparation of the complete formulation being applied to the hair fibers, the mixing can be performed within a range of from about 10 seconds to about 60 minutes prior to application, or within about 20 seconds and about 30 minutes, or within about 1 to about 20 minutes.

According to some embodiments, the pre-polymer is dispersed in the form of an emulsion.

According to some embodiments, the formulation or sub-formulation further comprises a non-ionic or an anionic emulsifier.

According to some embodiments, the formulation is charged and has a positive surface zeta potential of at least about +1 mV, at least about +2 mV, at least about +3 mV, at least about +5 mV, at least about +7 mV, at least about +10 mV, at least about +15 mV, at least about +20 mV, at least about +30 mV, at least about +40 mV, or at least about +60 mV; and of no more than about +100 mV, or no more than about +80 mV. In some embodiments, the formulation has a positive surface zeta potential within the range of from about 1-100 mV, from about 2-100 mV, from about 3-100 mV, from about 5-100 mV, from about 7-100 mV, from about 1-30 mV, from about 1-20 mV, from about 1-15 mV, from about 10-80 mV, from about 15-80 mV, from about 20-80 mV or from about 30-60 mV.

According to some embodiments, the first sub-formulation containing the pre-polymer is charged and has a positive surface zeta potential of at least about +1 mV, at least about +2 mV, at least about +3 mV, at least about +5 mV, at least about +7 mV, at least about +10 mV, at least about +15 mV, at least about +20 mV, at least about +30 mV, at least about +40 mV, or at least about +60 mV; and at most about +100 mV, or at most about 80 mV. In some embodiments, the first sub-formulation has a positive surface zeta potential within the range of from about 1-100 mV, from about 2-100 mV, from about 3-100 mV, from about 5-100 mV, from about 7-100 mV, from about 1-30 mV, from about 1-20 mV, from about 1-15 mV, from about 10-80 mV, from about 15-80 mV, from about 20-80 mV or from about 30-60 mV.

According to some embodiments, the second sub-formulation includes the cross-linking agent is charged and has a negative surface zeta potential whose negativity is at least about −1 mV, at least about −10 mV, at least about −20 mV, at least about −40 mV, or at least about −60 mV; and whose negativity is at most about −100 mV, or at most about −80 mV. In some embodiments, the second sub-formulation has a negative surface zeta potential within the range of from about −100 mV to about −1 mV, or from about −100 mV to about −10 mV, from about −80 mV to about −20 mV, or from about −80 mV to about −40 mV. Typically, such negative zeta potential is observed when the cross-linker lacks an amine moiety.

In some embodiments, the zeta potential can be measured at a pH of at least about 8.0 and at most about 12.0, said measurement being optionally performed at a pH of about 10.0. Typically, the zeta potential is measured at the native pH of the oil-in-water emulsion. Conveniently, the measurement of the zeta potential of a material or of a composition can be performed at low concentration of the material in an appropriate carrier or on a diluted form of the composition. For instance, a test sample may comprise about 2 wt. % or less of solid material or composition ingredients, about 1 wt. % or less, or about 0.1 wt. % or less.

According to some embodiments, the reactive condensation-curable amino-silicone pre-polymer satisfies at least one, at least two or at least three of the following structural properties:

a) the pre-polymer includes reactive groups selected from the group consisting of alkoxy-silane reactive groups, silanol reactive groups and combinations thereof;
b) the pre-polymer has no glass transition temperature;
c) the pre-polymer is not solid at about 25° C.;
d) the pre-polymer has a viscosity in the range of from about 2-2,000 milliPascal-second (mPa·s, also referred to as cps), from about 10-2,000 mPa·s, from about 2-1,000 mPa·s, from about 2-500 mPa·s, from about 5-100 mPa·s, from about 10-20,000 mPa·s, from about 10-15,000 mPa·s, from about 20-15,000 mPa·s, from about 30-15,000 mPa·s, from about 40-10,000 mPa·s or from about 50-10,000 mPa·s as measured at about 25° C. in a suitable rheometer;
e) the pre-polymer is capable of wetting said hair;
f) the pre-polymer is a film-forming pre-polymer;
g) the pre-polymer includes a primary amine;
h) the pre-polymer has an Amine Number in the range of from about 3-1000, 3-500 or from about 3-200;
i) the pre-polymer includes terminal amino-moieties;
j) the pre-polymer includes pendant amino-moieties;
k) the pre-polymer is miscible in a reactive oil phase comprising, in addition to the pre-polymer, at least one of a different pre-polymer, a non-reactive silicone oil, a non-reactive amino-silicone oil, a cross-linker and a pigment dispersant;
l) the pre-polymer has a refractive index within ±10% of a refractive index of a reactive oil phase comprising at least one of a different pre-polymer, a non-reactive silicone oil, a non-reactive amino-silicone oil, a cross-linker, a reactive filler and a pigment dispersant;
m) the pre-polymer is hydrophobic;
n) the pre-polymer has a solubility in water (e.g., circa pH 7) at about 25° C. of less than about 5% by weight, less than about 2% by weight, less than about 1% by weight, less than about 0.5% by weight, or less than about 0.25% by weight;
o) the pre-polymer is a linear or a branched polymer;
p) the pre-polymer is a linear or a branched oligomer;
q) the pre-polymer is a monomer;
r) the pre-polymer has a ratio of Amine Number (AN) to viscosity (Visc.) in mPa·s, which when multiplied by about 1000, is of at least about 40, at least about 100, at least about 200, or at least about 500, which can be mathematically expressed as about $1000 \cdot (AN/Visc.) \geq 40$, and so on; and
s) the pre-polymer is devoid of cyclic moieties.

While silicone materials solid at about 25° C. have been disclosed as suitable to improve hair lubricity, when applied as particles, it is readily apparent that such solids are non-reactive and unable to participate in the prospective formation of a continuous layer, as enabled by the coalescence of droplets of silicone materials fluid at same temperature. Solid silicone particles are believed to act as friction reducers in a manner similar to mechanical bearings.

In some embodiments, the pre-polymer has no glass transition temperature and has a solubility in water (pH 7) at about 25° C. of less than about 1 wt. %, less than about 0.5 wt. %, or less than about 0.25 wt. % by weight of aqueous composition.

In some embodiments, the pre-polymer has no glass transition temperature and has a viscosity in the range of 2-2,000 mPa·s, 10-2,000 mPa·s, 2-1,000 mPa·s, 2-500 mPa·s, 5-100 mPa·s, 10-20,000 mPa·s, 10-15,000 mPa·s, 20-15,000 mPa·s, 30-15,000 mPa·s, 40-10,000 mPa·s or 50-10,000 mPa·s as measured at 25° C.

In some embodiments, the pre-polymer has no glass transition temperature and has a reactive group selected from the group consisting of alkoxy-silane reactive groups, silanol reactive groups and combinations thereof.

In some embodiments, the pre-polymer has an Amine Number in the range of 3-1000, 3-500 or 3-200 and has a viscosity in the range of 2-2,000 mPa·s, 10-2,000 mPa·s, 2-1,000 mPa·s, 2-500 mPa·s, 5-100 mPa·s, 10-20,000 mPa·s, 10-15,000 mPa·s, 20-15,000 mPa·s, 30-15,000 mPa·s, 40-10,000 mPa·s or 50-10,000 mPa·s as measured at 25° C.

In some embodiments, the pre-polymer has an Amine Number in the range of 3-1000, 3-500 or 3-200 and has a solubility in water at 25° C. of less than 1 wt. %, less than 0.5 wt. %, or less than 0.25 wt. % by weight of aqueous composition.

In some embodiments, the pre-polymer has an Amine Number in the range of from about 3-1000, from about 3-500 or from about 3-200 and is miscible in a reactive oil phase comprising, in addition to the pre-polymer, at least one of a different pre-polymer, a non-reactive silicone oil, a non-reactive amino-silicone oil, a cross-linker and a pigment dispersant.

In some embodiments, the pre-polymer has no glass transition temperature; has a reactive groups selected from the group consisting of alkoxy-silane reactive groups, silanol reactive groups and combinations thereof; and has a viscosity in the range of from about 2-2,000 mPa·s, from about 10-2,000 mPa·s, from about 2-1,000 mPa·s, from about 2-500 mPa·s, from about 5-100 mPa·s, from about 10-20,000 mPa·s, from about 10-15,000 mPa·s, from about 20-15,000 mPa·s, from about 30-15,000 mPa·s, from about 40-10,000 mPa·s or from about 50-10,000 mPa·s as measured at about 25° C. in a suitable rheometer.

In some embodiments, the pre-polymer has an Amine Number in the range of from about 3-1000, from about 3-500 or from about 3-200; has a solubility in water at about 25° C. of less than about 1 wt. %, less than about 0.5 wt. %, or less than about 0.25 wt. % by weight of aqueous composition; and is miscible in a reactive oil phase comprising, in addition to the pre-polymer, at least one of a different pre-polymer, a non-reactive silicone oil, a non-reactive amino-silicone oil, a cross-linker and a pigment dispersant.

In some embodiments, the pre-polymer has no glass transition temperature; has a reactive groups selected from the group consisting of alkoxy-silane reactive groups, silanol reactive groups and combinations thereof; has a viscosity in the range of from about 2-2,000 mPa·s, from about 10-2,000 mPa·s, from about 2-1,000 mPa·s, from about 2-500 mPa·s, from about 5-100 mPa·s, from about 10-20,000 mPa·s, from about 10-15,000 mPa·s, from about 20-15,000 mPa·s, 30-15,000 mPa·s, from about 40-10,000 mPa·s or from about 50-10,000 mPa·s as measured at about 25° C.; and has an Amine Number in the range of from about 3-1000, from about 3-500 or from about 3-200.

In some embodiments, the pre-polymer has no glass transition temperature; has a reactive groups selected from the group consisting of alkoxy-silane reactive groups, silanol reactive groups and combinations thereof; has a viscosity in the range of from about 2-2,000 mPa·s, from about 10-2,000 mPa·s, from about 2-1,000 mPa·s, from about 2-500 mPa·s, from about 5-100 mPa·s, from about 10-20,000 mPa·s, from about 10-15,000 mPa·s, from about 20-15,000 mPa·s, from about 30-15,000 mPa·s, from about 40-10,000 mPa·s or from about 50-10,000 mPa·s as measured at about 25° C.; has an Amine Number in the range of from about 3-1000, 3-500 or from about 3-200; and has a solubility in water at about 25° C. of less than about 1 wt. %, less than about 0.5 wt. %, or less than about 0.25 wt. % by weight of aqueous composition.

In some embodiments, a reactive oil phase comprising at least one of a pre-polymer, a non-reactive silicone oil, a non-reactive amino-silicone oil, a cross-linker, a reactive filler and a pigment dispersant, has a viscosity in the range of from about 2-2,000 mPa·s, from about 2-1,000 mPa·s, from about 2-500 mPa·s, from about 2-400 mPa·s, from about 2-300 mPa·s, from about 2-200 mPa·s, from about 2-200 mPa·s, or from about 2-50 mPa·s, as measured at about 25° C. in a suitable rheometer.

In some embodiments, a reactive oil phase comprising at least one of a pre-polymer, a non-reactive silicone oil, a non-reactive amino-silicone oil, a liquid hydrophobic cross-linker and a pigment dispersant, has no glass transition temperature.

In some embodiments, a reactive oil phase comprising at least one of a pre-polymer, a non-reactive silicone oil, a non-reactive amino-silicone oil, a liquid hydrophobic cross-linker and a pigment dispersant, has a solubility in water at about 25° C. of less about 5% by weight, less than about 2% by weight, less than about 1% by weight, less than about 0.5% by weight, less than about 0.25% by weight of the total aqueous composition.

When assessing the solubility of an oil phase is desired, but the phase is in emulsified or any other mixed form, the oil can be separated by any suitable method known to the skilled person (e.g., by centrifugation). The oil phase so extracted can then be assessed for any desired property (e.g., solubility, glass transition temperature, chemical analysis), by any appropriate standard method.

According to some embodiments, suitable reactive condensation-curable amino-silicone pre-polymers can be selected from the group comprising: Dynasylan® SIVO 210, KF-857, GP-145, GP-34, GP-397, GP-657, GP-846, KF-862, SF 1706, TSF 4703, TSF 4707, TSF 4708, OFX 8630, OFX 8822, Dynasylan® 1146, SIO6629.1, DMS-S12, ATM 1322, Bis[methyldiethoxysilyl-propyl] amine, Diethoxydimethylsilane, and any commercially available equivalent of the foregoing.

According to some embodiments, the formulation or sub-formulation further comprises a cosmetically acceptable oil, miscible with the at least one pre-polymer, and/or miscible with the cross-linking agent, and/or miscible with the condensation-cure accelerator or catalyst, the cosmetically acceptable oil including, but not limited to, a silicone oil.

A cosmetically acceptable oil and more generally any cosmetically acceptable ingredient, and similarly cosmetically acceptable compositions or formulations, refer to the suitability of such materials for use in contact with keratinous fibers, in particular human hair, without undue toxicity, instability, allergic response, and the like.

In some embodiments, the formulation or sub-formulations is substantially devoid of an organic solvent or of a water-miscible co-solvent able to solubilize at least one of a pre-polymer, a non-reactive silicone oil, a non-reactive amino-silicone oil, a liquid hydrophobic cross-linker and a pigment dispersant. A formulation or sub-formulation is substantially devoid of such solubilizing solvents if the solubilized material or mixture thereof, if any such solubilization takes place, has a solubility at about 25° C. of less than about 5% by weight, less than about 2% by weight, less than about 1% by weight, less than about 0.5% by weight, less than about 0.25% by weight of the an aqueous composition comprising same solvents in same amounts.

As used herein in the specification and in the claims section that follows, the term "organic solvent" within or with respect to an oil phase, refers to an organic liquid that is disposed within an oil phase containing at least one solute, and which organic liquid does not positively participate in the intra-polymer bonding nor in the bonding to the surface of the mammalian hair.

As used herein in the specification and in the claims section that follows, the term "organic solvent" within or with respect to an aqueous phase, refers to an organic liquid that is at least partially miscible within an aqueous phase, the organic liquid further increases the solubility, within the aqueous phase, of at least one component that is disposed in the oil phase.

Organic solvents or water-miscible co-solvents may include, by way of non-limiting examples, volatile $C_1$-$C_6$ alkanols, such as ethanol; volatile $C_5$-$C_7$ alkanes such as hexane; esters of liquid $C_1$-$C_{20}$ acids and of volatile $C_1$-$C_8$ alcohols such as methyl acetate; volatile ketones that are liquid at RT, such as acetone; volatile hydrocarbon-based oils, such as $C_8$-$C_{16}$ alkanes, for instance isododecane; volatile ethers or glycol ethers such as dimethoxymethane or diethylene glycol monomethyl ether; and mixtures thereof.

It is believed that such solvents, in addition to detracting from the efficacy of an oil phase and/or preventing the formation of an emulsion, may also, if present in the same phase as the condensation-curable amino-silicone pre-polymer, reduce or delay condensation curing.

In some embodiments, the formulation or sub-formulation according to the present teachings contains about 10% of an organic solvent or water-miscible co-solvent or less by weight of the formulation or sub-formulation, or less than about 5 wt. %, or less than about 4 wt. %, or less than about 3 wt. %, or less than about 2 wt. %, or less than about 1 wt. % of any such solvent or mixture thereof.

According to some embodiments, the formulation or sub-formulation, has a pH of at least about 4.0, at least about 5.5, at least about 7.0, at least about 8.5, at least about 10.0; and optionally of at most about 12.0 or at most about 11.0. In some embodiments, the formulation or sub-formulation, has a pH within a range of from about 4.0 to about 12.0, from about 5.5 to about 12.0, from about 7.0 to about 11.0, or from about 8.5. to about 11.0. A pH above the isoelectric point of the hair fibers to be coated enables a negative charging of the fibers and/or a positive charging of amino functions of the amino-silicone pre-polymers. Taking for example human hairs, the isoelectric point was reported to be between about pH 2.5 (e.g., for damaged hair) and approximately pH 3.5-3.7 (e.g., for virgin hair). As shall be detailed in the following, a gradient of charge between the surface of hair fibers and the pre-polymers of the composition is expected to permit electrostatic attachment between the two, as a first step in the formation of a coat. In particular embodiments, the formulation has a basic pH of at least about 7.5, at least about 8.0, at least about 9.0 or at least about 9.5. According to some embodiments, the formulation is applied on the hair for sufficient time for such a gradient to drive enough droplets to wet and form a continuous coat on the fibers. In one embodiment, the application time is between about 5 seconds and about 10 minutes, or between about 10 seconds and about 2 minutes, or of about 1 minute or less. According to some embodiments, the duration of time enabling the partial curing is between about 5 seconds and about 30 minutes, or between about 1 minute and about 15 minutes. While partial curing may initiate at the time of application of the formulation, it can also proceed once excess of the formulation is removed (e.g., before rinsing the hair fibers).

According to some embodiments, the rinsing liquid is (i) water, or (ii) a cationic rinsing liquid, or (iii) a rinsing liquid devoid of non-cationic surfactants, degreasing agents and/or swelling agents, the degreasing and swelling agent respectively able to degrease and swell the at least partially cured pigmented film. In some embodiments, the rinsing liquid has a pH of at least about 6, at least about 7, at least about 8, or at least about 9.

According to some embodiments, the cationic shampoo or the cationic rinsing liquid includes a cosmetically-acceptable primary, secondary, tertiary, or quaternary ammonium compound or polymer.

According to some embodiments, the cationic shampoo or the cationic rinsing liquid includes a polyquaternium polycationic polymer having a quaternary ammonium function.

According to some embodiments, the dispersant is present in the formulation or sub-formulation in an amount ranging from about 25% to about 400% by weight of the submicronic organic or inorganic pigment particles. In some embodiments, the dispersant and the pigment particles are present at a relative weight per weight ratio in the range of from about 0.5:1 to about 2:1, from about 0.75:1 to about 1.5:1, or from about 0.8:1 to about 1.2:1.

According to some embodiments, the dispersant adapted to disperse the pigments is compatible with the condensation-curable formulation. By compatible, it is meant, for instance, that the pigment dispersant is miscible in the reactive oil phase of the formulation, that the pigment dispersant does not delay, reduce or prevent curing, and that the pigment dispersant is stable (e.g., non-reactive) during the size reduction of the pigment. Preferably, the pigment dispersant can have a positive charge.

Such dispersant can have a silicone backbone, such as silicone polyether and silicone amine dispersants. Suitable pigment dispersants include for example silicone amines such as BYK LPX 21879, by BYK, GP-4, GP-6, GP-344, GP-851, GP-965, GP-967, and GP-988-1, by Genesee Polymers, silicone acrylates such as Tego® RC 902, Tego® RC 922, Tego® RC 1041, and Tego® RC 1043, by Evonik, PDMS silicones with a carboxylic function such as X-22162 and X-22370 by Shin-Etsu, silicone epoxy such as GP-29, GP-32, GP-502, GP-504, GP-514, GP-607, GP-682, and GP-695, by Genesee Polymers, or Tego® RC 1401, Tego® RC 1403, Tego® RC 1412, by Evonik.

Pigment dispersants having functional moieties able to react with the reactants of the reactive oil phase may advantageously, in addition to pigment dispersion per se, further improve the amino-silicone 3D network forming therefrom. For instance, silicone epoxy pigment dispersants can favorably interact with the amine-moieties of the amino-silicone pre-polymer to further increase the cohesivity of the pigmented amino-silicone film.

Generally, a material used in the compositions according to the present teachings is said to be compatible with another, if it does not prevent its activity or does not reduce it to an extent that would significantly affect the intended purpose. For instance, a pigment dispersant would not be compatible if, among other things, preventing the curing of the condensation-curable amino-silicone pre-polymers, or reducing or retarding curing to an extent that the amino-silicone film would not sufficiently and/or rapidly attach to a target fiber, or would be deleterious to the pigments, and any like undesired effects. In some embodiments, compatibility may additionally mean that the materials deemed compatible share a common property, such as a common silicon-based chemistry or a similar physical parameter. For instance, materials having a similar refractive index (RI; within ±10% from one another) are believed to yield clearer cured films, as compared to materials having relatively dissimilar RI that may appear more turbid.

The silicone amine dispersants are positively charged and can be advantageous in some embodiments according to the present teachings.

According to some embodiments, the plurality of sub-micronic organic or inorganic pigment particles provide a first color, the method further comprising subsequent to step (c) leaving on the individual hairs an at least partially cured film pigmented with the first color, repeating steps (a) to (c) the sub-micronic organic or inorganic pigment particles of repeated step (b) providing a second color, the second color being same or different from the first color.

According to some embodiments, the method further comprises, prior to step (a), or prior to a first step (a) if repeated, applying a degreasing agent to effect degreasing of the external surface of the hair without effecting degreasing of an inner surface of the hair and/or without penetration of the degreasing agent within the hair and/or without bleaching the hair.

According to some embodiments, the method further comprises, prior to step (a), or prior to a first step (a) if repeated, and optionally following a degreasing step, if performed, applying, on the external surface of the individual hairs, a film-forming hair masking binder formulation so as to produce a polymeric film on the hair.

According to some embodiments, the film-forming hair masking binder formulation further includes (i) a plurality of sub-micronic organic or inorganic pigment particles, and/or (ii) metallic-looking particles and/or flakes, so as to produce a tinted binder polymeric film on the external surface of the individual hairs or on top of a previously laid-down film on the hair.

According to some embodiments, the film-forming hair masking binder formulation comprise at least one reactive condensation-curable amino-silicone elastomer, at least one cross-linking agent, at least one emulsifier and optionally, at least one catalyst emulsified in an aqueous carrier.

According to some embodiments, the method further comprises, after a) applying the film-forming hair masking binder formulation:
b) allowing the film-forming binder to preliminarily cure;
c) washing the hair with a rinsing liquid to leave a preliminarily cured polymeric film on the external surface of the individual hairs, the film being optionally tinted;
d) applying to the preliminarily cured film a flake dispersion including of a plurality of metallic-looking pigment flakes, a dispersant and an aqueous carrier;
e) washing the fibers with a rinsing liquid to leave a layer of metallic-looking pigment flakes on and adhering to the preliminarily cured film.

According to a further aspect, there is provided a method for masking keratinous fibers or color thereof, the method comprising
a) applying to an external surface of individual fibers a film-forming hair masking binder formulation, the formulation including at least one reactive condensation-curable amino-silicone elastomer, at least one cross-linking agent, at least one emulsifier and optionally, at least one catalyst emulsified in an aqueous carrier; the formulation optionally further including pigments;
b) allowing the film-forming binder to preliminarily cure;
c) washing the hair with a rinsing liquid to leave a preliminarily cured polymeric film on the external surface of the individual hairs, the film being optionally tinted;
d) applying to the preliminarily cured film a flake dispersion including of a plurality of metallic-looking pigment flakes, a dispersant and an aqueous carrier;
e) washing the fibers with a rinsing liquid to leave a layer of metallic-looking pigment flakes on and adhering to the preliminarily cured film.

According to some embodiments, the metallic pigment flakes have an average longest dimension in the range of from about 2 μm to about 20 μm and an average thickness in the range of from about 50 nm to about 500 nm. The dimensions of metallic pigments need not fulfill the size ranges of the non-metallic pigments, generally sub-micronic in at least one of their $D_v50$ or $D_v90$ values.

According to some embodiments, the pigment flakes are metallic pigment flakes containing, coated with, consisting essentially of, or made of metals, alloys and oxides thereof, said flakes being selected from the group comprising aluminum flakes, brass flakes, bronze flakes, copper flakes, gold flakes, mica coated flakes, silica coated flakes and silver flakes.

According to some embodiments, the metallic-looking pigment flakes are further coated with a least one coupling agent capable of covalently binding the reactive amino-silicone elastomer of the film-forming hair masking binder formulation.

According to some embodiments, the at least one coupling agent is a cosmetically acceptable coupling agent selected from the group consisting of acrylate coupling agents, thiol coupling agents, anhydride coupling agents, epoxy coupling agents, and silanol coupling agents.

In some embodiments, the acrylate coupling agent is selected from the group comprising of penta erythrytol tetra acrylate, pentaerythrityl triacrylate, di-trimethylol-propane tetraacrylate, PEG-trimethylol-propane triacrylate, and mixtures thereof.

In some embodiments, the thiol coupling agents can be pentaerythrityl tetramercaptopropionate; mercaptopropyltrimethoxysilane; trimethylolpropane tris-mercapto-propionate. In some embodiments, the anhydride coupling agent is polymaleic anhydride. In some embodiments, the epoxy coupling agents can be 4-methylen-2,6-epoxydecane; 3-methyl-1-phenyl-3-hexene 1,5-epoxide. In some embodiments, the silanol coupling agent is glycidoxypropyl trimethoxysilane.

According to some embodiments, the pigment flakes are charged at a polarity opposite a polarity of the preliminarily cured hair masking film.

According to some embodiments, the method further comprises, subsequent to at least partially condensation curing of pigmented film, applying a clear protective coating, the protective coating including an amino-silicone elastomer, a cross-linking agent, an emulsifier and an optional catalyst emulsified in an aqueous carrier.

According to some embodiments, the fully cured film is wash resistant, wash resistance meaning that the hair can be washed at least about 20 times with water and retain an Optical Density (OD) value of at least about 80% of an original OD value as determined following full curing. Wash resistance of hair coated with a fully cured film can also be referred to as "cured wash resistance".

According to some embodiments, the at least partially cured film is wash resistant, wash resistance meaning that the hair can be washed at least about 10 times with a cationic shampoo and retain an Optical Density (OD) value of at least about 80% of an original OD value as determined following said at least partial curing.

Wash is performed by completely immersing the hair fibers in the washing liquid, rinsing liquid, or water, as desired. In some embodiments, washing is performed within about 30 minutes, within about 20 minutes, within about 15 minutes, within about 10 minutes, within about 5 minutes, within about 3 minutes, within about 2 minutes, or within about 1 minute, of applying of said oil-in-water emulsion. The fibers are generously massaged with the liquid for about one minute and are dried (e.g., with blowing air at ambient temperature).

According to some embodiments, the method further comprises, subsequent to at least partial curing of one or more films as applied in one or more steps, removing the films from the individual hairs by applying a silicone decuring agent in an amount and for a time period sufficient to at least partially decure the films, the application of the decuring agent for a sufficient time being followed by rinsing away the decured silicone. The removal of the films including at least one colored film can be performed at any desired time point after coloration (e.g., within days, within weeks or within months from application).

For instance, conventional permanent coloring methods usually require specific coloration to be reapplied within a few weeks from an initial coloration, coloring then only the region of the newly grown hair near the hair roots. As the present method allows, in some embodiments, for a rapid and non-damaging removal of a coloring film as contemplated herein, the hair could be advantageously decolored (and if desired recolored) in its entirety, providing for an even coloring of the hair fibers from roots to tips.

According to some embodiments, the silicone decuring agent is selected from the group including fluoride salts (including but not limited to tetra butyl ammonium fluoride (TBAF) and RonaCare® Olaflur), organic sulfonic acids (including but not limited to dodecyl benzene sulfonic acid (DBSA)) and an organic or inorganic base and salts thereof (including but not limited to tetra butyl ammonium hydroxide (TBAH), tetra butyl ammonium bromide (TBAB), tetra butyl ammonium chloride (TBAC), potassium hydroxide (KOH) and potassium tert-butoxide ($K(CH_3)_3CO$)).

In some embodiments, the fully cured film has a thickness above fiber surface of at least about 100 nm, at least about 500 nm, or at least about 1 µm, said thickness not exceeding about 5 micrometers, being no greater than about 4 µm, no greater than about 3 µm, or no greater than about 2 µm. In some embodiments, the fully cured film has a thickness in the range of between about 100 nm to about 5 µm, from about 100 nm to about 4 µm, from about 300 nm to about 3 µm, from about 300 nm to about 2 µm, from about 500 nm to about 2 µm, or from about 500 nm to about 1 µm.

According to an aspect of some embodiments disclosed herein, there is provided a kit for coloring or cosmetically treating an external surface of keratinous fibers, in one embodiment mammalian hair optionally attached to the mammalian subject, the kit comprising:
(a) a first compartment containing a pigmented formulation including:
(i) at least one reactive condensation-curable film-forming amino-silicone pre-polymer;
(ii) at least one dispersed plurality of sub-micronic organic or inorganic pigment particles;
(iii) at least one dispersant; and optionally
(iv) at least one silicone oil miscible with the film-forming amino-silicone pre-polymer;
(b) a second compartment containing water and an emulsifier to form an emulsion when mixed with the content of the first compartment;
(c) a third compartment, said third compartment containing at least one cross-linking agent and optionally at least one silicone oil miscible with the at least one cross-linking agent;
(d) a compartment containing water and at least one emulsifier to form an emulsion when mixed with the content of the third compartment, wherein the compartment of (d) is a fourth compartment or a second compartment.

In some embodiments, wherein the kit comprises more than one type of reactive condensation-curable film-forming amino-silicone pre-polymers, and in the event the pre-polymers may at least partially react with one another, the pre-polymers can be supplied in separate compartments. For instance, if the pre-polymers include condensation-curable oligomers or polymers that may react with amino-silicone monomers acting in such instance as cross-linking agents, the different pre-polymers can be separated and, by way of example, the amino-silicone monomers can be supplied in the third above-mentioned compartment or in a further additional compartment.

According to some embodiments, the kit further comprises at least one curing auxiliary compartment, the at least one curing auxiliary compartment containing at least one curing accelerator or catalyst in water and optionally at least one silicone oil miscible with the curing accelerator or catalyst, and an additional compartment containing water and at least one emulsifier to form an emulsion when mixed with the content of the curing auxiliary compartment, the additional compartment optionally being the second compartment or the fourth compartment.

The contents of the compartment or compartments containing: at least one reactive condensation-curable film-forming amino-silicone pre-polymer, a non-amino cross-linking agent, at least one of an amino-silicone oil and a non-amino-silicone oil, optionally, a solid, hydrophobic reactive inorganic filler and sub-micronic organic or inorganic pigment particles and dispersant, followed by emulsification together with the contents of the compartment containing the emulsifier and water. The kit can further comprise a sealable container, wherein the compartments can be mixed as described above. The container can be optionally capped by a removable applicator, such as a brush or a pad connected through a hollow space to the container's seal, allowing the coloring composition to pass through, and transfer to the keratinous fibers for coloration.

Silicone oils are typically non-reactive/non-functionalized molecules of hydrophobic silicones. Such non-functionalized silicone oils can serve as carriers, water repellents, lubricants and like functions. Depending on their molecular weight, silicone oils can be volatile or not. Silicone oils can also be functionalized, for instance, they can include amine moieties, forming amino-silicone oils. In some embodiments, amino-silicone oils are used to modify the charge density of the reactive oil phase (by modifying the amount of amine groups in the oil phase able to interact as herein described). Furthermore, it has been reported that amine-moieties (as present in amino-silicone oils) can catalyze condensation curing of the pre-polymers. Hence, in some embodiments the silicone oil optionally used in the present compositions is an amino-silicone oil.

In some embodiments, examples for suitable non-reactive silicone materials are: GP-965, GP-967, Rhodorsil (Bluesil) 21642, SID 2650-D5, Wacker Finish WR 1100 or Siltech® E-2154.

According to some embodiments, the kit further comprises a rinsing compartment, the rinsing compartment containing a rinsing formulation or a rinsing agent dispersible or soluble in water.

The methods, compositions and kits according to the present teachings advantageously color the keratinous fibers, such as mammalian hair, by providing a coating of pigment on the outer surface of the fiber, with minimal or no penetration of the pigment into the interior of the fiber, such as the hair shaft, thus reducing adverse effects and health concerns typically associated with penetration of conventional chemical compounds, which may lead to hair breakage or brittleness.

The methods, compositions and kits disclosed herein, in at least some embodiments, may provide coloring which is permanent i.e. wash resistant, using conventional, over-the-counter shampoos, after at least about 30 washes, at least about 50 washes, or even after at least about 100 washes, as determined by optical density measurements using yak hair or human hair (e.g., Chinese or European hair). A coloring is shampoo-resistant if the OD measured after shampooing is not below about 80% of the baseline OD as measured following coloring, before any shampooing. Typically, wash-resistance is assessed once the applied coating is deemed substantially cured. In some embodiments, the resistance to shampooing is achieved with cationic shampoos. In some embodiments, the cationic shampoo has a high charge density. In some embodiments, cationic shampoos comprise cationic guar gum, optionally having charge density of from about 0.8 to about 7 meq/g and a molecular weight (MW) of from about 5,000 to about 10 million Daltons. When used in connection with polymers (including pre-polymers) which may be supplied as populations of mildly diverging molecules (e.g., having a slightly different number of repeating units, such as siloxane units for some silicone pre-polymers), the term molecular weight relates to the weighted or weight average MW, unless indicated otherwise by the supplier. The weight average MW can be measured by gel permeation chromatography.

In some embodiments, the coloring is reversible (also referred to as decoloring) by use of a solution for removal of the coloring composition (also referred to as a removal solution or decuring solution), comprising a silicone decuring agent, for example, (a) a fluoride salt such as TBAF (tetra butyl ammonium fluoride) and RonaCare® Olaflur; or (b) an organic acid such as DBSA (dodecyl benzene sulfonic acid); or (c) an organic or inorganic base (and salts thereof) such as TBAH (tetra butyl ammonium hydroxide), TBAB (tetra butyl ammonium bromide), TBAC (tetra butyl ammonium chloride), potassium hydroxide (KOH) and potassium tert-butoxide (K(CH$_3$)$_3$CO)). In some embodiments, TBAB or TBAC are used in combination with an inorganic base, and in particular embodiments the additional base can be KOH, NaOH, LiOH, Mg(OH)$_2$, or Ca(OH)$_2$. In one embodiment, the decuring agent can be formed by combining an organic salt (e.g., hydroxyethyl cetyldimonium phosphate, such as commercialized by BASF under tradename Luviquat® Mono CP AT1) and an inorganic base (e.g., magnesium hydroxide).

Additional fluoride salts which can serve as decuring agents include, but are not limited to, ammonium fluoride, octadecenyl-ammonium fluoride, 3-(N-hexadecyl-N-2-hydroxy-ethylammonio) propylbis (2-hydroxyethyl) ammonium difluoride, ammonium monofluorophosphate, calcium fluoride, calcium monofluorophosphate, magnesium fluoride, potassium monofluorophosphate, sodium fluoride, sodium monofluorophosphate, N,N',N'-Tris(polyoxyethylene)-N-hexadecyl-propylenediamine dihydrofluoride, and nicomethanol hydrofluoride. Such decoloring is believed to be triggered by the decuring of the at least partially cured film formed by the amino-silicone elastomer on the surface of the keratinous fibers. Without wishing to be bound by any particular theory, the decuring is believed to loosen the bonds formed between the amino-silicone units constituting the cured film and/or its attachment to the fibers. In some embodiments, the decoloring of the fibers colored according to the present teachings is achieved by applying a decuring solution including a silicone decuring agent in an amount sufficient to at least partially decure the cured pigmented film so as to detach it from the fibers by subsequent rinsing.

When the silicone decuring agent is a fluoride salt, a suitable amount can be expressed in terms of fluoride content per total weight of the decuring solution. In such embodiments, a fluoride content of the agent is in an amount of at least about 0.01 wt. % and of at most 1 wt. %, per weight of the silicone decuring solution.

Alternatively, and in particular when the silicone decuring agent is an organic acid or an organic or inorganic base, the agent can be suitably present in an amount of at least about 0.1 wt. % and of at most about 15 wt. %, per total weight of the silicone decuring solution, or in the range of from about 0.5-10 wt. % or in the range of from about 0.5-5 wt. %.

In some embodiments, silicone decuring agents can be combined with one another or with other decuring promoting agents. By way of example, a fluoride salt can be present in the decuring solution in combination with a base (optionally an organic base including an amine group which can by itself serve as decuring agent). Such combinations of decuring agents may result in additive or synergistic effects further facilitating or accelerating the removal of the cured pigmented film from the keratinous fibers.

In some embodiments, the decuring solution is prepared by dispersing or dissolving the decuring agent(s) in a solvent which can be (a) an aqueous solvent which may optionally further comprise one or more water-miscible co-solvents and/or one or more dispersants; or (b) an organic solvent optionally comprising one or more dispersants.

In some embodiments, the decuring solution is prepared by dispersing or dissolving the decuring agent(s) in a solvent which can be at least one of (i) a dipolar aprotic solvent, having high polarity and low reactivity; (ii) a non-polar aprotic solvent, which does not readily donate a proton, and does not have polar groups; (iii) a polar aprotic solvent, containing a polar group (e.g., ether, ketone, ester); and (iv) a protic solvent, containing a labile H$^+$ that can be readily donated.

In some embodiments, fluoride salts decuring agents of group (a) described above can be dispersed or dissolved in dipolar aprotic solvents. Suitable dipolar aprotic solvents can be selected from the group comprising acetonitrile (ACN), propionitrile, N-octyl pyrrolidone (NOP) and dimethyl sulfoxide (DMSO). In some embodiments, organic acids and organic bases decuring agents of respective groups (b) and (c) described above can be dispersed or dissolved in polar aprotic solvents. Suitable polar aprotic solvents can be selected from the group comprising methyl isobutyl ketone (MIBK), methyl phenyl ester (MPE), tetrahydrofuran (THF), 1,4 dioxane, anisole and ethyl hexyl stearate.

Organic acids decuring agents of the group (b) described above, can alternatively be dispersed or dissolved in non-polar aprotic solvents. Suitable non-polar aprotic solvents can be selected from the group comprising dodecane, toluene, and xylene. In some embodiments, organic bases and inorganic bases decuring agents of group (c) described above can be dispersed or dissolved in protic solvents. Suitable protic solvents can be selected from the group comprising of water, primary, secondary and tertiary $C_1$-$C_6$ alcohols, including glycerol, butanol, isopropanol, cyclohexanol and $C_4$-$C_{16}$ fatty alcohols, including tert-butyl alcohol and myristyl alcohol.

When the removal solution comprises about 50 wt. % or more of water, in addition to the aforesaid solvents or mixtures thereof, the composition is said to be an aqueous removal solution, as opposed to an organic removal solution in a contrary situation (<50 wt. % of water, including devoid of water). In embodiments wherein the decuring agent(s) are dispersed or dissolved in a mixture of water and organic solvent(s), the weight per weight ratio of the water to the organic solvent(s) is typically in the range of from about 1:9 to about 9:1. It is to be noted that while the addition of water may increase compliance, it may also prolong the duration of the removal process.

The decoloring or decuring solution is applied for a time period sufficient to at least partially decure the cured film, the application of the decuring agent for a sufficient time being followed by rinsing away the decured silicone with an aqueous rinse. The amount of time that may suffice to decure enough of the film so as to permit its removal may depend, among other things, on the concentration of the decuring agent, the viscosity of the decuring solution, the temperature of the decuring process, the type of the keratinous fibers, the thickness of the cured film, the relative humidity, and any such factors readily appreciated by the skilled person.

In some embodiments, the decuring solution is applied at a temperature in the range of at least ambient temperature of at least about 18° C. to at most about 40° C., at most about 38° C., at most about 36° C., at most about 34° C., or at most about 32° C. In the experimental section herein, ambient temperature, unless otherwise indicated, generally refers to about 23° C. Ambient relative humidity (RH), unless controlled, hence otherwise indicated, is between about 60% RH and about 80% RH. Ambient pressure is typically of about 1 atmosphere.

In some embodiments, the decuring solution is applied for a time period between about 1 minute and about 30 minutes, between about 2 minutes and about 20 minutes or between about 5 minutes and about 10 minutes.

Suitably the viscosity of the silicone decuring solution is sufficient for the solution to coat the fibers and remain thereon for a duration of time enabling the partial decuring, hence the subsequent film removal and decoloring of the fibers. In some embodiments, this viscosity is achieved by further adding to the decuring agent in its solvent, a thickening agent in an amount sufficient to provide said viscosity.

Following the application of the decoloring solution, the fibers are thoroughly washed with an aqueous rinsing agent, the last rinsing being optionally followed by shampooing of the fibers with a shampoo.

In some embodiments, no bleaching is needed during the coloring process. In some embodiments, the compositions according to the present teachings are substantially devoid of bleaching agents. Bleaching agents traditionally include at least oxidizing agent chosen from persulfates, perborates, percarbonates, peracids, bromates, their salts and mixtures thereof, which can be optionally applied with hydrogen peroxide, all generally in an amount of at least about 10% by weight of a bleaching composition. As used herein, a composition is substantially devoid of bleaching agent(s), if such agent (or mixture thereof) is to be found at about 1 wt. % or less of the composition, or at less than about 0.5 wt. %, or at less than about 0.1 wt. %.

The compositions disclosed herein, in at least some embodiments, may be used in a single-step coloring process, in contrast to known hair coloring compositions, which typically requires a two-step oxidation process In some embodiments, subsequent coloration requires coloration only of the hair roots.

The compositions disclosed herein, in at least some embodiments, show improved resistance to discoloration by external agents and factors, as compared to known coloring agents. In some embodiments, the cured pigmented films can resist fading when exposed to light (e.g., maintaining original color for longer periods of time when exposed to sun radiation), and the compositions are said in such cases to have or provide good lightfastness. In some embodiments, the cured pigmented films can resist bleaching, and the compositions are said in such cases to have or provide good chemical resistance, bleach being a relatively harsh agent deemed predictive of resistivity to milder chemical exposures, such as encountered for example in polluted environments or at a swimming pool.

The compositions disclosed herein, in at least some embodiments, provide improved aesthetic properties of keratinous fibers, such as improved appearance, increased volume, softness, smoothness and shine.

The term "reactive amino-functional silicone" (also referred to herein as "reactive condensation-curable amino-functional silicone pre-polymer" and such variants, in accordance with the present disclosure is an organosilicon pre-polymer which contains at least two silanol groups and/or hydrolysable reactive groups, like alkoxy groups, which upon hydrolysis form silanol groups, and at least one carbon bonded amine group in its molecule, said alkoxy radicals, when present, each independently having 1-6 or 1-4 carbon atoms.

Organosilicon pre-polymers include repeats of siloxane units (—O—Si—) the silicone atom of the siloxane repeats being further substituted as herein detailed. Amino-silanes are one example of low MW amino-silicones having one, two or at most three atoms of silicon substituted by alkoxy or hydroxyl groups. As a rule, amino-silanes serve as cross-linking agents and are used in the present disclosure in combination with amino-silicone pre-polymers or with amino-silicone oils having at least 4 atoms of silicon, at least 10 atoms of silicon, or at least about 15 atoms of silicon. The present inventors have observed that an amino-silicone composition consisting exclusively or almost exclusively of amino-silanes having up to 3 atoms of silicones yield a brittle coat unpleasant to the touch and easily breaking away from the hair surface, even when forming relatively thin films.

It is believed that silicone molecules having only one reactive group cannot enable formation of a satisfactorily cross-linked elastomer, if at all. While silicone molecules having two reactive groups increase the probability of forming a sufficiently cross-linked elastomer, contributing for instance to the coupling of two molecules of pre-polymer, it is believed that a composition consisting predominantly or exclusively of such "bireactive" pre-polymers may only enable linear chain extension or at most entanglement, given time. Without wishing to be bound by any particular theory, it is believed that the cohesivity of an amino-silicone film according to the present disclosure is improved by increasing the density of cross-linking between distinct molecules of pre-polymers. Advantageously, such cross-linking forms a 3D network. In a preferred embodiment, the pre-polymer contains at least three silanol groups and/or hydrolysable reactive groups able to form silanol moieties upon hydrolysis. Additionally, the composition being applied on the hair fibers comprise condensation-curable amino-silicone pre-polymers having at least about 4 atoms of silicon. Alternatively, the 3D network can be formed with bireactive pre-polymers in presence of cross-linkers having at least three silanol groups and/or hydrolysable reactive groups able to form silanol moieties upon hydrolysis.

The term "reactive group" is understood to mean any group capable of forming a covalent bond with another polymeric backbone or with a cross linker at least by way of condensation curing. Examples of reactive groups on a reactive condensation-curable amino-silicone are:

—$C_1$-$C_6$ or $C_1$-$C_4$ alkoxy group, such as methoxy, ethoxy, propoxy, isopropoxy, or methoxyethoxy groups; or Hydroxyl group, such as silanol functional; or Acyloxy groups or aryloxy groups; or Oxime groups, such as methylethylketoxime.

The amino functional group can be:

Primary amine (I) groups, such as aminoalkyl groups,

Secondary amine (II) groups, such as aminoethylaminopropyl group, which can be located in the amino-silicone pre-polymer chain at terminal position or as side chain (pendant); or Tertiary (III) amino group, such as in N,N-dialkylaminopropyl group, which are typically located in branched amino-silicone polymer chain.

The amino-silicone pre-polymer can have one or more amine reactive groups, and be accordingly referred to as a monamino, diamino, triamino, tetramino and so on, amino-silicone.

As mentioned, the amino groups are further capable of reacting though curing processes other than condensation curing.

Additionally, the functional amines can be used as catalysts to promote condensation curing of alkoxy groups as found, for example, in amine/alkoxy functional silicones.

Cross-linking agents suitable for the polymerization of such condensation-curable pre-polymers may comprise similar reactive groups, and be for instance condensation-curable amino-silicone monomers (e.g., amino-silanes). Cross-linking agents may display only amino functional groups, or additional reactive groups, such as aliphatic carbon moieties, vinyl, allyl, mercapto, epoxy, acrylate or methacrylate functional groups.

Cross-linking may be catalyzed using additional organic amines species or amino functional silicone for better compatibility with the reactive amino functional silicone pre-polymer.

Curing accelerators suitable for the cross-linking of these condensation-curable oligomers or polymers include carbodiimides (R—N=C=N—R') catalysts, such as diisoprylcarbodiimide and preferably multifunctional polycarbodiimides, such as commercially available under the trade name of Carbodilite from Nisshinbo Chemical Inc., Japan. Additionally, amino-silicone oils can act as condensation-curing accelerators thanks to the presence of amine moieties, in addition to any other function they can fulfil in the composition.

Curing accelerators (other than amino-silicone oils) can typically be present in the curable composition, in relatively low amount not exceeding 5% by total weight of the composition, or in less than about 2 wt. %, less than about 1 wt. % or less than about 0.5 wt. %.

Cross-linking may alternatively and additionally be further favored by adding to the composition a solid inorganic filler selected and adapted to facilitate and/or accelerate the curing of the condensation-curable film-forming amino-silicone pre-polymers. Such a film reinforcing filler can also be referred to as a reactive filler. Advantageously, the reactive reinforcement filler is a hydrophobic 3D network former contributing to the increase in cohesivity of the amino-silicone film.

Reinforcement fillers can generally be selected from the group of fumed silica, precipitated silica, magnesia, alumina (e.g., $Al_2O_3.3H_2O$), black, amorphous, carbon (carbon black, channel black, or lamp black). The reinforcement filler can be selected to suit a particular coloration. For instance, if a reinforcement filler is desired in a relatively high quantity, then black fillers are to be avoided if in a size range that may affect a relatively light shade.

Suitable reactive fillers can be selected from hydrophobic fumed silica, the surface of which being at least partially covered by siloxane groups or other groups having a hydrophobic nature, such groups typically reacting with silanol functional units on the silica. Hence, in such cases, the hydrophobic fumed silica can be referred to as a silanol blocked silica, the surface treatment of the fumed silica blocking the silanol functionalities being achieved by one or more of HDMS, poly siloxane, cyclic poly siloxane, silazane, amino silane and silicone oils. The blocking treatment needs not to be complete, some residual silanol groups being permissible and even desirable for ensuring or facilitating at least partial curing. Hydrophobic fumed silica, when present, is typically disposed in the oil phase of the oil-in-water emulsion of condensation-curable silicone.

The term "non-reactive group" is understood to mean any group that is not capable of forming a covalent bond with another polymer backbone or with a cross linker. Examples of non-reactive groups are saturated $C_1$-$C_6$ or $C_1$-$C_4$ alkyls, such as a methyl group, or any other group unable to undergo hydrolysis or any other chemical transformation enabling the formation of a covalent bond with another amino-silicone pre-polymer.

The compositions according to the present teachings may comprise in addition to the "reactive silicones" including the condensation-curable amino-silicone pre-polymers and, if applicable, silicone-based cross-linkers able to actively participate in the formation of a cured amino-silicone film, non-reactive silicone compounds (e.g., silicone oils or silicone molecules only including non-reactive groups or cross-linked silicone resins). In some embodiments, the reactive silicones are present in a weight percentage of at least about 50% by total weight of the silicone materials (both reactive and non-reactive). In other embodiments, the reactive silicones constitute at least about 60 wt. %, at least about 70 wt. %, or at least about 80 wt. % of the total weight of all silicone materials.

According to a further aspect, there is disclosed a coating composition for forming an amino-silicone coating on an external surface of individual hairs of mammalian hair, the coating composition being an oil-in-water emulsion comprising:

(A) an aqueous phase containing water; and
(B) an oil phase including at least one reactive condensation-curable film-forming amino-silicone pre-polymer;

wherein said oil phase fulfills at least one of the following:
(i) said at least one reactive condensation-curable film-forming amino-silicone pre-polymer includes at least one reactive condensation-curable film-forming amino-silicone monomer having a molecular weight of at most about 1000 g/mol;
(ii) said oil phase further contains a non-amino cross-linking agent adapted or selected to cure said pre-polymer, said non-amino cross-linking agent having a molecular weight of at most about 1000 g/mol;
wherein said at least one reactive condensation-curable film-forming amino-silicone pre-polymer has a solubility in water of less than about 1% by weight at about 25° C.

According to a further aspect, there is disclosed a coloring composition for forming a pigmented amino-silicone coating on an external surface of individual hairs of mammalian hair, the coloring composition being an oil-in-water emulsion comprising:
(A) an aqueous phase containing water; and
(B) an oil phase including at least one reactive condensation-curable film-forming amino-silicone pre-polymer and a plurality of sub-micronic pigment particles;
wherein said oil phase fulfills at least one of the following:
(i) said at least one reactive condensation-curable film-forming amino-silicone pre-polymer includes at least one reactive condensation-curable film-forming amino-silicone monomer having a molecular weight of at most about 1000 g/mol;
(ii) said oil phase further contains a non-amino cross-linking agent adapted or selected to cure said pre-polymer, said non-amino cross-linking agent having a molecular weight of at most about 1000 g/mol;
(iii) said plurality of sub-micronic pigment particles are dispersed in said oil phase in presence of a pigment dispersant;
wherein said at least one reactive condensation-curable film-forming amino-silicone pre-polymer has a solubility in water of less than about 1% by weight at about 25° C.

According to a further aspect, there is disclosed a hair masking composition for forming an amino-silicone hair masking coating on an external surface of individual hairs of mammalian hair, the hair masking composition being an oil-in-water emulsion comprising:
(A) an aqueous phase containing water; and
(B) an oil phase including at least one reactive condensation-curable film-forming amino-silicone pre-polymer;
(C) a plurality of metallic pigments;
wherein said oil phase fulfills at least one of the following:
(i) said at least one reactive condensation-curable film-forming amino-silicone pre-polymer includes at least one reactive condensation-curable film-forming amino-silicone monomer having a molecular weight of at most about 1000 g/mol;
(ii) said oil phase further contains a non-amino cross-linking agent adapted or selected to cure said pre-polymer, said non-amino cross-linking agent having a molecular weight of at most about 1000 g/mol;
wherein said at least one reactive condensation-curable film-forming amino-silicone pre-polymer has a solubility in water of less than about 1% by weight at about 25° C.

According to a further aspect, there is disclosed an amino-silicone coating removal composition at least one of A): one or more decuring solvents selected of (i) a dipolar aprotic solvent, having high polarity and low reactivity; (ii) a non-polar aprotic solvent, which does not readily donate a proton, and does not have polar groups; (iii) a polar aprotic solvent, containing a polar group; and (iv) a protic solvent, containing a labile H$^+$ that can be readily donated; and B) one or more decuring agents selected from: (a) a fluoride salt, such as TBAF (tetra butyl ammonium fluoride) and RonaCare® Olaflur; (b) an organic acid such as DBSA (dodecyl benzene sulfonic acid); and (c) an organic or inorganic base (and salts thereof) such as TBAH (tetra butyl ammonium hydroxide), TBAB (tetra butyl ammonium bromide), TBAC (tetra butyl ammonium chloride), potassium hydroxide (KOH) and potassium tert-butoxide ($K(CH_3)_3CO$)).

Clauses

1. A method of cosmetically treating an external surface of mammalian hair, as herein described, wherein prior to the application of an oil-in-water emulsion according to the present teachings, and optionally following a degreasing step, if performed, applying, on the external surface of the individual hairs, a film-forming hair masking binder formulation so as to produce a polymeric film on the hair.

2. The method according to clause 1, wherein the film-forming hair masking binder formulation further includes (i) a plurality of sub-micronic organic or inorganic pigment particles, and/or (ii) pigment particles, including pigment flakes, so as to produce a tinted binder polymeric film on the external surface of the individual hairs or on top of a previously laid-down film on the hair.

3. The method according to clause 1 or clause 2, wherein the film-forming hair masking binder formulation comprises a reactive condensation-curable amino-silicone elastomer, a cross-linking agent, an emulsifier and an optional catalyst emulsified in an aqueous carrier.

4. The method according to any one of clause 1 to clause 3, further comprising, after A) applying the film-forming hair masking binder formulation:
B) allowing the film-forming binder to preliminarily cure;
C) washing the hair with a rinsing liquid to leave a preliminarily cured polymeric film on the external surface of the individual hairs, the film being optionally tinted;
D) applying to the preliminarily cured film a flake dispersion including of a plurality of pigment flakes, a dispersant and an aqueous carrier;
E) washing the fibers with a rinsing liquid to leave a layer of metallic-looking pigment flakes on and adhering to the preliminarily cured film.

5. The method according to any one of clause 2 to clause 4, wherein the pigment flakes are metallic pigment flakes containing, coated with, consisting essentially of, or made of metals, alloys and oxides thereof, said flakes being selected from the group comprising aluminum flakes, brass flakes, bronze flakes, copper flakes, gold flakes, mica coated flakes, silica coated flakes and silver flakes.

6. The method according to any one of clause 2 to clause 5, wherein the pigment flakes are further coated with a coupling agent capable of covalently binding the reactive amino-silicone elastomer of the film-forming hair masking binder formulation.

7. The method according to clause 6, wherein the coupling agent is a cosmetically acceptable coupling agent selected from the group including acrylate coupling agents, thiol coupling agents, anhydride coupling agents, epoxy coupling agents, and silanol coupling agents.

8. The method according to any one of clause 2 to clause 7, wherein the pigment flakes are charged at a polarity opposite a polarity of the preliminarily cured hair masking film.

9. The method according to any one of the preceding clauses, further comprising, subsequent to at least partially condensation curing of pigmented film, applying a clear protective coating, the protective coating including an amino-silicone elastomer, a cross-linking agent, an emulsifier and an optional catalyst emulsified in an aqueous carrier.

10. A method for removing an amino-silicone coating from an external surface of individual hair fibers, said coating comprising at least one of an amino-silicone prepolymer and an amino-silicone polymer, the method comprising applying a decuring solution for a time period sufficient to at least partially decure the amino-silicone coating, the application of the decuring solution for a sufficient time being followed by rinsing away the decured coating.

11. The method according to clause 10, wherein the decuring solution includes at least one decuring solvent selected of (i) a dipolar aprotic solvent, having high polarity and low reactivity; (ii) a non-polar aprotic solvent, which does not readily donate a proton, and does not have polar groups; (iii) a polar aprotic solvent, containing a polar group; and (iv) a protic solvent, containing a labile H$^+$ that can be readily donated.

12. The method according to clause 11, wherein the decuring solution further includes at least one decuring agent.

13. The method according to clause 12, wherein the at least one decuring agent is a fluoride salt selected from the group comprising TBAF (tetra butyl ammonium fluoride), ammonium fluoride, octadecenyl-ammonium fluoride, 3-(N-hexadecyl-N-2-hydroxy-ethylammonio) propylbis (2-hydroxyethyl) ammonium difluoride, ammonium monofluorophosphate, calcium fluoride, calcium monofluorophosphate, magnesium fluoride, potassium monofluorophosphate, sodium fluoride, sodium monofluorophosphate, N,N',N'-Tris(polyoxyethylene)-N-hexadecyl-propylene-diamine dihydrofluoride, nicomethanol hydrofluoride and RonaCare® Olaflur; said decuring agent being present in the decuring solution in an amount of at least 0.01 wt. % and of at most 1 wt. %, expressed in terms of fluoride content, per total weight of the decuring solution.

14. The method according to clause 13, wherein the at least one fluoride salt is dispersed or dissolved in a dipolar aprotic solvent selected from the group comprising acetonitrile (ACN), propionitrile, N-octyl pyrrolidone (NOP) and dimethyl sulfoxide (DMSO).

15. The method according to clause 12, wherein the at least one decuring agent is (a) an organic acid such as an organic sulfonic acid (including DBSA (dodecyl benzene sulfonic acid)); and/or (b) an organic or inorganic base (and salts thereof) such as TBAH (tetra butyl ammonium hydroxide), TBAB (tetra butyl ammonium bromide), TBAC (tetra butyl ammonium chloride), potassium hydroxide (KOH) and potassium tert-butoxide ($K(CH_3)_3CO$)); the at least one decuring agent being present in the decuring solution in an amount of at least 0.1 wt. % and of at most 15 wt. %, per total weight of the silicone decuring solution.

16. The method according to clause 15, wherein said at least one decuring agent is an organic acid dispersed or dissolved in at least one of (a) a polar aprotic solvents selected from the group comprising methyl isobutyl ketone (MIBK), methyl phenyl ester (MPE), tetrahydrofuran (THF), 1,4 dioxane, anisole and ethyl hexyl stearate; and (b) in non-polar aprotic solvents selected from the group comprising dodecane, toluene, and xylene.

17. The method according to clause 15, wherein said at least one decuring agent is an organic base dispersed or dissolved in at least one of (a) a polar aprotic solvents selected from the group comprising methyl isobutyl ketone (MIBK), methyl phenyl ester (MPE), tetrahydrofuran (THF), 1,4 dioxane, anisole and ethyl hexyl stearate; and (b) a protic solvent selected from the group comprising water, primary, secondary and tertiary $C_1$-$C_6$ alcohols, including glycerol, butanol, isopropanol, cyclohexanol and $C_4$-$C_{16}$ fatty alcohols, including tert-butyl alcohol and myristyl alcohol.

18. The method according to any one of clause 10 to clause 17, wherein said decuring, solution contains less than 90 wt. % of water.

19. The method according to any one of clause 10 to clause 18, wherein said decuring solution further comprises at least on of a dispersant and a thickener.

20. The method according to any one of clause 10 to clause 19, wherein the decuring solution is a applied on an amino-silicone coating obtained by a method according to the present teachings.

21. The method according to any one of clause 10 to clause 20, wherein the time period sufficient to at least partially decure the amino-silicone coating if of 30 minutes or less, 20 minutes or less, or 10 minutes or less.

22. The method according to any one of clause 10 to clause 21, wherein the decuring solution is applied at a temperature in the range of from about +15° C. to about +40° C.

BRIEF DESCRIPTION OF THE DRAWINGS

The present disclosure will hereinafter be described in conjunction with the following drawing figures, wherein like numerals denote like elements, and:

Some embodiments of the present disclosure are described herein with reference to the accompanying figures. The description, together with the figures, makes apparent to a person having ordinary skill in the art how some embodiments of the present disclosure may be practiced.

The figures are for the purpose of illustrative discussion and no attempt is made to show structural details of an embodiment in more detail than is necessary for a fundamental understanding of the present disclosure. For the sake of clarity, some objects depicted in the figures are not to scale.

Figure 1A:
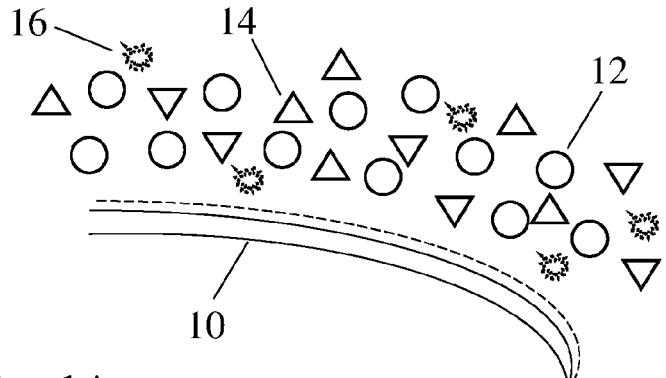
Figure 1A:
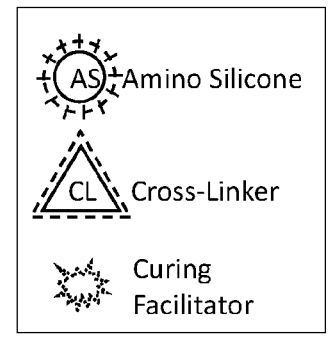
Figure 1B:
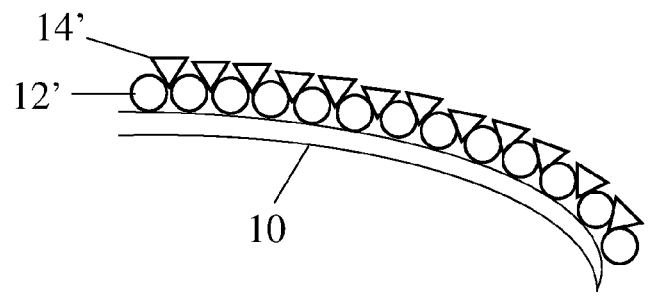
Figure 1C:
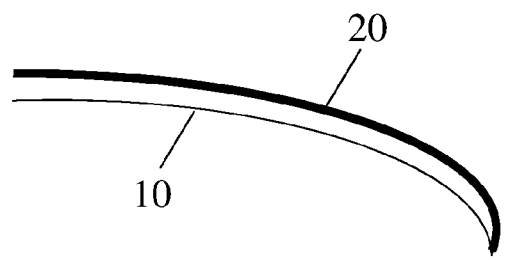
Figure 1D:
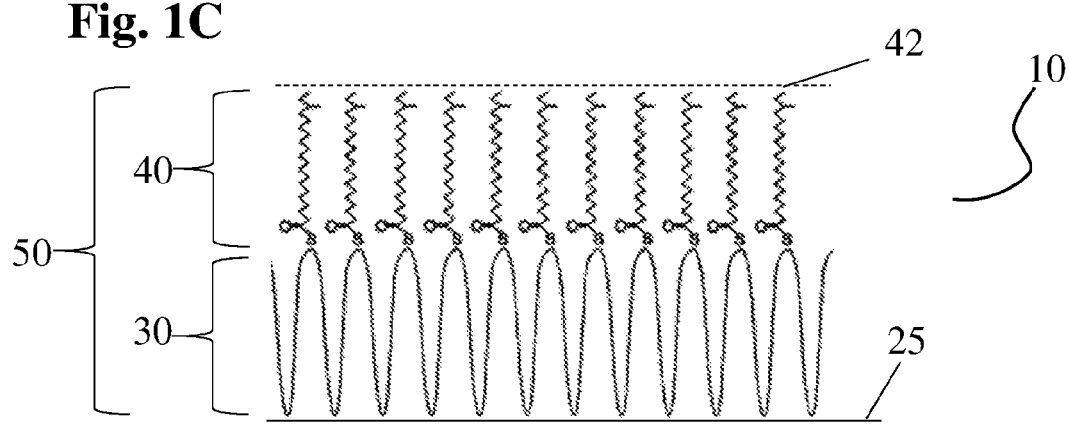
Figure 2A:
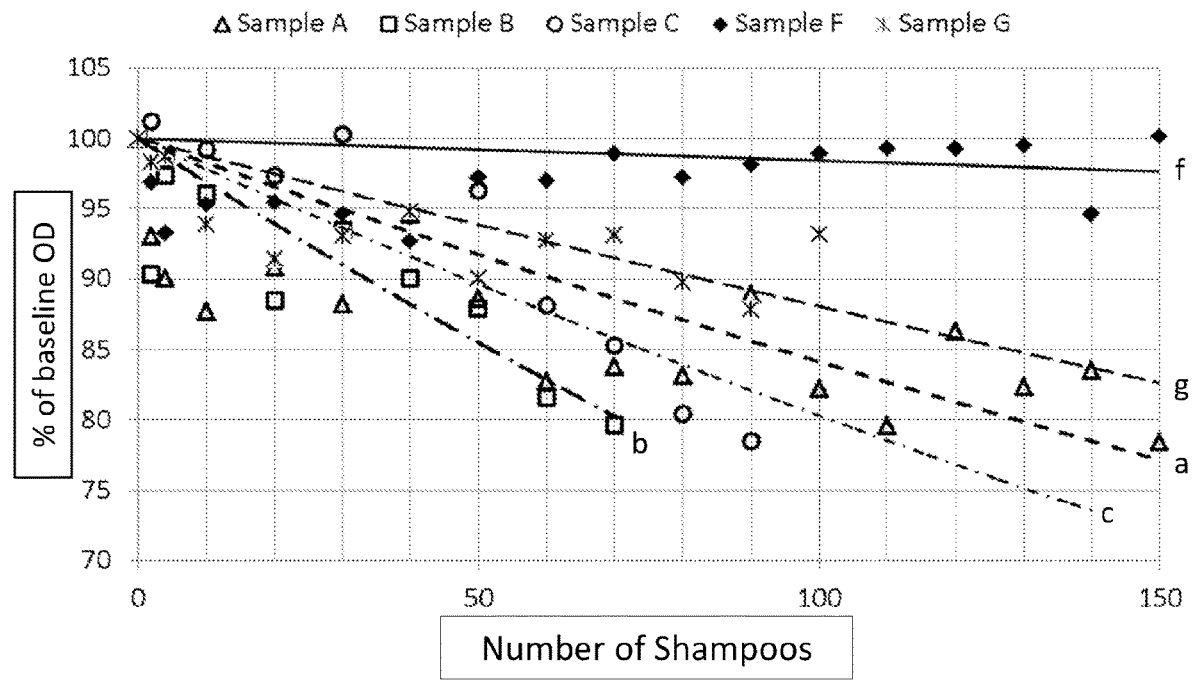
Figure 2B:
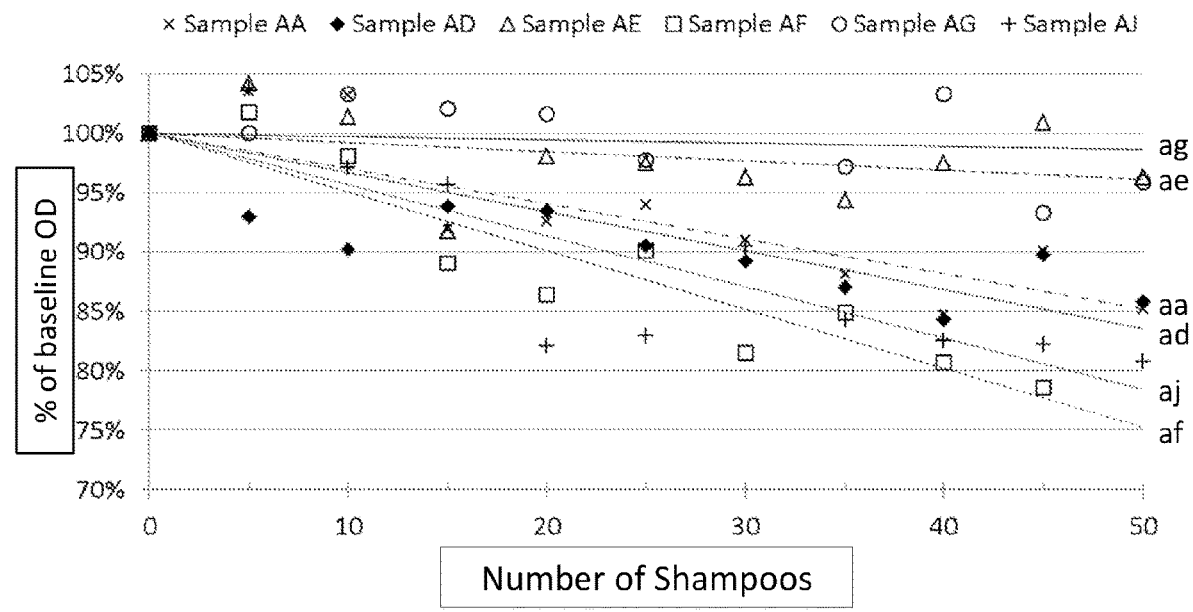
Figure 4A:
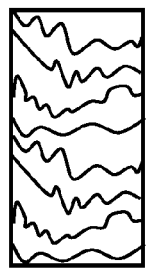
Figure 4B:
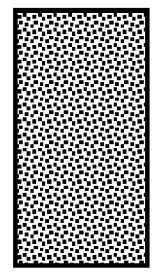

In the Figures:

FIG. 1A is a schematic illustration of a single keratinous fiber in presence of some of the dispersed components constituting a coloring formulation (pigments being omitted);

FIG. 1B is a schematic illustration representing how some of the components of FIG. 1A can migrate towards the fiber and arrange thereupon;

FIG. 1C schematically shows how the components may coalesce to form a continuous film on the external surface of the fiber;

FIG. 1D schematically illustrates the structure of mammalian hair at enlarged scale;

FIG. 2A is a graph showing the percentage of baseline OD value as a function of the number of shampooing and drying treatments to which a hair tuft is subjected for samples A, B, C, F and G;

FIG. 2B is a graph showing the percentage of baseline OD value as a function of the number of shampooing and drying treatments to which a hair tuft is subjected for samples AA, AD, AE, AF, AG and AJ;

FIGS. 3A to 3F are confocal laser scanning microscope images of Chinese black human hair coated with a composition J according to the principles of the present disclosure following 0 (A-C) and 30 (D-F) shampooing and drying treatments, panels A and D showing ×20 magnified views, panels B and E showing ×50 magnified views and panels C and F showing ×100 magnified views;

FIG. 4A is a schematic illustration of the external surface of a native hair fiber displaying hair scales;

FIG. 4B is a schematic illustration of the external surface of a hair fiber coated with sub-micronic pigments or with pigment flakes according to the present teachings; and FIGS. 4C to 4F are confocal laser scanning microscope images at ×100 magnification of (C) native uncoated yak hair, (D) yak hair coated with a coloring composition according to one embodiment of the present disclosure (sub-micronic Hostaperm Blue 15:3), (E) yak hair treated as in panel D subjected to a decoloring solution including TBAF, and (F) yak hair treated as in panel D subjected to a decoloring solution including DBSA.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure relates to compositions for coloring or cosmetically treating keratinous fibers, including mammalian hair such as human or animal hair, and more particularly to compositions comprising a reactive condensation-curable amino-silicone pre-polymer and an insoluble pigment, the composition being in an aqueous medium. Methods of preparing and using the same and kits enabling such coloring are also described. The present disclosure encompasses the coloring of mammalian fibers when attached to a living subject and when isolated therefrom, for instance for the cosmetic treatment of wigs, or any other keratinous fibers detached from their subject of origin.

In some embodiments, the pigments for the compositions, kits and methods according to the present teachings, whether sub-micronic organic pigments, sub-micronic inorganic pigments, metallic-looking pigments and the like, as detailed herein, are not only insoluble in water or organic solvents, but additionally insoluble in the reactive condensation-curable amino-silicone pre-polymer, in the reactive oil phase wherein it is disposed and/or in the resulting elastomer.

According to some embodiments, there is provided a method of coloring an external surface of keratinous fibers (e.g., mammalian hair), the fibers in one embodiment attached to a body of a mammalian subject (e.g., a human subject), the method comprising:
(a) applying, on the external surface of individual fibers (e.g., individual hairs of the mammalian hair), a formulation comprising:
(i) water;
(ii) a reactive condensation-curable film-forming amino-silicone pre-polymer that, subsequent to condensation curing, forms an elastomer;
(iii) a plurality of sub-micronic organic or inorganic pigment particles;
(iv) a dispersant for dispersing the sub-micronic pigment particles in the formulation; and optionally,
(v) a cross-linking agent adapted to cure said at least one pre-polymer;
(vi) a hydrophobic reactive filler adapted to cure said at least one pre-polymer;
(b) after enabling said partial condensation curing to ensue, to form an at least partially cured film on the external surface of the individual hairs, washing the fibers with a rinsing liquid to leave said pigmented, at least partially cured film on the external surface of the individual fibers.

Kit comprising formulations suitable for implementing the present methods are also disclosed.

According to some other embodiments, there is provided a kit for treating an external surface of keratinous fibers (e.g., mammalian hair optionally attached to a mammalian subject), the kit comprising:
(a) a first compartment containing a pigmented formulation including:
(i) a reactive condensation-curable film-forming amino-silicone pre-polymer;
(ii) a dispersed plurality of sub-micronic organic or inorganic pigment particles;
(iii) a dispersant; and optionally
(iv) a silicone oil miscible with said film-forming amino-silicone pre-polymer;
(b) a second compartment containing water and an emulsifier to form an emulsion when mixed with the content of the first compartment;
(c) a third compartment, said third compartment containing a cross-linking agent and optionally a silicone oil miscible with said cross-linking agent;
(d) a compartment containing water and an emulsifier to form an emulsion when mixed with the content of the third compartment, wherein the compartment of (d) is a fourth compartment or said second compartment.

In some embodiment, the kit may further comprise an additional compartment consisting of a reactive filler and a non-reactive silicone oil, the reactive filler being dispersed therein.

In some embodiment, the kit may further comprise one or more of the following:
i) an applicator for applying any of the formulations according to the present teachings or combinations thereof to the external surface of the keratinous fibers;
ii) a thermometer for monitoring a temperature of any of said formulations or combinations thereof;
iii) a timer for monitoring a duration of application of any of said formulations or combinations thereof to the external surface of the keratinous fibers;
iv) a cationic shampoo for use, if desired, at least until the reactive condensation-curable amino-silicone elastomer of the pigmented formulation fully cures onto the keratinous fibers;
v) a leaflet guiding a user of the kit on the use of each formulation, including combinations thereof when applicable.

Without wishing to be bound by any particular theory, it is believed that FIGS. 1A-1C schematically illustrate the principles underlying a portion of one aspect of the method of the present disclosure. FIG. 1A shows a schematic illustration of a single keratinous fiber 10 in the presence of some of the dispersed components constituting a coloring or coating formulation (e.g., oil-in-water emulsion) as herein disclosed. The reactive condensation-curable amino-functional silicone pre-polymer (or micelles or emulsion droplets containing the same) 12 is represented by circles. The cross-linking agents capable of cross-linking the curable amino-silicone elastomer (or micelles or emulsion droplets containing the cross-linking agent) 14 are represented by triangles. The optional cross-linking accelerator or catalyst, as well as the optional 3D network former (e.g., fumed silica), collectively referred to as curing facilitators (or micelles or emulsion droplets containing such curing facilitators) 16 are represented by stars. For clarity, the dispersant and pigment particles are not shown. For simplicity, all illustrated materials are displayed on a single side of the fiber. FIG. 1A is deemed to represent the situation upon initial exposure of the fibers to the condensation-curable amino-silicone formulation. In some embodiments, the keratinous fiber 10 is mammalian hair and its outer surface is negatively charged as shown in the figure. The hair surface shall be negatively charged when using a composition having a pH above the isoelectric point of the fibers (e.g., >4, preferably >7). In some embodiments, the reactive condensation-curable amino-functional silicone pre-polymer 12 is positively charged when dispersed in a carrier. For instance, amino-silicone pre-polymers can be positively charged as of a pH of 4.0 and until they reach their isoelectric point (typically in the range of pH 10-12). Interestingly, the protonation of the amine groups above the acidic pH (assuming a sufficient concentration) can maintain the composition within the basic pH range even in absence of a dedicated pH buffering agent. It is to be noted that at a relatively high pH (>9), hair scales are sufficiently charged to repulse one another, resulting in the opening of the channels leading to the hair shafts. The lifting of the scales increases the surface area of the hair fibers, enhancing contact surface with the emulsion of reactive amino-silicone pre-polymers. As carrier evaporates, the pH of the coat gradually decreases and the hair scales return to their original positions, possibly entrapping in the process a portion of the amino-silicone film, furthering its adherence to the hair by mechanical interlocking. In some embodiments, the cross-linking agent 14 (e.g., some non-amino materials) and/or the cross-linking facilitator 16 are each negatively charged when dispersed in a carrier.

FIG. 1B is a schematic macroscopic illustration representing how, with time, some of the components of FIG. 1A can migrate towards the fiber and arrange themselves thereupon. Such migration is believed to be electrostatically driven by the gradient of charge between the pre-polymers of the composition (e.g., positively charged at basic pH) and the surface of the hair fibers (e.g., negatively charged at a similar pH). Based at first on electrostatic interactions, the amino-silicone elastomer, micelles or emulsion droplets thereof (being in one embodiment positively charged) form a layer 12' on the surface of fiber 10 (being in the same embodiment conversely negatively charged). Similarly, the non-amino cross-linking agents, micelles or emulsion droplets thereof (being in the exemplified embodiment negatively charged, but not necessarily so as a rule) will form a layer 14' on the surface of layer 12' (being in the same embodiment conversely positively charged). For clarity, the optional curing facilitators shown as 16 in FIG. 1A, which would "intercalate" in layer 14', are omitted from FIG. 1B. Understandingly, according to these principles, anionic and nonionic polymers would not be subjected to such an electrostatic drive towards hair fibers, their prospective attachment therewith, if any, being accordingly reduced (e.g., allowing at most physical deposition or hydrophobic: hydrophobic interactions).

FIG. 1C schematically shows how, given further time, the components previously partially represented by 12, 14 and 16, coalesce, merge and/or react to form a continuous film 20 on the external surface of the fiber, so as to form an amino-silicone coated fiber. The coalescence of the oil droplets on the hair fibers is believed to force away the aqueous carrier towards the outer surface of the coated fiber, therefore facilitating its evaporation. Such a preliminary wetting of the fibers by the coloring compositions, according to the present teachings, is believed to be a pre-requisite for the entire coloring method. This step, at its beginning, may be herein referred to as "preliminary curing". With time, the amino-silicone elastomers of the film will cross-link with one another, the process proceeding towards full curing through a progressive phase of partial-curing. Without wishing to be bound by theory, it is believed that pre-polymers having a relatively low MW (a relatively low viscosity) have a better prospect to sufficiently wet the hair fiber than a pre-polymer having a relatively higher MW (a relatively higher viscosity). Hence, once the composition constituents are driven to be in sufficient proximity to the fiber thanks to electrostatic bonding, additional mechanisms, such as acid: base hydrogen bonding or even covalent bonding, may become available for the attachment of the amino-silicone molecules to the hair surface. Such processes, in combination with the ongoing condensation curing of the pre-polymer molecules are believed to provide (a) attachment ("adhesivity") to the underlying fiber and (b) "cohesivity" of the amino-silicone film.

While not shown in the figure, pigment particles applied in combination with amino-silicone compositions according to the present disclosure are advantageously entrapped within the growing network of the pre-polymers, the curing of which is completed in situ on the hair fiber. Such entrapment is believed to improve the attachment of pigment particles to the hair fibers and to ensure their retention thereon for a longer time period than affordable by mere physical deposition in presence of non-reactive polymers.

While not shown in the figure, it is believed that the film 20 formed according to the above described exemplary embodiment would be positively charged (e.g., under basic pH permitting the protonation of the amine moieties). A polymer is believed to be fully cured when, for instance, its glass transition temperature no longer changes over time, in other words has reached a substantially stable value, suggesting that no further cross-linking is taking place. Alternatively and additionally, an amino-silicone polymer would be fully cured, when the number of siloxane bonds it can form in the curable fluid and under the curing conditions applicable, does not substantially change over time. The number of siloxane bonds in a cured amino-silicone polymer can be assessed by routine analytical methods, such as by Fourier transform infrared (FTIR) spectroscopy.

As explained, the relative polarity of the fiber substrate to be coated or colored (e.g., a keratinous fiber, whether native, pre-treated, for instance by bleaching, or coated according to present teachings) and of the overall charge of the coloring or masking compositions due to treat the substrate (including the active constituents of these compositions) is believed to facilitate the initial wetting of the substrate by the compositions. Hence, in some embodiments, when a subsequent coating is desired, the subsequent composition can have a polarity opposite to the polarity of the coated substrate. Thus in the present illustration, if a negatively charged hair fiber is first coated with a pigmented amino-silicone film forming composition resulting in a positively charged film, the now positively charged substrate can be subsequently coated with an overall negatively charged subsequent composition. However, as opposite polarities are not essential, in alternative embodiments, subsequent coatings, if desired, can have similar polarity (positive or negative), the overall charge being similar or different.

It can be readily understood that the relative charge of the surface being coated and of the droplets or particles coating it form a gradient which decreases as the migration of the charged polymer-forming materials to the fiber proceeds. For illustrative example, assuming a negatively charged human hair and positively charged droplets of amino-silicone pre-polymers, at first there is a large gradient driving the positive droplets to the negative hair. As the hair gets coated with the positive droplets, its charge increases and therefore the gradient driving the surrounding droplets towards the fiber decreases until it is too small to drive any additional positively charged droplet to the hair. Without wishing to be bound by the above theory, it is believed that the process of the present method is self-terminating. The film is self-terminated as soon as the migration of the charged species reach a point where repulsion between the stationary layer on the hair fiber and the droplets of the bulk overcomes previous attraction.

This self-termination of the process, once there is no driving gradient any longer, advantageously prevents an endless build-up of material that conventionally lead to uncontrolled thickness of coatings. In extreme cases, the endless deposition of materials builds-up unseparable hair lumps of no practical use. In more tolerable situations, while the build-up of materials cannot be prevented, the coating can be interrupted and the hair fibers which have been liquid bridged in this undesired process can be individualized through often intense combing, such untangling process typically resulting in a poor appearance and/or weakened mechanical resistance/attachment of a color coating, if any. Advantageously, the self-terminating process according to the present teachings results in a coating of reasonable thickness, which allows the coated hair to remain separate in individual fibers and not stuck together. The thickness of the coat can be controlled via the size of the droplets of the emulsion (e.g., droplets having a $D_v50$ of from about 1-2 μm, as readily formed by vigorous manual shaking, will yield a coat of from about 0.5-1 μm thickness).

FIG. 1D is a schematic, magnified illustration representing a surface of a mammalian hair fiber 10 as provided in FIG. 1A. The exterior of the hair filament or fiber is made up of cuticle cells. These cells have multiple layers, the outward-most of which is the cell membrane complex 50. The cell membrane complex includes a dense protein matrix 30 attached to the outer surface 25 of the A-layer of the cuticle, and a lipid layer 40 having fatty acid chains attached at a first end (typically, but not exclusively, the fatty acid end) to protein matrix 30, and, at the opposite, free end, extending away from protein matrix 30. These fatty acid chains contribute to the hydrophobicity (and to the lubricity) of the hair.

The height of cell membrane complex 50 may be less than about 10 nm, typically about 5-7 nm. The inventors have observed that penetration through cell membrane complex 50, towards or to outer surface 25 of the A-layer of the cuticle, may be highly impeded for viscous materials, sterically-hindered materials or negatively-charged droplets, particularly in view of the narrow openings (circa 2 nm) between adjacent free ends of the fatty acid chains of cell membrane complex 50. The inventors believe that the various advantages of utilizing viscous polymeric materials notwithstanding, such materials may be significantly less suitable for achieving permanent hair coloring, with respect to their less viscous, monomeric and/or oligomeric counterparts.

Again, without wishing to be limited by theory, the inventors believe that for the pre-polymeric amino-silicone composition (e.g., liquid emulsion) according to the present teachings to appreciably contact the hydrophobic upper surface 42 of the fatty acid chains 40, the amino-silicone droplets need to be sufficiently hydrophobic. Moreover, this hydrophobicity aids in displacing the air disposed on the surface of the fatty acid chains 40, which is also required to enable penetration there-between.

The wetting process may be driven by charge interactions between the positively-charged amine moieties of the amino-silicone and various negatively-charged counterparts on the hair surface. Such drive can also be assessed by the gap in surface energy of the wetting liquid and the wetted surface. Amino-silicones having a surface energy of no more than the surface energy of the keratinous substrate are deemed advantageous. For instance, untreated, undamaged human hair typically has a surface energy of from about 24-28 milliNewton/meter (mN/m; also referred to as dyn/cm), while treated hairs are in the range of from about 38-47 mN/m.

Consequently, the Amine Number, or more generally, the charge density of the amino-silicone pre-polymer appears to be of particular importance. The Amine Number of an amino-silicone pre-polymer is generally supplied by the manufacturer, but can be independently determined by standard methods, as described for example in ASTM D 2074-07. It can be provided in terms of the amount of milliliters of about 0.1N HCl needed to neutralize about 10 g of the material under study.

This charge relationship, coupled with the requisite viscosity, surface tension and lack of steric hindrance of the amino-silicone pre-polymer, enables "pinning" of the pre-polymer within, or deeply within, the cell membrane complex 50. Such pinning may be grossly insufficient in terms of permanence, but allows at least partial curing of the pre-polymer (e.g., formation of a 3D network of siloxane cross-linking bonds in and around the protruding elements of the cell membrane complex 50).

According to some embodiments, the reactive condensation-curable amino-functional silicone pre-polymer has an average molecular weight in the range of from about 100 to about 100,000. Typically, a monomer has a MW in the range of from about 100 to about 600, an oligomer has an average MW in the range of from about 200 to about 2,000, and a polymer has an average MW of at least about 2,000, and in some embodiments, of at most 50,000.

According to some embodiments, the reactive condensation-curable amino-functional silicone pre-polymer forms, when in emulsion, emulsion droplets having an average size ($D_v50$) in the range of from about 200 nm to about 25 μm, or from about 1 μm to about 20 μm, or from about 200 nm to about 1 μm, or from about 0.5 μm to about 5 μm, or from about 0.7 μm to about 3 μm, or from about 1 μm to about 2.5 μm, or from about 1 μm to about 10 μm. The size of the droplets and/or the size homogeneity of the population of the droplets can be modified by selecting any desired emulsification method, modulating for instance the energy invested in the process and its duration. Low energy processes (e.g., shaking the mixture manually) may suffice to provide droplets in the 1-5 μm range, which may be heterogeneous in size. Medium energy processes (e.g., using a planetary centrifugal mill) may provide a more homogeneous population, the size of which can be modulated by duration and speed (e.g., providing droplets in the 10-20 μm range, if brief). High energy processes (e.g., using a sonicator) may rapidly provide droplets in the sub-micron range.

According to some embodiments, the reactive condensation-curable amino-functional silicone pre-polymer is present at a concentration in the range of from about 0.001 to about 20% by weight of the total weight of the composition (e.g., oil-in-water emulsion), such as from about 0.005 to about 10%, from about 0.005 to about 5%, from about 0.005 to about 2.5% or from about 0.01 to about 1% by weight of the total weight of the composition.

According to some embodiments, the concentration of reactive condensation-curable amino-functional silicone compounds is at least about 45 wt. % at least about 55%, at least about 60%, or at least about 65%, and optionally within a range of from about 50-100 wt. %, 50-95 wt. %, from about 50-90 wt. %, from about 50-85 wt. %, from about 50-80 wt. %, from about 55-95 wt. %, from about 55-85 wt. %, from about 60-95 wt. %, from about 60-85 wt. %, from about 65-95 wt. %, from about 65-90 wt. %, or from about 70-95 wt. % by weight of the oil phase.

According to some embodiments, the total concentration of amino-silicone oil is at most 30 wt. %, at most 20 wt. %, at most 15 wt. %, at most 10 wt. %, or at most 5 wt. % by weight of the oil phase.

According to some embodiments, the total concentration of non-amino-silicone oil is at most about 15 wt. %, at most about 12 wt. %, at most about 10 wt. %, at most about 7 wt. %, or at most about 5 wt. % by weight of the oil phase.

According to some embodiments, the sub-micronic pigment particles comprise an organic pigment, for example an organic pigment selected from the group consisting of perylene pigments; phthalocyanine pigments; quinacridone pigments; and imidazolone pigments.

According to some embodiments, the sub-micronic pigment particles comprises an inorganic pigment, for example an inorganic pigment selected from the group consisting of titanium dioxide, cadmium sulfoselenide, iron oxide, bismuth vanadate, cobalt titanate, sodium aluminosulfosilicate, mixed Fe—Mg—Ti oxides, manganese ferrite, and metallic or alloy pigments.

In some embodiments, the sub-micronic organic or inorganic pigments (or combinations thereof) serve as color imparting agents. The sub-micronic pigments may also be referred to as light absorbing pigments or simply as absorbing pigments.

According to some embodiments, the sub-micronic pigment is an organic or inorganic pigment selected from the group consisting of the following EU-approved colors for cosmetic use: CI 10006, CI 10020, CI 10316, CI 11680, CI 11710, CI 11725, CI 11920, CI 12010, CI 12085, CI 12120, CI 12370, CI 12420, CI 12480, CI 12490, CI 12700, CI 13015, CI 14270, CI 14700, CI 14720, CI 14815, CI 15510, CI 15525, CI 15580, CI 15620, CI 15630, CI 15800, CI 15850, CI 15865, CI 15880, CI 15980, CI 15985, CI 16035, CI 16185, CI 16230, CI 16255, CI 16290, CI 17200, CI 18050, CI 18130, CI 18690, CI 18736, CI 18820, CI 18965, CI 19140, CI 20040, CI 20470, CI 21100, CI 21108, CI 21230, CI 24790, CI 26100, CI 27755, CI 28440, CI 40215, CI 40800, CI 40820, CI 40825, CI 40850, CI 42045, CI 42051, CI 42053, CI 42080, CI 42090, CI 42100, CI 42170, CI 42510, CI 42520, CI 42735, CI 44045, CI 44090, CI 45100, CI 45190, CI 45220, CI 45350, CI 45370, CI 45380, CI 45396, CI 45405, CI 45410, CI 45430, CI 47000, CI 47005, CI 50325, CI 50420, CI 51319, CI 58000, CI 59040, CI 60724, CI 60725, CI 60730, CI 61565, CI 61570, CI 61585, CI 62045, CI 69800, CI 69825, CI 71105, CI 73000, CI 73015, CI 73360, CI 73385, CI 73900, CI 73915, CI 74100, CI 74160, CI 74180, CI 74260, CI 75100, CI 75120, CI 75125, CI 75130, CI 75135, CI 75170, CI 75300, CI 75470, CI 75810, CI 77000, CI 77007, CI 77266, CI 77267, CI 77268:1, CI 77891, CI 77947, lactoflavin, caramel, capsanthin, capsorubin, beetroot red, anthocynanins, bromothymol blue, bromocresol green, and acid red 195.

According to some embodiments, the sub-micronic pigment is selected from the group consisting of the following US-certified organic colors for cosmetic use:

D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10 and D&C Yellow No. 11.

In some embodiments, to be detailed in the following sections, inorganic pigments can be used in compositions, kits or methods according to the present teachings in a size range greater than sub-micronic range. Such inorganic pigments are either made of metals, alloys or oxides thereof, or formed as multilayer pigments based on substrates (such as mica, silica, borosilicate, plastic or even metals) coated with the same afore-mentioned metallic materials. Multilayer pigments having for instance a mica core or a silica core are also referred to as mica coated flakes or silica coated flakes, the coat (e.g., sometimes applied by chemical vapor deposition (CVD) or physical vapor deposition (PVD)) providing the look. These pigments typically provide a metallic appearance, and are thus collectively termed metallic pigments or metallic-looking pigments irrespective of chemical type.

While some of the above-mentioned metallic pigments may provide for a broad range of light reflection, others may be more specific, reflecting a narrow range of wavelengths or even a single wavelength (e.g., interference pigments). Such narrowly reflective pigments include by way of example mica pigments coated with a thin layer of metals, alloys or oxides thereof. As used herein, the term "reflective pigment" encompasses any metallic pigment able to reflect at least one wavelength. In some embodiments, the reflective pigment is further tinted to provide a coloring effect in addition to a light reflective effect.

In some embodiments, the reflective pigment is tinted with a dye selected from the group consisting of an azo dye (such as Color Index (C.I.) Reactive Yellow 4); an anthraquinone dye (such as C.I. Reactive Blue 19); and a phthalocyanine dye (such as C.I. Direct Blue 86).

In some embodiments, the metallic pigment is selected from the group consisting of aluminum, copper, zinc, iron, titanium, gold, or silver and alloys of these metals, such as brass, bronze or steel alloys. In some embodiments, the metallic pigment is selected from the group consisting of bismuth oxychloride, mica and silica coated with titanium dioxide, silicon dioxide, iron oxide, chromium oxide, zinc oxide, aluminum oxide, and tin dioxide. In some embodiments, the metallic pigment is further coated with dyes or sub-micronic pigments to additionally provide or enhance a coloring effect, such as, for example, aluminum pigment coated with phthalocyanine blue or Cinquasia® red. In some embodiments, there are provided multi-layer pigments based on synthetic substrates such as alumina, silica, calcium sodium borosilicate or calcium aluminium borosilicate, and aluminium.

In addition to having, in some embodiments, at least one dimension above one micrometer, the metallic pigments have advantageously a flake-like or platelet shape.

In some embodiments, the pigments of the present compositions provide a special visual effect, instead of or in addition to a coloring effect and/or a metallic appearance. Special effects include, by way of non-limiting example, a fluorescent effect, a glittering effect, a pearlescent effect, a nacreous effect and a phosphorescent effect. These effects may be visible under regular illumination or may require (or be further increased) by special conditions of observation, such as a function of lighting conditions, angle of observation etc. For instance, fluorescent pigments may become visible or may provide a fluorescent effect when subjected to ultraviolet (UV) light. At the other end of the spectrum, up-converting pigments are luminescent materials which are able to convert near infrared (NIR) light to visible (VIS) light. Additional colorants providing for less typical coloring further include, by way of non-limiting example, thermochromic pigments or dyes, allowing the compositions comprising them to change color as a result of a change in temperature, and pH dependent pigments, whose color is modified by pH.

Any of the afore-said pigments can further be surface treated, for instance with an organic agent, so as to further improve any desired property of the pigment (e.g., visual effect, chemical stability, dispersibility etc.). Surface treatment techniques need not be detailed herein and surface-treated pigments may be commercially available in the required form (e.g. non-ionic, cationic, anionic, or positively charged, negatively charged, or substantially non-charged). All of such pigments may be employed by all aspects and embodiments of the present hair-coloring methods and the kits therefor. In one embodiment, the pigment particles can be surface treated (e.g., by acid groups), so as to ameliorate interaction between the pigment and the amino-silicone pre-polymers entrapping them during the formation of a 3D network of amino-silicone on the hair fiber. Color imparting agents as used in the present disclosure are pigments, which may optionally be combined or replaced by dyes in particular cases (e.g., for tinting). However, even when dyes are used as color imparting agent to a composition or to a pigment coat, they are not oxidative dyes. In some embodiments, compositions according to the present teachings are substantially devoid of oxidative dyes and of any chemical agent conventionally used in combination with oxidative dyes, including by way of non-limiting example, dyes' couplers and oxidizing agents (e.g., a hydrogen peroxide developer).

Depending on their morphology, particles (e.g., sub-micronic (absorbing) pigments, metallic (reflective) pigments, and the like) may be exemplified by their length, width, thickness, diameter, or any such representative measurement of their X-, Y- and Z-dimensions. Typically such sizes are provided as average of the population of particles and are provide by the manufacturer of such materials. These sizes can be determined by any technique known in the art, such as microscopy and Dynamic Light Scattering (DLS). In DLS techniques, the particles are approximated to spheres of equivalent behavior and the size can be provided in terms of hydrodynamic diameter. DLS also allows assessing the size distribution of a population. The same applies to liquid droplets and may assist for instance in the characterization of emulsion droplets, all typically having a globular shape. As used herein, particles having a size of, for instance, about 1 μm or less, have at least one dimension equal to or smaller than about 1 μm, and possibly two or even three, depending on shape. When concerned with emulsion droplets having, by way of example, a size of about 5 μm or less, the droplets are understood to have an average diameter ($D_V50$) equal to or smaller than 5 μm.

Though not essential, the particles or emulsion droplets of any particular kind may preferably be uniformly shaped and/or within a symmetrical distribution relative to a median value of the population and/or within a relatively narrow size distribution for this particular kind. In the following, and unless otherwise clear from context, the term "particle" refers both to solid particles (e.g., pigments and the like) and to liquid droplets (e.g., emulsion droplets, micelles and the like).

A particle size distribution (PSD) is said to be relatively narrow if at least one of the two following conditions applies:

A) the difference between the hydrodynamic diameter of about 90% of the particles and the hydrodynamic diameter of about 10% of the particles is equal to or less than about 150 nm, or equal to or less than about 100 nm, or equal to or less than about 50 nm, which can be mathematically expressed by: (D90−D10)≤150 nm and so on; and/or B) the ratio between a) the difference between the hydrodynamic diameter of about 90% of the particles and the hydrodynamic diameter of about 10% of the particles; and b) the hydrodynamic diameter of about 50% of the particles, is no more than about 2.0, or no more than about 1.5, or no more than about 1.0, which can be mathematically expressed by: (D90−D10)/D50≤2.0 and so on.

D10, D50 and D90 can be assessed by number of particles in the population, in which case they may be provided as $D_N10$, $D_N50$ and $D_N90$, or by volume of particles, in which case they may be provided as $D_V10$, $D_V50$ and $D_V90$. The foregoing measurements can be obtained by DLS techniques when the samples to be studied are suitably fluid or by microscopy when the particles under study are in dry form. As used herein, D50, which can also be termed the "average measured particle size" or simply the "average particle size" may refer, depending on the measuring method most suited to the particles being considered and their media, either to $D_V50$ (by DLS and the like) or to the volume average size of particles found in a field of view of a microscope adapted to analyze in the scale of the particles. D90 accordingly relate to measurements applying to about 90% of the population under study, thus also termed the "predominant measured particle size" or simply the "predominant particle size" which can for instance be assessed by DLS techniques as $D_V90$.

As mentioned above, such relatively uniform distribution may not be necessary for certain applications. For instance, having a relatively heterogeneously sized population of sub-micronic pigments or of metallic pigments particles may allow, in a coating formed thereby, relatively smaller particles to reside in interstices formed by relatively larger particles providing in combination a relatively uniform coating.

The particles may be exemplified by an aspect ratio, i.e., a dimensionless ratio between the smallest dimension of the particle and the longest dimension or equivalent diameter in the largest plane orthogonal to the smallest dimension, as relevant to their shape. The equivalent diameter (Deq) is defined by the arithmetical average between the longest and shortest dimensions of that largest orthogonal plane. Particles having an almost spherical shape, and emulsion droplets amongst them, are exemplified by an aspect ratio of approximately 1:1, whereas rod-like particles can have higher aspect ratios and flake-like particles can even have an aspect ratio of up to about 1:100, or even more.

Such characteristic dimensions are generally provided by the suppliers of such particles and can be assessed on a number of representative particles by methods known in the art, such as microscopy, including, in particular, by light microscope for particles of several microns or down to estimated dimensions of about 200 nm, by scanning electron microscope SEM for smaller particles having dimensions of less than about 200 nm (SEM being in particular suitable for the planar dimensions) and/or by focused ion beam FIB (preferably for the thickness and length (long) dimensions of sub-micronic particles, also referred to herein as nanoparticles or nanosized particles). While selecting a representative particle, or a group of representative particles, that may accurately characterize the population (e.g., by diameter, longest dimension, thickness, aspect ratio and like characterizing measures of the particles), it will be appreciated that a more statistical approach may be desired. When using microscopy for particle size characterization, a field of view of the image-capturing instrument (e.g., light microscope, SEM, FIB-SEM etc.) is analyzed in its entirety. Typically, the magnification is adjusted such that at least about 5 particles, at least about 10 particles, at least about 20 particles, or at least about 50 particles are disposed within a single field of view. Naturally, the field of view should be a representative field of view as assessed by one skilled in the art of microscopic analysis. The average value characterizing such a group of particles in such a field of view is obtained by volume averaging. In such case, $D_V 50 = \Sigma[(D_{eq}(m))^3/m]^{1/3}$, wherein m represents the number of particles in the field of view and the summation is performed over all m particles. As mentioned, when such methods are the technique of choice for the scale of the particles to be studied or in view of their media, such measurements can be referred to as D50.

According to some embodiments, the sub-micronic pigment comprises on average particles having a $D_V 50$ of at most about 1,000 nm, at most about 750 nm, at most about 500 nm, at most about 250 nm, at most about 150 nm, or at most about 100 nm, and optionally, a $D_V 10$ of at least about 10 nm, at least about 25 nm, or at least about 50 nm. In some embodiments, the sub-micronic pigment particles are in a range comprised between a $D_V 10$ of at least about 10 nm and a $D_V 90$ of at most about 2,500 nm, or in a range between a $D_V 10$ of at least about 25 nm and a $D_V 90$ of at most about 1,500 nm, or in a range between a $D_V 10$ of at least about 50 nm and a $D_V 90$ of at most about 1,000 nm.

According to some embodiments, the sub-micronic pigment predominantly comprises particles having a $D_V 90$ of at most about 1,000 nm, at most about 750 nm, at most about 500 nm, at most about 250 nm, at most about 150 nm, or at most about 100 nm, and optionally, a $D_V 50$ of at most about 300 nm, at most about 250 nm, at most about 200 nm, at most about 150 nm, at most about 100 nm, or at most about 75 nm. In some embodiments, the sub-micronic pigment particles have a $D_V 10$ of at least about 10 nm, at least 25 nm, or at least about 50 nm. In some embodiments, the sub-micronic pigment particles are in a range comprised between a $D_V 10$ of at least about 10 nm and a $D_V 90$ of at most about 1,000 nm, or in a range between a $D_V 10$ of at least about 25 nm and a $D_V 90$ of at most about 750 nm, or in a range between a $D_V 10$ of at least about 25 nm and a $D_V 90$ of at most about 500 nm.

According to some embodiments, the composition or kit disclosed herein further comprises a cross-linker, for example, an organosilicon compound able to react through all non-amino reactive groups of the reactive silicone, and a cross-linking agent comprising a mercapto group, an epoxy group or an acrylate group, all able to react through amino reactive groups of the reactive silicone.

Generally, cross-linking agents comprise at least three reactive groups for the formation of the network of oligomers and polymers resulting in the elastomeric network.

The organosilicon cross-linking agent must have hydrolysable groups (Y).

After hydrolysis, the silanol groups obtained can undergo condensation reaction with the reactive amino-silicone pre-polymer to give siloxane bonds.

The organosilicon cross linker can contain:
tetrafunctional hydrolysable groups and consist for example of silane having a Q units ($SiO_{4/2}$), such as $SiY_4$ or trifunctional hydrolysable groups and include silane or siloxane oligomers having T units of the formula $R^a SiO_{3/2}$, like $R^a SiY_3$ or difunctional hydrolysable groups and include silane or siloxane oligomers having D units of the formula $R^b{}_2 SiO_{2/2}$, like $R^b{}_2 SiY_2$, as long as the cross-linker has a total of at least three hydrolysable groups, or monofunctional hydrolysable groups having M units, as long as the cross-linker has a total of at least three hydrolysable groups, where the hydrolysable group (Y) can be selected from
Alkoxy (e.g., methoxy, ethoxy, propoxy, isopropoxy, methoxyethoxy and the like)
Oxime (e.g., methylethylketoxime)
Acyloxy (e.g., acetoxy)
where the $R^a$ and $R^b$ substituents are selected from
$C_1$-$C_6$ or $C_1$-$C_4$ Alkyl groups,
Alkenyl groups (vinyl, allyl, etc.),
Aminoalkyl groups (monoamino, such as aminopropyl $NH_2(CH_2)_3$: diamino, such as aminoethylaminopropyl $NH_2(CH_2)_2NH(CH_2)_3$; or triamino)
Epoxy group (e.g., glycidoxypropyl)
Acrylate group (e.g., methacryloxypropyl)
Mercapto group (e.g., mercaptopropyl)

According to some embodiments, the cross-linking agent can be a branched or a linear polyorganosiloxane comprising at least one of Q units, T units, D units and M units, with the proviso that the total amount of hydrolysable groups and/or of silanols in the cross-linking agent is of at least three, allowing the formation of a 3D network. When a mixture of cross-linking agents is used, at least one cross-linking agent of the mixture must contain a total of at least three hydrolysable groups and/or of silanols.

According to some embodiments, the cross-linker can be an ethylsilicate, such as tetraethylsilicate (CAS No 78-10-4), poly(diethoxysiloxane) oligomers, such as Evonik Dynasylan® 40 with a silicon dioxide content of approximately 40-42% upon complete hydrolysis, Colcoat® Ethylsilicate 48 with a silicon dioxide content of approximately 48% upon complete hydrolysis (CAS No. 11099-06-2), poly (dimethoxysiloxane) (CAS No. 25498-02-6), 3-Glycidyloxypropyl trimethoxysilane by Evonik, Carbodilite Emulsion E-05, having 40% multifunctional polycarbodiimide in anionic emulsion, and Carbodilite V02-B, having 100% multifunctional polycarbodiimide.

According to some embodiments, the cross-linker can be a reactive amino-silicone monomer, such as aminopropyl-triethoxysilane (CAS No. 919-30-2), bis(triethoxy-silylpropyl)amine (CAS No. 13497-18-2), or mixtures thereof.

According to some embodiments, the cross-linker is a non-amino silicone having a molecular weight of less than about 1000 g/mol, thus includes, mainly includes, or includes a reactive condensation-curable film-forming non-amino-silicone monomer. In some embodiments, the total concentration of the non-amino cross-linking agent is at most about 35 wt. %, at most about 30 wt. %, at most about 20 wt. %, at most about 15 wt. %, at most about 10 wt. %, or at most about 5 wt. % by weight of the oil phase.

As used herein in the specification and in the claims section that follows, the term "mainly includes", typically with respect to a component within a formulation, refers to a weight content of at least about 50% of that component.

According to some embodiments, the total concentration of: reactive condensation-curable film-forming amino-silicone pre-polymers; amino- and non-amino-silicone oils; non-amino cross-linking agent; and reactive filler, including any pigment particles and dispersant for said pigment particles, within said oil phase, is at least about 90 wt. %, at least about 93 wt. %, at least about 95 wt. %, at least about 97 wt. %, at least about 98 wt. %, or at least about 95 wt. %, by weight of the total composition.

According to some embodiments, the pigment is further coated with a chemical coat which does not interfere with the visual effect of the underlying pigment. Such a chemical coat can provide protection to the pigment, such as providing anti-oxidant properties, or any other desired property, by way of example, dispersibility, stability, ability to adhere to the fibers, charge and like characteristics that improves pigment activity and intended effect. For instance, the chemical coat can be a fatty acid, such as oleic acid, stearic acid, an adhesion promoting polymer coat, such as an acrylic polymer, a silane polymer or an amino-silane polymer, and such chemical coats known in the art of pigments.

In other embodiments, the chemical coat provides a visual effect, for instance when the pigment a flake-like shaped metallic pigment (e.g. mica or glass flakes, having an average greatest dimension in the range of from about 2 to about 20 µm), the coating may be a metal oxide, such as, for example, titanium dioxide or ferric oxide.

According to some embodiments, the emulsion comprises an oil-in-water emulsion, prepared in the presence of a non-ionic emulsifier, preferably having a hydrophile-lipophile balance (HLB) value between about 12 to about 18, from about 12 to about 17, from about 12 to about 16, from about 12 to about 15, or from about 13 to about 16 on a Griffin scale. Emulsions can be prepared by a number of emulsification techniques known to the skilled person. While manual shaking may suffice, various equipment, such as a vortex, an overhead stirrer, a magnetic stirrer, an ultrasonic disperser, a high shear homogenizer, a sonicator and a planetary centrifugal mill, to name a few, can be used, typically providing more homogenous populations of oil droplets in the aqueous phase. The emulsion can be readily applied following its preparation or within a time period during which it remains suitably stable. For instance, the emulsion can be applied as long as the oil droplets are within their desired size range and providing that the emulsified amino-silicone pre-polymers remain reactive. As the thickness of the coat is believed to be proportional to the average diameter of the droplets, too large droplets are to be avoided if a thin coat is desired, while on the other hand too small droplets would not be able to embed pigment particles having sufficient size to provide for the desired visual effect. This time window may vary with the constituents of the emulsion and their respective amounts, the presence of an emulsifier typically extending it. In some embodiments, the emulsion is applied to the hair fibers within at most about 30 minutes from its emulsification, or within at most about 20 minutes, at most about 10 minutes, or at most about 5 minutes.

According to some embodiments, the aqueous carrier comprises at least about 60% water by weight of the liquid carrier, or at least about 65 wt. %, or at least about 70 wt. %, or at least about 75 wt. %, or at least about 80 wt. %, or at least about 85 wt. %, or at least about 90 wt. %, or at least about 95 wt. % water. In some embodiments, the total concentration of the water and any emulsifier is at least about 90 wt. %, at least about 95 wt. %, at least about 97 wt. % at least about 99 wt. %, by weight of the aqueous phase.

In cases in which the amount of pigments and/or their density is high, while the liquid carrier will predominantly comprise water, the water may constitute only about 30% by weight of the total composition.

According to some embodiments, a pH of the composition is in the range of from about 4 to about 12, from about 6 to about 12, from about 8 to about 11, or from about 9 to about 11.

According to some embodiments, the composition or kit further comprises at least one additive selected from the group consisting of dispersant, pH modifying agents, preservatives, bactericide, fungicide, viscosity modifiers, thickeners, chelating agents, vitamins and perfumes. Depending on the mode of application, additional agents can be required, for instance, a propellant can be added if the composition is to be applied as a propelled spray.

According to some embodiments, the composition is in the form selected from the group consisting of a paste, a gel, a lotion, and a cream.

According to some embodiments, the keratinous fibers are mammalian hair. In some embodiments, the hair is human hair or animal hair, the hair being selected from body hair, facial hair (including for example moustaches, beards, eyelashes and eyebrows) or head hair. In further embodiments, the hair is attached to a body or scalp of a human or an animal subject. Human hair can be of any human race (e.g., European, Asian, African, etc.) and any type, such as straight, wavy, curly, or kinky, whether naturally or artificially so. Human hair not attached to a subject can be found in wigs, hair extensions, eyelash extensions, and like products. In some embodiments, the keratinous fibers are dry, non-wetted, or to pre-dyed. In some embodiments, the keratinous fibers are unpre-degreased, unpre-shampooed, and unpre-bleached.

EXAMPLES

Example 1: Coloring of Light-Colored Keratinous Fibers

Materials
Hair
   Yak white body hair; Chinese black human hair; European black human hair (all supplied by Kerling International Haarfabrik GmbH, as tufts of about 2.5 g of hair having a length of approximately 7 cm)
Organic Pigments
   Heliogen® Green K8730 (BASF, Germany)
   Cromophtal® Yellow 3RT (BASF, Germany)
   Irgazin® Magenta 2012 (BASF, Germany)
Dispersant
   2-ethylhexanoic acid (Sigma-Aldrich, USA)
Reactive Condensation-Curable Amino-Silicone Pre Polymers
Amino-silicone ATM 1322 (Amine Number 80); (Gelest® Inc., USA)
Amino-silicone GP-34 (Amine Number 3.3, MW ~33,596);
Amino-silicone GP-145 (Amine Number 11, MW ~18,052);

Amino-silicone GP-397 (Amine Number 116, MW ~3,754);
Amino-silicone GP-657 (Amine Number 54, MW ~3,700);
and Amino-silicone GP-846 (Amine Number 110); (all of Genesee Polymers Corp., USA).
Amino-silicone KF-857 (Amine Number 127); Amino-silicone KF-862 (Amine Number 53); (all of Shin-Etsu Polymer Co. Ltd., Japan).
Amino-silicone SF 1706 (Amine Number 47); Amino-silicone TSF 4703 (Amine Number 62);
Amino-silicone TSF 4707 (Amine Number 15); Amino-silicone TSF 4708 (Amine Number 38); (all of Momentive Performance Materials Inc., USA).
Xiameter® OFX 8630 (Amine Number 25); Xiameter® OFX 8822 (Amine Number 45); (all of Dow Corning, USA).
Non-Reactive Silicone-Based Materials
    Amino-silicone Rhodorsil 21642 (Amine Number 20); (Bluestar Silicones International, France).
Diluents
    Hexamethyldisiloxane 98% (Acros Organics, USA)
Ethanol (Gadot, Israel)
Aluminum Pigment
    Vacuum metalized passivated aluminum flake pigments (AQ-4172 PA, Silberline, USA)
Cross-Linker
    3-Glycidyloxypropyl trimethoxysilane (Evonik® Industries, Germany)
Emulsifier
    Tween® 80 (Sigma Aldrich, USA)
Cure Accelerator
    Carbodilite Emulsion E-05 (40% multifunctional polycarbodiimide in anionic emulsion)
Carbodilite V02-B (100% multifunctional polycarbodiimide)
Shampoo
    Shea Natural Keratin Shampoo (Saryna Key, Israel)
Equipment
    Attritor® HD01 (Union Process, USA)
T25 Ultra Turrax digital (IKA, Germany)
Digital Orbital Shaker TOU 50 (MRC Lab, Israel)
Heraeus oven, UT 12 (Thermo Scientific, USA)
Sonicator Q700 (Qsonica LLC, USA)
Zetasizer Nano S light scattering device (Malvern Instruments Ltd., UK)
Water bath WBL-200 (MRC, UK)
528 Spectro-Densitometer (X-Rite Inc., USA)
Methods
Preparation of Slurry Comprising Sub-Micronic Particles of Pigment
    4 kg of stainless steel 5 mm beads were added to 100 gr of organic pigment and 100 gr of 2-ethylhexanoic acid.

Organic pigments initial size was as provided by respective suppliers, generally all in the tens of micrometers range. The slurry was then bead-milled for 1 hour, at 400 RPM, 55° C. using an Attritor® HD01 with a double jacket tank-refrigerated circulated water bath WBL-200 to produce a milled slurry comprising sub-micronic particles of the pigment. The slurry was separated from the beads by gravitation.
Size Analysis
    100 mg of the milled slurry were diluted in 10 g of 2-ethylhexanoic acid at ambient temperature (circa 23° C.). The diluted slurry was re-suspended in 2-ethylhexanoic acid using a Sonicator Q700 at 500 W amplitude for 7 sec.
    1 g of the sonicated suspension was then placed in a plastic cuvette and allowed to equilibrate for 60 seconds at ambient temperature. Particle size was measured using a dynamic light scattering (DLS) device, Zetasizer Nano S, with 10 measurements of 10 seconds each. The average particle diameter size by volume $D_V50$, was found to be approximately 150 nm for all size-reduced organic pigments, their $D_V90$ being of about 900 nm.
    Additional slurries of sub-micronic pigments were similarly prepared by replacing the dispersant 2-ethylhexanoic acid by BYK LPX 21879, a non-reactive amino-silicone dispersant known as a wetting and dispersing additive for unipolar systems. Unless otherwise indicated, the weight per weight (w/w) ratio of pigment to dispersant in the milling stage was of 1:1. In this method, the pigment:dispersant mix was supplemented with 200 g of a volatile solvent, such as hexamethyldisiloxane. Pigments, size reduced in presence of this alternative dispersant, were similarly milled down to average sizes of about 150 nm, as assessed by $D_V50$, the pigments having a $D_V90$ of about 900 nm or less. The volatile solvent was evaporated before further use of the sub-micronic pigments.
Preparation of Compositions for Coloring Keratinous Fibers
    Coloring compositions A to E were prepared, comprising components as detailed in Table 1.

TABLE 1

| | | Composition (weights in grams) | | | | |
|---|---|---|---|---|---|---|
| Component | Function | A | B | C | D | E |
| Heliogen ® Green K8730 | Green organic pigment | 1.25 | — | — | 1.25 | 1.25 |
| Cromophtal ® Yellow 3RT | Yellow organic pigment | — | 1.25 | — | | |
| Irgazin ® Magenta 2012 | Red organic pigment | — | — | 1.25 | | |
| 2-ethylhexanoic acid | Dispersant | 1.25 | 1.25 | 1.25 | 1.25 | 1.25 |
| Amino-silicone GP-397 | Reactive terminal amino functional silicone polymer | 10 | 10 | 10 | | |
| Amino-silicone GP-657 | Reactive terminal amino functional silicone polymer | | | | 10 | |
| Amino-silicone KF-862 | Reactive side chain amino functional silicone polymer | | | | | 10 |
| Hexamethyldisiloxane 98% | Diluent | 87.5 | 87.5 | 87.5 | 87.5 | 87.5 |

All compositions of Table 1 were prepared as follows:
    80 g of reactive amino-silicone were added to 25 g of milled slurry comprising sub-micronic particles of organic pigment (green, yellow or red), prepared as described above. The mixture was then sonicated using Qsonica Sonicator Q700 at 500 W amplitude for 1 min. 12.5 g of the mixture were diluted with 87.5 gr hexamethyldisiloxane. The pH of the compositions was measured and found to be basic, all being of approximately pH 10. It is to be noted that the present samples, while being technically coloring compositions, are intentionally devoid of cross-linking agents and optional accelerating agents or catalysts as claimed for practical coloring, in order to obtain a preliminary assessment of the basic adherence of the amino-silicone elastomers to keratinous fibers.

Coating of Keratinous Fibers

Coated samples A to E were prepared by immersing tufts of untreated yak hair (2.5 grams per tuft), in one of compositions A to E, respectively, for about 1 minute at ambient temperature. As yak hair has a very light straw-like shade, the coloring samples due to result in darker shades were applied to the fibers without any color modifying pre-treatment (e.g., no bleaching).

The samples were subsequently rinsed thoroughly in tap water at ambient temperature, dried for 30 seconds with a Philips Compact Hair Dryer and combed. Some of the colored samples were at this stage sticky to the touch, with less individualization of the hair fibers. The hair samples were and then transferred to a Heraeus oven, UT 12, for 7 days at 60° C. and 100% relative humidity, to fully cure the condensation-curable reactive polyamino-silicone (e.g., by self cross linking) in the absence of agents otherwise favoring or accelerating such curing, as cross-linking agents and optional catalysts.

For comparative purposes, samples F and G were prepared, comprising yak hair tufts coated with commercial black and brown hair dyes, respectively, both providing for a coloring effect deemed permanent. Yak hair tufts (2.5 grams each) were first bleached with a commercial bleaching kit (Elgon De Color, comprising bleach powder and 6% Joya oxygen cream, at a ratio of 4:3 weight percentage bleach powder: oxygen cream) for 30 minutes and then thoroughly rinsed with tap water. In the present case, bleaching was performed not to remove the original hair color but to facilitate the penetration of the dyes through the hair surface.

Following rinsing, sample F was prepared by immersing a bleached tuft in Elegon Moda & Styling color cream, black 1 for 45 minutes and sample G was prepared by immersing a bleached tuft in Kosswell professional Equium color cream, dark blonde 6, for 45 minutes. Samples F and G were subsequently thoroughly rinsed in tap water.

Color-Fade Measurements (Wash-Resistance)

Following full curing of the coats, the extent of coloring of samples A to G was measured in terms of optical density (OD) using a 528 Spectro-Densitometer (X-Rite, Inc.) within a spectral range of 400-700 nm. The value obtained following the coloring process (and when applicable the full curing of the condensation-curable amino-silicone elastomer) was taken to be the baseline OD for each sample.

The measured OD at baseline (0 shampoo) varied depending on the color imparting sub-micronic pigment or commercially available permanent dyes, and was of about 1.5, 1.1, 1.3, 1.8, 1.2, 1.7 and 1.6, for samples A-G, respectively. For comparison, the OD of yak hair samples without any coloring treatment or coated under similar conditions with a composition comprising 10% amino-silicone GP-397 diluted in hexamethyldisiloxane without any pigment were also measured and found to both have an average value of approximately 0.36 supporting the transparency of the cured amino-silicone on the coated hair.

Color-fade or wash-resistance was studied by measuring the OD of each of the samples following various numbers of standard shampooing treatments, using Shea Natural Keratin Shampoo and drying with a Philips Compact Hair Dryer. The shampooing and drying treatment was repeated up to 130 times, and the OD measured after 1, 2, 4, 10, and then after every 10 treatments.

Unless otherwise stated, each measurement was performed in triplicate and the results reported below represent the mean value obtained.

Results are presented in FIG. 2A, showing OD as a function of the number of shampooing and drying treatments, expressed as percentage of baseline OD. For convenience, computer generated trendlines were added for each series.

Results

The reduction in the extent of coloring of the hair samples under study became detectable to the naked eye (i.e. visibly detectable) when the measured OD decreased below about 80% of the baseline OD value.

As seen in FIG. 2A, samples A, B and C appeared to be resistant to color-fade for up to at least about 110, 70 and 90 shampooing and drying treatments, respectively (i.e. OD remained above 80% of the baseline OD value for the respective number of treatments). As wash resistance of at least 30 shampooing is often considered as threshold for the lasting effect of coloration, it can be concluded that samples A, B and C as herein disclosed are suitable for permanent coloring of keratinous fibers even in the absence of cross-linking agents/catalysts. Addition of such agents is expected to accelerate the initial curing on the keratinous fibers, rapidly providing for non-sticky hairs. Such addition of cross-linking agents is necessary when coloring human or animal hair attached to respective subjects to promote a dry feeling to the touch, enhancing compliance, but not essential if coloring fibers that can be incubated for prolonged period of times at relatively elevated temperatures. Similarly, an optional accelerating agent or catalyst can be further added to promote such rapid initial partial-curing. It is believed that such additions do not significantly modify the color-fade resistance of full coloring compositions comprising them in addition to the condensation-curable amino-silicone and the sub-micronic pigments. It should be noted that as in absence of post-coloration incubation, some samples (e.g., containing slow curing polymers) were sticky, it can be concluded that the aqueous phase of the emulsions is not sufficient to promote curing to a non-sticky extent. Similarly, applying the slow curing compositions on wet hair (e.g., just washed) does not affect the process.

Comparative samples F and G, prepared using commercially available permanent dyes (penetrating the hair shaft and believed to react therein), also exhibited significant resistance to shampooing, both maintaining OD within range of undistinguishable color change for at least 150 treatments. Samples D and E, not shown on the graph, displayed a coloring resistance to about 8-10 and 5-6 shampooing cycles, respectively, qualifying them as semi-permanent coloring compositions. It is to be noted that a commercially available coloring composition sold as a temporary coloring formulation achieved a color-fade resistance of only about 2-3 shampooing, further supporting the significance of the result achieved by the compositions of the present disclosure.

It can be extrapolated that similar permanency applies to pigment-less coatings, as the wash resistance of the coating is expected to increase in absence of a pigment and possibly of a dispersant. Thus, a pigmented coating exhibiting good wash resistance, as demonstrated by a measured OD following wash test of more than 80% of the pre-wash baseline OD value, can predict an at least similarly suitable attachment of the corresponding pigment-less coating to the hair.

Hence, if the wash-resistance of a pigment-less coat is desired, a corresponding lightly pigmented (e.g., up to 1 wt %) coat can serve as substitute to estimate wash resistance by way of optical density. Alternatively, the coated hair, in particular if pigment-less, can be analyzed for the presence of any characteristic on the external surface of the fibers, other than color, before and after being subjected to at least 20 wash cycles. When the measured characteristic remains substantially constant after the wash-resistance test, coating is deemed permanent. The coating characteristics that may support such permanency include, for example: the weight of an hair sample (as can be determined by an analytical balance), the thickness of the coat on the hair surface (as can be determined by microscopy), the presence of cured polymers on the hair surface (as can be determined by the existence of a glass transition temperature, as detectable by DSC), and the presence of particular chemical moieties (as can be determined by suitable analytical methods, including for example, by FTIR spectroscopy). Some characteristics and techniques of detection are compatible with direct analysis of the coat while attached to the hair fibers. Others may require a preliminary separation of the coat to perform the analysis ex situ. This can be the case, when the underlying hair fiber can mask the monitored feature or otherwise reduce the significance of the signal being measured.

Example 2: Aqueous Compositions for Coloring Keratinous Fibers

Preparation of Compositions

Samples AA to AN were prepared comprising components as detailed in Table 2 and as described below, wherein the condensation-curable silicone was selected from the list shown in the following table in which some parameters concerning these elastomers are presented.

obtain a colored paste. 0.2 g of the colored paste were diluted with 60 g of water with 0.1 wt. % Tween® 80. The diluted mixture was then sonicated using Qsonica Sonicator Q700 for 10 seconds at 80% amplitude to obtain a colored emulsion. The pH of the colored emulsions was measured and found to be basic, all being of approximately pH 10.

Coating of Keratinous Fibers

Coated samples were prepared by immersing tufts of untreated white yak hair (2.5 g per tuft) in one of compositions AA to AN, respectively, for 45 seconds at ambient temperature, with gentle stirring. The samples were subsequently rinsed thoroughly in tap water at about 40° C., then dried for about 30 seconds with a Philips compact hair dryer and combed. The samples were then maintained at ambient temperature and above 30% relative humidity for about 1-3 weeks.

Results

The measured OD at baseline (0 shampoo) varied depending on the amino-silicone elected and was generally between about 1.1 and about 1.4, demonstrating satisfactory baseline coloring (the white Yak hair control having an OD of only about 0.36). It should be noted that such coloring was rapidly obtained, the process till drying being completed within minutes of application of the condensation-curable amino-silicone coating composition. Such rapidity is in clear contrast with conventional wet coloring methods.

Color-fade was studied as previously described following completion of curing, by measuring after every 5 cycles the

TABLE 2

| Sample | Silicone | Amine No.* | Amine Position (Polymer type**) | Amine Type | Reactive Group | Viscosity (mPa · s) | Shampoo Resist |
|---|---|---|---|---|---|---|---|
| AA | ATM 1322 | 101 | Pendant (LP) | I, II | Methoxy | 250 | ≥65 |
| AB | GP-34 | 3.3 | Terminal (LP) | I | Methoxy | 3500 | ≥20 |
| AC | GP-145 | 11 | Terminal (LP) | I | Ethoxy | 1900 | ≈18 |
| AD | GP-397 | 116 | Terminal (LP) | I, II | Methoxy | 130 | ≥110 |
| AE | GP-657 | 54 | Terminal (LP) | I | Methoxy | 120 | ≥100 |
| AF | GP-846 | 110 | N/A (BP) | I, II | Methoxy | 30 | ≥55 |
| AG | KF-857 | 127 | Pendant (LP) | I | Methoxy | 65 | ≥130 |
| AH | Bluesil 21642 | 15 | Pendant (LP) | I, II | Methoxy | 1400 | ≥10 |
| AI | SF 1706 | 47 | Pendant (BP) | I, II | Methoxy | 30 | ≈20 |
| AJ | TSF 4703 | 62 | Pendant (LP) | I, II | Methoxy | 1000 | ≥50 |
| AK | TSF 4707 | 15 | Pendant (LP) | I, II | Methoxy | 7000 | ≥20 |
| AL | TSF 4708 | 38 | Pendant (LP) | I, II | Methoxy | 1000 | ≥10 |
| AM | Xiameter® OFX 8630 | 25 | Pendant (LP) | I | Ethoxy | 3500 | ≥30 |
| AN | Xiameter® OFX 8822 | 45 | Pendant (LP) | I | Methoxy | 1500 | ≈20 |

*Amine Number refers to milliliters of 0.1N HCl needed to neutralize 10 g of polymer
**LP = Linear polymer; BP = Branched polymer All compositions of Table 2 were prepared as follows:

8 g of reactive amino-silicone were added to 2 g of milled slurry comprising sub-particles of Cromophtal® Yellow 3RT with BYK LPX 21879 as dispersant, prepared as described above, and mixed on a Teflon® surface using a painting trowel. The mixture was then homogenized using IKA Ultra Turrax T25 at 25,000 rpm for 30 seconds, to OD of each of the samples following various numbers of standard shampooing and drying treatments, which were performed up to 130 times.

Results were analyzed and the change in OD as a function of the number of shampooing and drying treatments, expressed as percentage of baseline OD, was calculated for each sample. The patterns of selected samples are shown in FIG. 2B, which for convenience includes computer generated linear trendlines for each series. The number of shampoos each sample withstood before undergoing a visible change in color (as confirmed by a measured OD smaller than 80% of baseline OD) is reported in the above table.

As seen in FIG. 2B showing the color resistance over the first 50 cycles, samples AA, AD, AE, AF, AG and AJ appeared to be resistant to color-fade for up to at least 45 shampooing and drying treatments. As shown in Table 2, samples AD, AE and AG are expected to resist even more than 100 shampooing. As wash resistance of at least 30 shampooing is often considered as threshold for the lasting effect of coloration, it can be concluded that samples AA, AD, AE, AF, AG, AJ and AM as herein disclosed are suitable for permanent coloring of keratinous fibers even in absence of cross-linking agents/catalysts. Similarly, as wash resistance in the range of about 10-30 shampooing is qualifying coloration as demi-permanent, it can be concluded that the condensation-curable amino-silicones as used in samples AB, AC, AH, AI, AK, AL and AN are suitable for the preparation of demi-permanent coloring compositions, capable of coloring keratinous fibers.

As seen from Table 2, based on the reactive condensation-curable amino-silicone elastomers of the present example, two trends seem to emerge. First, while satisfactory coloring can be obtained with pre-polymers having an Amine Number as low as about 3 (see sample AB resisting 20 or more shampooing cycles), it can be generally observed that condensation-curable amino-silicones having higher Amine Numbers provide for an increase in resistance to shampooing (see for instance sample AG resisting more than 100 cycles). Without wishing to be bound by theory, it is believed that a pre-polymer having a higher Amine Number may permit the formation of more bonds with hydroxyl residues or acidic groups on a hair fiber than a pre-polymer having a relatively lower Amine Number. Understandingly, the amine moieties that may participate in such attachment need be sufficiently exposed, hindered amine moieties being expected to be of less relevance to direct attachment.

A second trend concerns the viscosity of the elastomers. While coloring has been obtained with reactive condensation-curable amino-silicone pre-polymers having a wide range of pre-curing viscosities (from 30 to 7000 mPa·s), generally the pre-polymers having a relatively lower viscosity tended to provide a higher resistance to shampoo-induced color fading. As previously explained, condensation-curable amino-silicones having a relatively lower viscosity are expected to have a relatively higher ability to sufficiently wet the hair surface, enabling thereby intimate contact and the formation of enough attachment to resist washing or shampooing cycles. Moreover, pre-polymers having a higher viscosity may have a slower ability to react and condensation cure.

To analyze the above findings, a ratio termed AN/Visc. was defined in which the Amine Number (AN) of the elastomer was divided by its initial viscosity (Visc.), the resulting value being multiplied by 1000. Results of this analysis, values being rounded up, are presented in the following table in which the elastomers are presented in two series, first those being linear (LP), then the branched polymers (BP). In each series, the reactive condensation-curable amino-silicone elastomers are ranked by decreasing value of AN/Visc. ratio.

TABLE 3

| Sample | Silicone | Amine No.* | Viscosity (mPa · s) | AN/Visc. | Shampoo Resist |
|---|---|---|---|---|---|
| AG | KF-857 (LP) | 127 | 65 | 1954 | ≥130 |
| AD | GP-397(LP) | 116 | 130 | 892 | ≥110 |
| AE | GP-657 (LP) | 54 | 120 | 450 | ≥100 |
| AA | ATM 1322 (LP) | 101 | 250 | 404 | ≥65 |
| AJ | TSF 4703 (LP) | 62 | 1000 | 62 | ≥50 |
| AL | TSF 4708 (LP) | 38 | 1000 | 38 | ≥10 |
| AN | Xiameter ® OFX 8822 (LP) | 45 | 1500 | 30 | ≈20 |
| AH | Rhodorsil 21642 (LP) | 15 | 1400 | 11 | ≥10 |
| AM | Xiameter ® OFX 8630 (LP) | 25 | 3500 | 7 | ≥30 |
| AC | GP-145 (LP) | 11 | 1900 | 6 | ≈18 |
| AK | TSF 4707 (LP) | 15 | 7000 | 2 | ≥20 |
| AB | GP-34 (LP) | 3.3 | 3500 | 1 | ≥20 |
| AF | GP-846 (BP) | 110 | 30 | 3667 | ≥55 |
| AI | SF 1706 (BP) | 47 | 30 | 1567 | ≈20 |

As can be seen from Table 3, reactive condensation-curable amino-silicone elastomers having a linear structure seem to provide more shampoo resistance than branched counterparts having similar AN/Visc. ratios. However, it should be noted that the number of branched elastomers tested is not sufficiently large to be necessarily representative of the whole class of such polymers.

Similarly, though information on the average MW of the condensation-curable amino-silicones is scarce, it seems that samples prepared from pre-polymers having a relatively lower MW provided for greater shampoo resistance than pre-polymers having a relatively higher MW (hence higher viscosity). See for instance samples, AD and AE prepared from reactive condensation-curable amino-silicones having a MW of about 3,700, which successfully resisted at least 100 shampooing cycles, as compared to samples AB and AC, made of pre-polymers having respective MW of about 33,600 and 18,000, which only withstood approximately twenty shampooing. It is accordingly expected that silicones having much higher MW and viscosity, will be more and more unlikely to form shampoo resistant coats, as the MW or viscosity is increased.

Considering now the linear condensation-curable amino-silicone elastomers, it seems that pre-polymers having an AN/Visc. ratio of up to about 40 can provide semi-permanent coloring (or less if so desired). Elastomers having a higher ratio can provide for permanent coloring (see, for instance, samples AG, AD, AE, AA and AJ). It should be noted that the addition of curing agents (lacking in present example wherein condensation is mainly triggered by humidity) to complete the preparation of the intended coloring compositions is expected to further improve wash resistance (increasing the number of cycles where the OD is not less than 80% of baseline values).

Example 3: Emulsions Comprising Cross-Linkers for Coloring Keratinous Fibers

Materials

| Chemical Family/Function | Material Name | Supplier | CAS No. |
|---|---|---|---|
| Reactive Amino-Silicone Pre-Polymers | | | |
| Linear Polymer MW ~3,754 Amine Number 116 | GP-397 | Genesee | 68083-19-2 |
| Linear Polymer MW ~3,200 Amine Number 127 | KF-857 | Shin Etsu | |

| Chemical Family/Function | Material Name | Supplier | CAS No. |
|---|---|---|---|
| Monomer AminoAlkyl Silane Amine Number 370 | Dynasylan® SIVO 210 | Evonik | 919-30-2 13497-18-2 |
| Non-Reactive Silicone-Based Materials | | | |
| Amino-Silicone Oil Bis 3-aminopropyl tetramethyldisiloxane Amine Number ~800 | GP-967 | Genesee | 2469-55-8 |
| Decamethylcyclopentasiloxane | SID 2650-D5 | Gelest | 541-02-6 |
| Pigment Dispersants | | | |
| Organically modified Amino Polysiloxane | LPX 21879 | BYK | |
| Cross-Linkers and Other Curing Agents | | | |
| PolyCarbodiimide | Carbodilite Emulsion E-05 | Nisshinbo | |
| PolyCarbodiimide | V-02B | Nisshinbo | |
| Ethylsilicate oligomer | Dynasylan® 40 | Evonik | |
| Ethylsilicate oligomer | Ethylsilicate 48 Emulsifier | Colcoat | 11099-06-2 |
| Polyoxyethylene (20) sorbitan monooleate | Tween® 80 | Sigma-Aldrich | 9005-65-6 |
| Polyalkylenoxide Castor oil based siloxane | Silube® CO-J208 | Siltech | |

Preparation of Compositions

Samples BA to BE were prepared as described below. Unless otherwise stated all compositions had a pH of approximately 10.

Sample BA: 8 g of reactive amino-silicone pre-polymer (GP-397) were mixed with 8 g of reactive amino-silicone monomer (Dynasylan® SIVO 210, itself containing a mixture of three condensation-curable amino-silicone monomers) acting as cross-linker in the present composition. The mixture was added to 2 g milled slurry comprising sub-micronic particles of Cromophtal® yellow 3RT with BYK LPX 21879 (at a 1:1 w/w ratio), prepared as described above, and mixed on a Teflon® surface using a painting trowel. The mixture was then homogenized using IKA Ultra Turrax T25 at 25,000 rpm for 30 seconds, to obtain a colored paste. 0.18 g of the colored paste were diluted with 60 g of water. The diluted mixture was then sonicated using Qsonica Sonicator Q700 for 10 seconds at 80% amplitude to obtain a final coloring emulsion.

It is to be noted that Dynasylan® SIVO 210 (having an estimated Amine Number of 370) contains, according to its suppliers, a blend of three monomers: 3-aminopropyltriethoxysilane (CAS No. 919-30-2, generally present at 25% or more) having an Amine Number of 450, bis(triethoxysilylpropyl) amine (CAS No. 13497-18-2, generally present at more than 20%) having an Amine Number of 235 and 1-(3-(triethoxysilyl)propyl)-2,2-diethoxi-1-aza-2-silacyclopentane (CAS No. 1184179-50-7, generally present in the range of 1-5%) having an Amine Number of 263. These materials are individually available respectively as Dynasylan® AMEO from Evonik, SIB1824.5 and SIT8187.2 from Gelest and their respective effect can be separately assessed by replacing Dynasylan® SIVO 210 by any one of its constituents.

Sample BB: 6 g of reactive amino-silicone pre-polymer (GP-397) were mixed with 2 g of reactive amino-silicone monomer (Dynasylan® SIVO 210, herein serving as cross-linker to the polymer) and 2 g of decamethyl cyclopentasiloxane. The mixture was added to 2 g milled slurry comprising sub-micronic particles of Cromophtal® yellow 3RT with BYK LPX 21879 (at a 1:1 w/w ratio), prepared as described above, and mixed on a Teflon® surface using a painting trowel. The mixture was then homogenized as described above, to obtain a colored paste. 0.12 g of the colored paste was diluted with 60 g of water containing 0.06 g Tween® 80. The diluted mixture was shaken manually for a few seconds to obtain a homogenous emulsion. 0.1 g of Carbodilite Emulsion E-05 (cure accelerator) was added, with shaking for 10-15 seconds, to obtain a final coloring emulsion.

Sample BC: 6 g reactive amino-silicone pre-polymer (GP-397) were mixed with 2 g of reactive amino-silicone monomer (Dynasylan® SIVO 210, herein serving as cross-linker) and 2 g of decamethyl cyclopentasiloxane. The mixture was added to 2 g milled slurry comprising sub-micronic particles of Cromophtal® yellow 3RT with BYK LPX 21879 (at a 1:1 w/w ratio), prepared as described above, and mixed on a Teflon® surface using a painting trowel. The mixture was then homogenized as described above, to obtain a colored paste. 0.12 g of the colored paste were diluted with 60 g of water containing 0.06 g Tween® 80. The diluted mixture was shaken manually for a few seconds to obtain a homogenous emulsion. 0.1 g of Carbodilite Emulsion E-05 (cure accelerator) were added, with shaking for 10-15 seconds, to obtain a colored emulsion (emulsion I). In a separate container, 0.02 g of GP-967 cure accelerator were mixed with 6 g of water and shaken until a homogeneous emulsion (emulsion II) was obtained. 6.02 g of emulsion II were added to 60.19 g of emulsion I with shaking for 13-15 seconds, to obtain the final coloring emulsion. In a kit, emulsion I and emulsion II can be provided in separate compartments.

Sample BD: As for sample BB, but with reactive amino-silicone pre-polymer GP-397 (Genesee) replaced by KF-857 (Shin Etsu).

Sample BE: 7 g of reactive amino-silicone pre-polymer (GP-397) were mixed with 3 g milled slurry comprising sub-micronic particles of Cromophtal® yellow 3RT with BYK LPX 21879 (at a 1:2 w/w ratio), prepared as described above, and mixed on a Teflon® surface using a painting trowel. The mixture was then homogenized as described above, to obtain a colored paste. 0.2 g of the colored paste were diluted with 60 g of water. The diluted mixture was then sonicated using Qsonica Sonicator Q700 for 10 seconds at 80% amplitude to obtain a cross-linkable colored emulsion (emulsion I).

In a separate container, 0.1 g of Evonik® Industries ethyl polysilicate cross-linker Dynasylan® 40 were mixed with 6 g of water and 0.06 g of Silube® CO-J208 (a castor oil based siloxane, of Siltech Corporation, Canada, serving as emulsifier) and sonicated for 5 seconds at 30% amplitude to obtain cross-linker emulsion II.

6.02 g of emulsion II and 0.2 g of Carbodilite Emulsion E-05 were added to 60.2 g of emulsion I with shaking for 10-15 seconds, to obtain the final coloring emulsion. In a kit, cross-linkable emulsion I and cross-linking emulsion II can be provided in separate compartments.

Sample BF: 8 g of reactive amino-silicone pre-polymer (GP-397) were mixed with 2 g milled slurry comprising sub-micronic particles of Cromophtal® yellow 3RT with BYK LPX 21879 (at a 1:1 w/w ratio), prepared as described above, and mixed on a Teflon® surface using a painting trowel. The mixture was then homogenized as described above, to obtain a colored paste. 0.1 g of the colored paste were diluted with 60 g of water. The diluted mixture was then sonicated using Qsonica Sonicator Q700 for 10 seconds at 80% amplitude to obtain a cross-linkable colored emulsion (emulsion I).

In a separate container, 0.05 g of Evonik® Industries cross-linker Dynasylan® 40 and 0.05 g of Colcoat cross-linker Ethylsilicate 48 were mixed with 6 g of water and 0.06 g of Silube® CO-J208 (a castor oil based siloxane, of Siltech Corporation, Canada, serving as emulsifier) and sonicated for 5 seconds at 30% amplitude to obtain cross-linker emulsion II.

6.16 g of emulsion II and 0.2 g of "Carbodilite L" (Carbodilite L is a blend of 40 g carbodilite V-02B, 3 g BYK LPX 21879, 60 g Water) were added to 60.1 g of emulsion I with shaking for 10-15 seconds, to obtain the final coloring emulsion. In a kit, cross-linkable emulsion I and cross-linking emulsion II can be provided in separate compartments.

Coating of Keratinous Fibers with Amino-Silicone Emulsions

Coated samples were prepared by immersing tufts of untreated yak hair (2.5 g per tuft) in one of compositions BA to BF, respectively, for 45 seconds at ambient temperature, with gentle stirring. The samples were subsequently rinsed thoroughly in tap water at about 40° C., then dried for about 30 seconds with a Philips compact hair dryer. The drying was typically performed with hot hair blown from a distance of about 20 cm (providing for a temperature of about 50° C. on the hair surface). The hair was generally combed during the drying process to facilitate exposure of all fibers to the air flow, so as to shorten the drying step. However, it should be noted that while the temperature of the air flow can accelerate the evaporation of the volatile components (e.g., of the water carrier), it is not pivotal to the coating process according to the present teachings and hair samples dried with air blown at ambient temperature (circa 23° C.). provided similar results.

The resulting colored sample BA was observed to be glossy; sample BB was glossy, not sticky, and left no color residue on the fingertips after contact; sample BC and BD were glossy, not sticky, totally dry, and left no color residue on the fingertips after contact; sample BE was not sticky, and left no color residue on the fingertips after contact; sample BF was not sticky, totally dry and left no color residue on the fingertips after contact.

The colored sample was kept at ambient temperature for three weeks (sample BA) or one week (samples BB, BE); or for 3 days at 60° C. (samples BC, BD), then color fade was studied as previously described, by measuring after every 5 cycles the OD of each of the samples following various numbers of standard shampooing and drying treatments, which were performed up to 100 times (sample BA) or 50 times (samples BB, BC, BD, BE).

Results were analyzed as above, expressed as percentage of baseline OD, which was calculated for each sample. The number of shampoos each sample could withstand before undergoing a visible change in color (as confirmed by a measured OD smaller than 80% of baseline OD) is reported below.

Results

An OD of at least 80% of was retained by sample BA for up to about 70 washes; for samples BB, BC, BE for at least 40 washes; for sample BD for at least 50 washes.

As the results obtained, for instance, with samples BB and BD indicated that condensation-curable amino-silicone pre-polymer GP-397 (Genesee) can be replaced by KF-857 (Shin Etsu), further experiments were conducted suggesting that GP-397 can additionally be replaced by GP-657 and GP-145 (also of Genesee) to prepare compositions having similar desired effects. It should be noted that these outstanding results were obtained with low amounts of reactive amino-silicone pre-polymers in the final compositions being applied to the hair samples. Suitable coloration of hair samples of about 2.5 g and color permanency (as assessed by wash resistance) were obtained with final concentration of amino-silicone pre-polymers of less than 1 wt. % and even less than 0.5 wt. % of the coloring sample. As a suitable amount of ingredients in the coating composition is related to the quantity of hair to be coated (e.g., the surface area of the fibers), such concentrations are expected to increase in compositions of commercially relevant size (e.g., able to coat full head hairs of up to a few hundreds grams depending on hair length).

Example 4: Coloring of Dark-Colored Keratinous Fibers

Materials

Aryl modified polydimethylsiloxane (Siltech® E-2154, Siltech Corporation, Canada) Non-reactive amino-functional polydimethylsiloxane (Wacker Finish WR 1100, Wacker Chemie AG, Germany)

Sodium dodecyl benzenesulfonate (Sigma-Aldrich Co. USA, Cat. No. 28, 995-7)

Mica flakes (Pyrisma T30-20 Color Space Yellow, Merck, Germany)

Pentaerythritol tetraacylate (Sigma-Aldrich Co. USA, Cat. No. 408263)

Dynasylan® Hydrosil 2926 (Evonik® Industries AG, Germany)

Triethanolamine (Sigma-Aldrich Co. USA, Cat. No. 90279)

Isopropanol (Sigma-Aldrich Co. USA, Cat. No. W292912)

Aluminum silica coated pigments, Powdal 2900 (Schlenk, Germany)

Vacuum metallized passivated aluminum flake pigments AQ-4172 PA (Silberline, Germany)

Lithoflex® XA 40 01 Rich gold; Lithoflex® XA 40 02 Rich pale gold; and Lithoflex® XA 40 03 pale gold (Eckart, Germany)

Metallic flakes of Rich gold Bronze 12K and Aluminum 6150 (Manfong Fujian, China)

Equipment

Centrifuge: Z383 high speed, high capacity centrifuge (Labnet International Inc., USA)

Vortex: Vortex Genius 3 (IKA, Germany)

In previous examples, the hair color was modified from a lighter shade (e.g., yak white body hair) to a darker shade. Therefore the coloring treatment could be directly applied to the keratinous fibers without requiring any pre-treatment aimed to first reduce or eliminate the original color. As mentioned, in conventional hair coloring such color modifying pre-treatment involves penetration of bleaching chemicals into the hair shaft, a method negatively renowned for the resulting damage to the hair and the associated health concerns.

In the following, an alternative method and composition are proposed for the color modifying pre-treatment of hair achieving a similar effect of masking or reducing the visibility of an original relatively dark shade. While this method can also be applied to light shaded keratinous fibers, it is not essential when the desired end coloring is darker than the original color.

Coating of Dark Keratinous Fibers by Aluminum Flakes

Composition H was prepared, comprising passivated thin film aluminum flakes and a diluent, wherein the weight of components in grams is presented in Table 4:

TABLE 4

| Component | Function | Weight (g) |
|---|---|---|
| AQ-4172 PA 20% Aluminum pigment suspension in isopropanol | Aluminum pigment | 5 |
| (3-Glycidyloxypropyl) trimethoxysilane, GLYMO | Cross-linker | 1 |
| 99.9% Ethanol ABS AR anhydrous solution | Diluent | 94 |

Composition H was prepared as follows: 1 g of (3-Glycidyloxypropyl)trimethoxysilane (GLYMO) was added to 5 g vacuum metallized passivated aluminum flake pigments AQ-4172 PA under vigorous stirring in ethanol. The excess GLYMO silane was then removed by 3 centrifugation cycles with ethanol, using Z383 high speed, high capacity centrifuge (Labnet International Inc., USA) at 5000 RPM for 10 minutes. This process resulted in the coating of aluminum flake pigment with non-amino GLYMO silane.

Coloring composition I was prepared by re-suspending the GLYMO silane coated aluminum flakes of coloring composition H in ethanol to obtain a 20% aluminum pigment dispersion in ethanol.

Coloring compositions J and K were prepared, wherein the weight of components in grams is presented in Table 5:

TABLE 5

| | | Composition | |
|---|---|---|---|
| Component | Function | J | K |
| AQ-4172 PA 20% Aluminum pigment in isopropanol | Aluminum pigment | 1.5 | |
| Composition I: 20% Aluminum GLYMO coated pigment in ethanol | Aluminum pigment | | 1.5 |
| Amino-silicone GP-397 | Reactive terminal amino functional silicone polymer | 0.5 | 0.5 |
| 98% hexamethyldisiloxane | Diluent | 3 | 3 |

Coated samples J and K were prepared by immersing tufts of untreated Chinese dark human hair (2.5 grams per tuft) in compositions J and K, respectively, as described above for coating of yak hair.

Magnified images of the Chinese natural hair tufts coated with aluminum pigments were recorded using an Olympus® LEXT OLS4100 confocal laser scanning microscope, following 0, 2, 4, 10, 20, 30, 40, 50, 60, 70, 80 and 90 standard shampooing treatments using Shea Natural Keratin Shampoo and drying with a Philips Compact Hair Dryer.

Aluminum flake pigments blended with amino-silicone were found to completely coat dark hair. Due to their thickness (~50 nm-100 nm) and average longest dimension in the range of 2-20 μm, the vacuum metalized aluminum pigment were found to conform well to the shape of a hair surface, as confirmed by microscope analysis.

Figure 3:
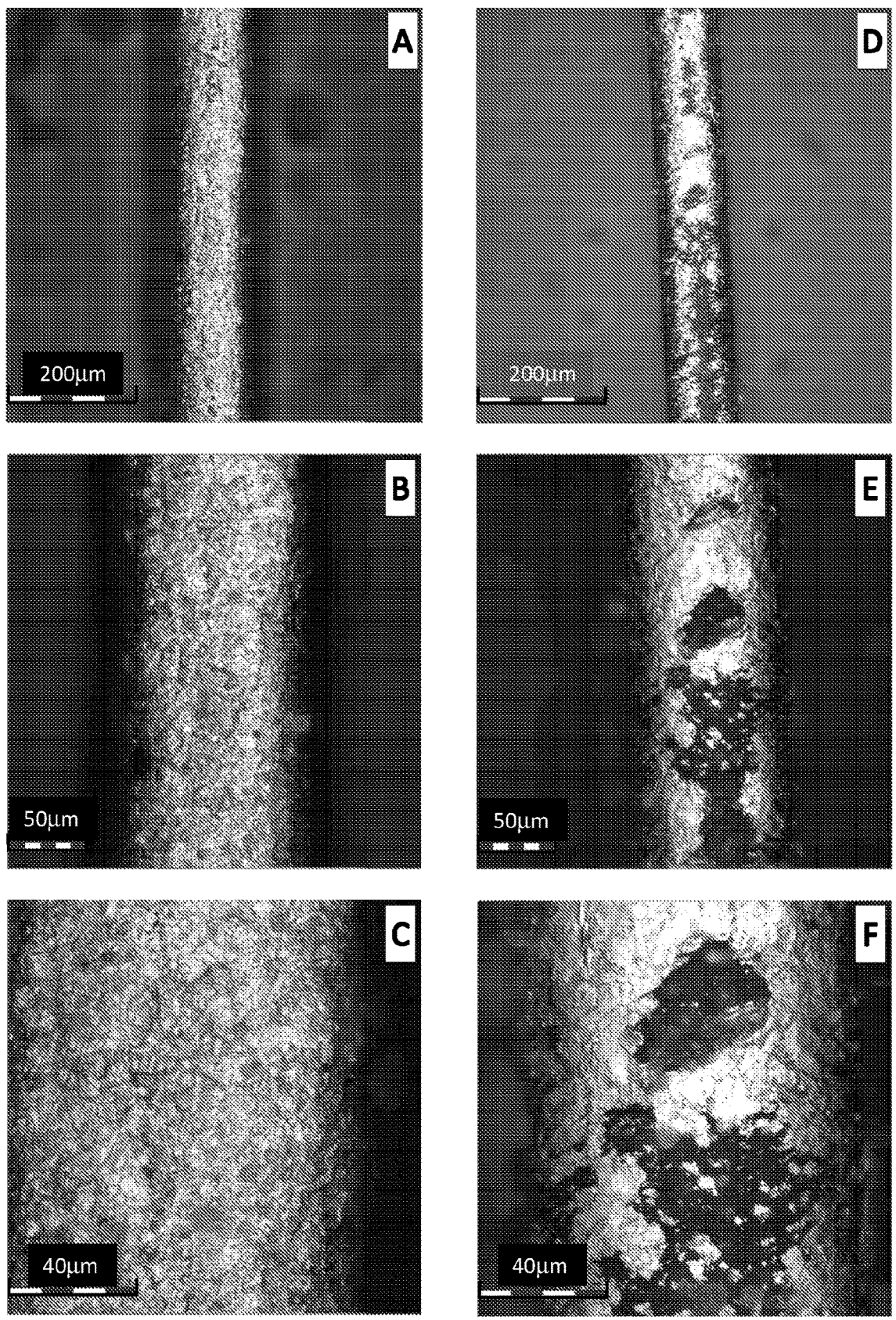

Confocal laser scanning microscope images of Chinese human hair coated with composition J are shown in FIGS. 3A to 3F, where panels A-C display coated fibers prior to washing (0) and panels D-F similar fibers after 30 washing and drying treatments, at which time the reduction in the extent of coating became detectable to the naked eye. FIGS. 3A and 3D images were captured at ×20 magnification, FIGS. 3B and 3E at ×50 and FIGS. 3C and 3F at ×100. While all hair coatings may include a small amount of uncoated spots each having small surfaces undetectable taken as a whole on the macroscopic level (see FIGS. 3A-3C), the amount of such clearings and their areas can increase with each shampoo until they reach a number and/or overall uncoated surface (see FIGS. 3D-3F) which becomes macroscopically detectable (e.g., to the naked eye) and detrimental to the desired coloring effect.

While for clarity these pictures show the coated patterns of relatively large metallic flake pigments, similar phenomena can be observed with fibers coated with pigments of sub-micronic size. Such images clearly illustrate the good correlation between the visual assessment of the hair color and reduction thereof after any predetermined number of shampoos, the measured OD (a decrease below 80% being detectable by the naked eye) and the microscopic analysis of hair fibers underlying such observations.

Coating of Dark Hair with Interference Pigment

Curable polymer-based primer composition L, an aqueous silicone emulsion comprising alkoxy silane and aminoethyl aminopropyl groups, as shown in Table 6, was prepared as follows. 6 g of Siltech® E-2154 (aryl-modified polydimethylsiloxane emulsion (50% in water)), 2 g of Wacker Finish WR 1100 (reactive amino-functional polydimethylsiloxane) and 250 mg of 20% w/w sodium dodecyl benzenesulfonate were mixed for about 30 seconds using a vortex. 4 g of mica flakes were added followed by an additional period of 30 seconds of mixing by vortex to obtain a milky suspension.

TABLE 6

| Component | Percentage of final composition (w/w) |
|---|---|
| Aryl modified polydimethylsiloxane emulsion 50% in water | 49 |
| Reactive aminoethylaminopropyl functional polydimethylsiloxane | 16 |
| 20 wt. % sodium dodecyl benzenesulfonate in water | 2 |
| Mica flakes | 33 |

Curable polymer-based coating composition M, as shown in Table 7, was prepared by suspending interference pigments (mica flakes) in an aqueous silicone oligomer capable of forming covalent bonds with primer solution L as follows. 6 g of mica pigment were added to 6 g of 1% w/w pentaerythritol tetraacylate in acetone and the suspension mixed for about 30 seconds using a vortex then allowed to evaporate for about 30 minutes in a chemical hood at ambient temperature to obtain a dry powder. 8 g Dynasylan® Hydrosil 2926 and 150 mg triethanolamine were then added to the dry powder and mixed for about 30 seconds by vortex.

TABLE 7

| Component | Percentage of final composition (w/w) |
|---|---|
| Mica flakes | 43 |
| Dynasylan ® Hydrosil 2926 | 56 |
| Triethanolamine | 1 |

Untreated tufts of European natural black hair were immersed in composition L for about 2 minutes at ambient temperature. The samples were subsequently rinsed thoroughly in tap water preheated to a temperature in the range of 35-40° C. The wet tufts were immersed for about 3 minutes in composition M, then removed from the composition and dried with a Philips compact hairdryer. Unless otherwise stated, each composition was applied to at least three tufts of hair.

Coating of Dark Hair with Metal Pigment

Curable polymer-based primer composition N, an aqueous silicone emulsion comprising alkoxy silane and aminoethyl aminopropyl groups, as shown in Table 8, was prepared as follows: 6 g of Siltech® E-2154 (aryl-modified polydimethylsiloxane emulsion (50% in water)), 2 g of Wacker Finish WR 1100 (reactive amino-functional polydimethylsiloxane) and 250 mg of 20 wt. % sodium dodecyl benzenesulfonate in water were mixed for about 30 seconds using a vortex.

TABLE 8

| Component | Percentage of final composition (w/w) |
| --- | --- |
| Aryl modified polydimethylsiloxane emulsion 50% in water | 75 |
| Reactive aminoethylaminopropyl functional polydimethylsiloxane | 25 |

Curable polymer-based coating composition O, as shown in Table 9, was prepared by suspending metal flakes in an aqueous silicone oligomer capable of forming covalent bonds with primer solution N, was prepared as follows: 0.7 g Bronze Rich gold 12K, 8 g Dynasylan® Hydrosil 2926 and 150 mg NaOH 1N were mixed with 0.5 g isopropanol and mixed for about 30 seconds by vortex.

TABLE 9

| Component | Percentage of final composition (w/w) |
| --- | --- |
| Rich gold bronze | 7.5 |
| Isopropanol | 5 |
| Dynasylan ® Hydrosil 2926 | 86 |
| NaOH 1N | 1.5 |

Untreated tufts of European natural black hair were immersed in composition N for about 2 minutes at ambient temperature. The samples were subsequently rinsed thoroughly in tap water preheated to a temperature in the range of 35-40° C. The wet tufts were immersed for about 3 minutes in composition O, then removed from the composition and dried with a Philips compact hairdryer. Unless otherwise stated, each composition was applied to at least three tufts of hair.

Interference pigments were found to add a layer having a thickness of about 0.5 µm to each hair fiber, while metal flakes added a layer having a thickness of up to 0.1 µm. Such increases are considered acceptable, and possibly even desirable. In view of their relatively greater thickness, the interference pigments behaved more rigidly than the relatively more flexible other "non-interference" metallic pigments. Hence, the ability of interference pigments to conform to the outer surface of fibers is expected to be relatively lower.

Example 5: Removal of Cured Coating Compositions from Keratinous Fibers

Materials

Tetra butyl ammonium fluoride (TBAF) 75% (Sigma-Aldrich Co., USA, Cat. No. 361399)

N-Octyl pyrrolidone (NOP) (Sigma-Aldrich Co., USA, Cat. No. 332186)

4-Dodecyl benzene sulfonic acid (DBSA) (Sigma-Aldrich Co., USA, Cat. No. 44198)

Tetrabutylammonium hydroxide pentahydrate (TBAH) 95% (Sigma-Aldrich Co., USA, Cat. No. 87741)

Isopropanol (Sigma-Aldrich Co., USA, Cat. No. Cat. W292912)

Dodecane (Sigma-Aldrich Co., USA, Cat. No. D221104)

Hexamethyl disiloxane (HMDS) (Gelest Inc., USA)

Equipment

Heraeus oven, UT 12 (Thermo Scientific, USA)

Unimax 1010 Digital Orbital Shaker (Heidolph, Germany)

LEXT OLS4100 confocal laser scanning microscope (Olympus Corporation, Japan)

Compact hair dryer (Philips, The Netherlands)

Methods

Coating Compositions

The following coating compositions were prepared using 1.3% w/w pigment, 1.3% w/w 2-ethylhexanoic acid, 10% w/w amino-silicone GP-397 and about 87% w/w HMDS:

Yellow coating, using yellow pigment P.Y. 83 (Cappelle Pigments NV, Belgium)

Green coating, using Heliogen® Green K8730 pigment (BASF, Germany)

Red coating, using Irgazin® Magenta 2012 pigment (BASF, Germany)

Blue coating, using Hostaperm Blue 15:3 (Clariant Int.)

Silver coating, using vacuum metallized passivated aluminum flake pigments AQ-4172 PA (Silberline Germany).

Coating Protocol

Coated samples of yak hair A, B, C and J (using green, yellow, magenta and silver coloring compositions, respectively) were prepared as described above. In addition, tufts of yak hair which were further bleached prior to coating with yellow coloring composition were prepared.

The samples were subsequently rinsed thoroughly in tap water at ambient temperature and then transferred to a Heraeus oven, UT 12 for 7 days at 60° C. and 95% RH, to cure the reactive polyaminosiloxane (e.g., by cross linking).

Removal of Coloring Composition

Three types of coloring removal solutions were prepared by dissolving the active ingredient in an appropriate solvent:

A) Organic fluoride salt (tetrabutyl ammonium fluoride (TBAF)) as active agent, at a concentration of 0.25%, 0.5%, 1% or 2% (w/w) in dipolar aprotic solvent (N-octyl-pyrrolidone (NOP)), B) Acidic active agent (dodecyl benzene sulfonic acid (DBSA)) at a concentration of 0.5%, 1%, 2% or 4% (w/w) in non-protic solvent (dodecane);

C) Basic active agent (tetrabutyl ammonium hydroxide (TBAH)) at a concentration of 1%, 2% or 4% (w/w) in protic solvent (isopropanol).

Coated samples were immersed in the coloring removal solutions of the example and maintained under slow orbital shaking (50 rpm) at ambient temperature. Samples were removed from coloring removal solutions after a period of time (immersion time) as specified in Table 10 below, and either not subjected to shampoo or subjected to a single standard shampooing treatment with Shea Natural Keratin Shampoo, as specified in Table 8. Samples were then dried with a Philips compact hair dryer at a temperature of 50-60° C. as perceived on the hair surface.

Evaluation of colorant removal was based on visual inspection and by use of Confocal Laser Scanning Microscope (Olympus® LEXT OLS4100).

Results

Results are presented in Tables 10 to 13 below and in FIGS. 4D to 4F. In the tables, ++ indicates complete removal of coloring composition, + indicates partial removal and − indicates no visible change, a single asterisk indicating that such findings result from visual observations with a naked eye and two asterisks indicating that such visual findings were confirmed by laser scanning microscopy).

Figure 4C:
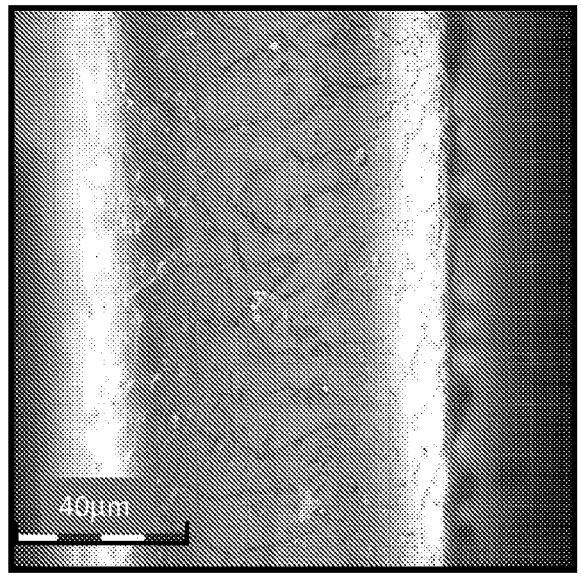
Figure 4D:
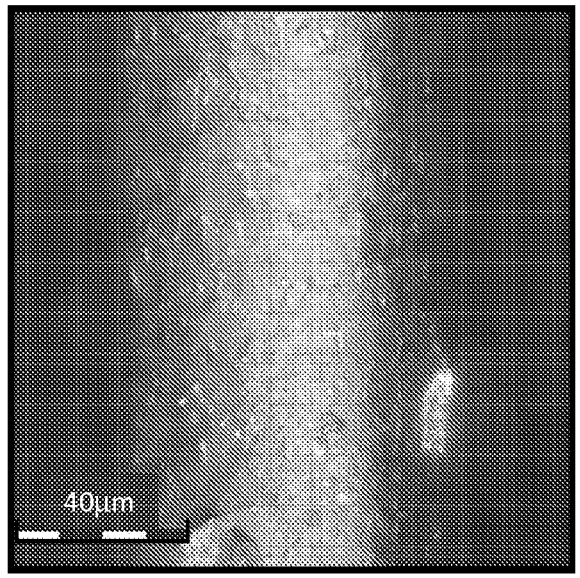
Figure 4E:
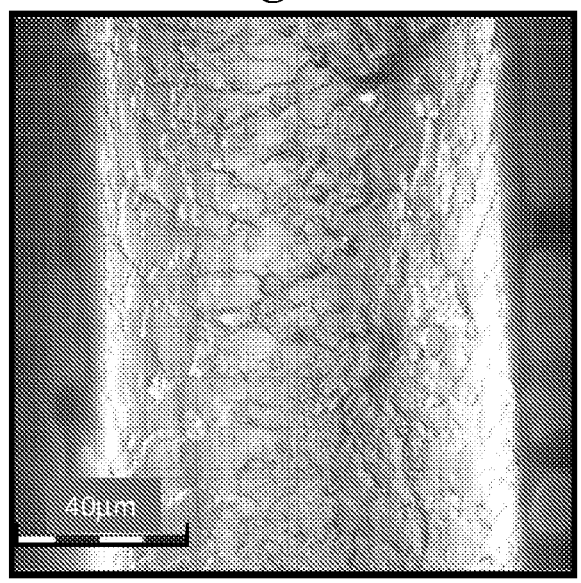
Figure 4F:
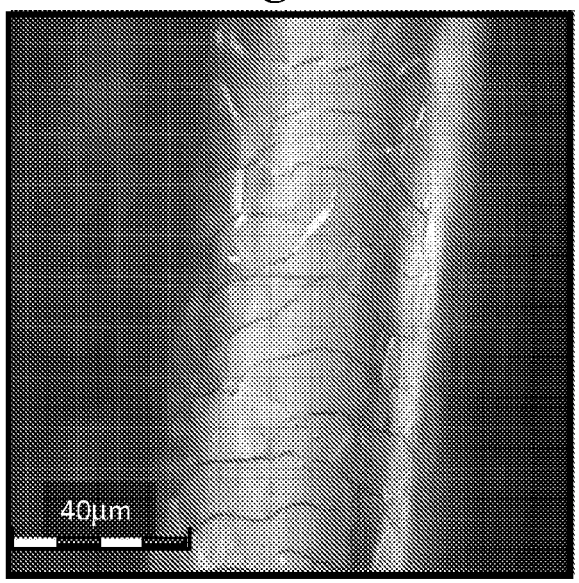

Table 10 and FIGS. 4D and 4F present results obtained for unbleached samples colored by pigment Hostaperm Blue 15:3 after immersion in coloring removal solutions comprising TBAF or DBSA for different immersion times. FIG. 4C shows a fiber colored with same pigment before the removal procedures.

TABLE 10

| Active ingredient wt. % | Solvent | No. of shampoos | Immersion time | Results |
|---|---|---|---|---|
| TBAF 2% | NOP | 0 | 5 mins | ++** |
| TBAF 1% | NOP | 0 | 5 mins | ++** |
| TBAF 0.5% | NOP | 0 | 30 mins | ++** |
| TBAF 0.125% | NOP | 1 | 30 mins | −** |
| DBSA 4% | Dodecane | 1 | 10 mins | ++** |
| DBSA 2% | Dodecane | 1 | 10 mins | ++** |
| DBSA 1% | Dodecane | 1 | 20 mins | +* |
| DBSA 0.5% | Dodecane | 1 | 20 mins | −** |

As shown in Table 10, complete removal of coloring composition was achieved with an immersion time of 5 minutes in coloring removal solutions comprising at least 1 wt. % TBAF solution, while 30 minutes immersion time was required for complete removal in solutions comprising 0.5 wt. % TBAF. No observable visible changes were detected with solutions comprising only 0.125 wt. % TBAF, even after 30 minutes immersion time and even with the mechanical rubbing a shampoo would additionally supply to facilitate the removal.

For coloring removal solutions comprising DBSA, complete removal of coloring composition was achieved with an immersion time of 10 minutes in solutions comprising at least 2 wt. % DBSA. A coloring removal solution comprising 1 wt. % DBSA provided partial removal even after 20 minutes immersion time followed by a shampoo. No observable visible changes were detected with solutions comprising 0.5 wt. % DBSA, even after 20 minutes immersion time followed by a shampoo.

Table 11 presents results obtained for samples which were bleached prior to coloring with pigment yellow (P.Y. 83) after immersion in coloring removal solutions comprising TBAF, DBSA or TBAH for different immersion times.

TABLE 11

| Active ingredient wt. % | Solvent | No. of shampoos | Immersion time | Results |
|---|---|---|---|---|
| TBAF 2% | NOP | 0 | 5 mins | ++** |
| TBAF 1% | NOP | 0 | 5 mins | ++** |
| TBAF 0.5% | NOP | 1 | 10 mins | +* |
| TBAF 0.25% | NOP | 1 | 10 mins | +* |
| TBAF 0.125% | NOP | 1 | 30 mins | −** |
| DBSA 4% | Dodecane | 1 | 10 mins | ++** |
| DBSA 2% | Dodecane | 1 | 10 mins | ++** |
| DBSA 1% | Dodecane | 1 | 20 mins | +* |
| DBSA 0.5% | Dodecane | 1 | 20 mins | −** |
| TBAH 4% | Isopropanol | 1 | 20 mins | ++** |
| TBAH 4% | Isopropanol | 1 | 10 mins | +* |
| TBAH 2% | Isopropanol | 1 | 20 mins | +* |
| TBAH 2% | Isopropanol | 1 | 10 mins | −** |
| TBAH 1% | Isopropanol | 1 | 20 mins | −** |

As shown in Table 11, results obtained with yak hair which was bleached prior to coloring were similar to those obtained with unbleached, colored yak hair. Complete removal of color was achieved with an immersion time of 5 minutes in coloring removal solutions comprising at least 1 wt. % TBAF. No observable visible changes were detected with solutions comprising 0.125 wt. % TBAF, even after 30 minutes immersion time.

For coloring removal solutions comprising DBSA, complete removal of coloring composition was achieved with an immersion time of 10 minutes in solutions comprising at least 2 wt. % DBSA. No observable visible changes were detected with solutions comprising 0.5 wt. % DBSA, even after 20 minutes immersion time.

For solutions comprising TBAH, complete removal of coloring composition was achieved with an immersion time of 20 minutes with solutions comprising 4 wt. % TBAH.

Tables 12 and 13 present results obtained for samples colored with green, red and silver pigments, following treatment with coloring composition removal solution, wherein the samples were removed from coloring removal solution after 20 minutes (Table 12) and after 5 minutes (Table 13).

TABLE 12

| Active ingredient wt. % | Removal solvent | Sample Green (A) | Red (C) | Silver (J) |
|---|---|---|---|---|
| 2% TBAF | NOP | ++ | ++ | ++ |
| 1% TBAF | NOP | ++ | ++ | ++ |
| 0.5% TBAF | NOP | ++ | ++ | ++ |
| 4% DBSA | Dodecane | ++ | ++ | ++ |
| 2% DBSA | Dodecane | + | ++ | + |

TABLE 13

| Active ingredient wt. % | Removal solvent | Sample Green (A) | Red (C) | Silver (J) |
|---|---|---|---|---|
| 2% TBAF | NOP | ++ | ++ | ++ |
| 1% TBAF | NOP | + | ++ | ++ |
| 4% DBSA | Dodecane | ++ | ++ | ++ |
| 2% DBSA | Dodecane | + | + | ++ |

As shown in Table 12, after 20 minutes in coloring composition removal solution, complete removal of coloring composition was seen from all samples tested with each of the solutions of TBAF used. Complete removal of coloring composition was also seen from all samples tested with 4 wt. % DBSA solution and from sample C with 2 wt. % DBSA. Partial removal of coloring composition was seen from samples A and J with 2 wt. % DBSA solution.

As shown in Table 13, after 5 minutes in 2 wt. % TBAF solution, complete removal of coloring composition was seen from all samples tested. After 5 minutes in 1 wt. % TBAF solution, complete removal of coloring composition was seen from samples C and J, and partial removal was seen from sample A. After 5 minutes in 4 wt. % DBSA solution, complete removal of coloring composition was seen from all samples tested. After 5 minutes in 2 wt. % DBSA solution, complete removal of coloring composition was seen from sample J and partial removal from samples A and C.

FIG. 4 shows ×100 magnification confocal laser scanning images of (C) uncoated yak hair, (D) yak hair coated with a coloring composition (sub-micronic Hostaperm Blue 15:3), (E) the hair as shown in (D) followed by treatment with a coloring removal solution comprising TBAF or (F) with a coloring removal solution comprising DBSA.

FIG. 4A is a schematic illustration of the external surface of a native hair fiber displaying hair scales; such as appearing in the uncoated sample shown in FIG. 4C and in the decolored samples shown in FIGS. 4E and 4F.

FIG. 4B is a schematic illustration of the external surface of a hair fiber coated with sub-micronic pigments or with pigment flakes; such as appearing in the colored pigment coated sample shown in FIG. 4D.

As seen in FIGS. 4D-4F virtually no scale lifting or crumbling of the cuticle scale edges was observed as compared to the uncoated hair. Clean cuticle edges were seen after complete removal of the pigment.

Similar decoloring experiments were successfully performed using an alternative fluoride salt, namely RonaCare® Olaflur by Merck KGaA, and the following combinations of decuring agents or resulting in a decuring agent: (TBAB+KOH), (TBAC+KOH) and (Luviquat® Mono CP AT1+Mg(OH)$_2$). Luviquat® Mono CP AT1 is an organic phosphate salt purchased from BASF Care Solutions which was shown to form a suitable decuring agent in combination with inorganic base magnesium hydroxide.

The following solvents were also tested and found suitable: methyl isobutyl ketone (MIBK), methyl phenyl ester (MPE), Propionitrile, Tert-butyl alcohol, tetrahydrofuran (THF), Toluene and Xylene. Detailed results are not shown, but a successful decoloring with these additional decuring agents and/or solvents and mixtures thereof means that the colored coat was removed within less than 30 minutes (typically within 5-10 min) with concentrations of decuring agents of less than 15 wt. %, generally between 1 wt. % and 10 wt. %.

Furthermore, representative decoloring solutions were supplemented with thickening agents to form creamy preparations that were as efficient as their respective "unthickened" controls. The thickening agents tested in the present study included glyceryl tristearate, an hydroxypropyl methylcellulose (Benecel™ K200M by Ashland), a fluoropolymer (Zonyl® MP1300 by DuPont), a modified polypropylene wax (Micropro 600VF by Micro Powders) and a micronized polyethylene (Micropoly® 220L by Micro Powders). All successfully yielded thickened formulations at concentrations in the range of 0.5 wt. % (for Benecel™ K200M) up to 40 wt. % (for Micropoly® 220L) by weight of the decoloring cream.

Example 6: Effect of Cationic Shampoos Following Coloring of Keratinous Fibers Cationic shampoo consisting of 3% (w/w) aqueous solution of cationic guar was prepared by adding 30 g cationic guar (N-Hance BF 17, Ashland Inc., USA) to 970 g water, with stirring using a magnetic stirrer for 1 hour until the guar was fully dissolved. The pH of the solution was measured and found to be 5.0.

Samples of yak white body hair were colored with composition AD as defined in Table 2, Example 2, above.

The initial OD (0 shampoos) following application of the coloring composition was measured after 1 hour at ambient temperature, as described above.

Sample hair tufts were wetted with water and a few drops of shampoo applied. The hair tuft was massaged gently 4 times with the shampoo. The hair tufts were subsequently rinsed thoroughly in tap water at about 40° C., then dried for 30 seconds with a Philips compact hair dryer. The process was repeated, and the OD measured after every 5 shampoos, for 15 shampoos. Results are presented in Table 14.

TABLE 14

| No. of Shampoos | OD | % variation |
|---|---|---|
| 0 | 1.116 | 0.0 |
| 5 | 1.110 | 0.5 |
| 10 | 1.100 | 1.4 |
| 15 | 1.100 | 1.4 |
| 20 | 1.106 | 0.9 |

As shown in Table 14, almost no variation in optical density was seen after 20 washes with a cationic shampoo. For comparison, washing with an anionic shampoo or nonionic shampoo during the same initial period of time following coloring, while the amino-silicone has not yet fully cure, proved deleterious to the stability of the coat on fibers. Namely, the OD monitored after washing with such non-cationic shampoos dramatically decreased after only a few washes (i.e. the OD dropped below 80% of baseline in no more than 3 washes).

A commercially available shampoo (TRESemmé Perfectly (un)Done cationic shampoo) was found to provide similar results and was used in additional experiments where rinsing with a cationic shampoo was desired.

Example 7: Differential Scanning Calorimetry (DSC) Study

Coloring Composition 8 g of reactive amino-silicone (GP-397, Genesee) were added to 2 g of milled slurry comprising sub-micronic pigment particles of Cromophtal® Yellow 3RT with BYK LPX 21879 as dispersant, prepared as described above, and mixed on a Teflon® surface using a painting trowel. The mixture was then homogenized using IKA Ultra Turrax T25 at 25,000 RPM for 30 seconds, to obtain a colored paste. 0.2 g of the colored paste were diluted with 60 g of distilled water. The diluted mixture was then sonicated using Qsonica Sonicator Q700 for 10 seconds at 80% amplitude to obtain a colored emulsion.

Coating of Keratinous Fibers

Coated sample was prepared by immersing tufts of untreated Chinese black hair (2.5 g per tuft), for 45 seconds at ambient temperature, with gentle stirring. The sample was subsequently rinsed thoroughly in tap water at about 40° C., then dried for 30 seconds with a Philips compact hair dryer.

Three days after the coloring, the hair was cut into small pieces (about 2 mm long) using regular scissors. For each measurement, about 10 mg of hair pieces were placed in a 100 μl aluminum DSC crucible. Distilled water was added to fill the crucible using a pipette. The crucible was sealed and allowed to stand for 12 hours at room temperature.

The ON moisture equilibrated samples were placed in a Differential Scanning calorimeter DSC Q200 (TA Instruments, USA) and DSC measurements were carried out. Specifically, the samples were first heated to and maintained at 80° C. for 5 minutes to allow thermal equilibration. Then, while data acquisition and storage were activated, the samples were heated to 300° C. at a rate of 20° C./min.

The stored data was then used to obtain a DSC curve for the sample. The DSC curve of each sample was compared to a reference DSC curve obtained in the same way for uncolored Chinese black hair from the same hair batch. An additional sample was first colored as described, then decolored as above-detailed with 2% TBAF. All samples displayed similar patterns in the DSC curve. Therefore, it may be concluded that the coloring process as described herein, as well as the coloring removal one, maintains integrity of the hair. For comparison, hair colored by a conventional oxidative chemistry resulted in a significant shift in the DSC pattern, as compared to the uncolored reference.

Example 8: Elemental Analysis of Coated Hair

Analysis of hair samples coated by the present method using scanning electron microscope (SEM) Energy-dispersive X-ray spectroscopy (EDS) revealed in addition to carbon, oxygen and nitrogen, an appreciable percentage of silicone atom (typically >10% by weight of all elements) attributed to the amino-silicone elastomer coating the hair fibers and attached thereto. Analysis was performed on a Crossbeam 340 ZEISS/Gemini SEM microscope under the following experimental conditions: energy 5 KV; Apertures 120; working distance 5 mm. The results reported below are average of at least 4 repeats.

A first control of native/uncoated European hair revealed, as expected, an absence of silicone signal with baseline value of 0.2%. A sample of the same hair colored according to the present teachings indicated the presence of about 18% of silicone. These results demonstrate that the presence of a silicone film on hair coated according to the present teachings can be detected by SEM-EDS.

The person skilled in the art of chemical analysis can readily appreciate that additional techniques may allow similar detection of features characterizing the polymers of the coating compositions. Mass spectrometry techniques, in particular soft ionization technique such as matrix-assisted laser desorption time-of flight mass spectrometry (MALDI-ToF-MS) may additionally provide unique information related to polymer end-groups and branching structure, as well as establishing the molecular mass distribution of the studied materials.

Example 9: Coloring with Combinations of Emulsions

In previous examples, coloring of hair samples was performed using a single composition of condensation-curable amino-silicone pre-polymers comprising pigment particles of a unique shade. In the present study, such coloring emulsions are considered and used as the "primary colors" (e.g., yellow, red, blue, black) of a color palette. In other words, two or more pigmented emulsions of amino-silicone pre-polymers, each providing for a different primary color are combined so as to provide a wider range of coloring options.

The condensation-curable amino-silicone emulsions were prepared as described for sample BC of Example 3, with three different sub-micronized pigments: Hostaperm® Blue B2G and Hansa Yellow 10G, both by Clariant, and Paliotol® Yellow D 1155, by BASF. The combinations of the formulations, each comprising a distinct pigment, so prepared are presented in Table 15. The combinations are described in weight percent of each pigmented emulsion per the total weight of the combination.

TABLE 15

| Combination No. | Hostaperm ® Blue B2G | Hansa Yellow 10G | Paliotol ® Yellow D1155 |
|---|---|---|---|
| 1 | 50 wt. % | 50 wt. % | 0 wt. % |
| 2 | 75 wt. % | 25 wt. % | 0 wt. % |
| 3 | 25 wt. % | 75 wt. % | 0 wt. % |
| 4 | 50 wt. % | 0 wt. % | 50 wt. % |
| 5 | 75 wt. % | 0 wt. % | 25 wt. % |

All combinations of the individual emulsions, prepared as detailed in Example 3, resulted in coloring compositions having different greenish shades. Yak hair tufts were dipped in each of the greeny emulsions for 45 seconds while gently stirring. The hair sample were then washed with tap water at about 37° C. and dried with a hair dryer, yielding a variety of green colored hair.

These results support the suitability of the present compositions to serve in hair coloring methods wherein the end-color can be personally customized for each subject, in a manner comparable to the multitude of end-colors in a digitally printed ink image which results from a limited number of initial colors.

Example 10: Repeated Coatings

In previous examples, coloring of hair samples was performed using a single application of one or more compositions of condensation-curable amino-silicone pre-polymers, each comprising pigment particles of one or more colors. Such experiments resulted in the formation of a single amino-silicone film upon the coated hair. In the present study, similar coloring steps are repeated, the emulsions of the first and second repeat each providing for a separate amino-silicone film. While the pigments used during a repeat coloring can provide for the same color (e.g., so as to modify its intensity), different colors were used in the present example for each repeat, so as to facilitate the demonstration.

Yak hair was coated with a first condensation-curable amino-silicone emulsion prepared substantially as described for sample BA of Example 3. This first emulsion was prepared using a colored paste comprising 50 wt. % GP-397, ~16.7 wt. % Dynasylan® SIVO-210, ~16.7 wt. % decamethyl cyclopentasiloxane (D5), ~8.3 wt. % Paliotol® Yellow 1155 (BASF) and ~8.3 wt. % BYK LPX 21879, the paste being emulsified prior to coloring in distilled water including Tween® 80 and Carbodilite Emulsion E-05, as previously detailed. The pH of the final coloring emulsion applied to the hair sample was of about 10.

The hair sample was dipped in the yellow color emulsion for 45 seconds while gently stirring. The sample was then washed with tap water at ambient temperature and dried with a hair dryer, yielding yellow colored hair. The colored hair sample was assessed using a spectrophotometer (X-Rite 939, of X-Rite Inc., USA) able to translate a color into three variables plotted along the three axis of a standardized color space known as CIE L*a*b*. The illumination used was D65 and the standard observer was set at 10°. The L*a*b* values of the dried yellow colored hair were found to be: 77.00, −6.60, and 60.47, respectively.

A second emulsion was similarly prepared wherein Paliotol® Yellow 1155 (BASF) was replaced by PV Fast Orange H2GLS (Clariant). The pH of the final coloring emulsion applied to the hair sample was of about 10. The dry hair sample, already colored in yellow by the first emulsion, was dipped in the orange color emulsion for 45 seconds while gently stirring. The sample was then washed with tap water at ambient temperature and dried with a hair dryer, yielding orange colored hair. The L*a*b* values of the dried now orange colored hair were found to be: 63.03, 31.88, and 62.87, respectively.

These results support the suitability of the present method to apply more than one film of amino-silicone on the hair fiber. This can be used to modulate the intensity of a shade of a first coat and/or to change the final color. This may prove advantageous if the subject coloring his/her hair wishes more flexibility with respect to the desired end-color, being able to modulate the "intermediate" results obtained from a first coating by a second coating. Moreover, it may permit selectively coating different portions of a multitude of hair fiber with different colors.

Example 11: Removal of Repeated Coatings

In the present example, the removal protocol was applied on hair fibers previously coated in two coloring steps, each step having resulted in a distinct amino-silicone film providing for a different color.

Yak hair was repeatedly coated, first with a condensation-curable amino-silicone emulsion comprising a yellow pigment and secondly with a similar coat comprising an orange pigment, as described in Example 10. Three types of coloring removal solutions were prepared by dissolving representative decuring agents in exemplary solvents, to yield the following:

A) 2 wt. % TBAF in N-octyl-pyrrolidone (NOP), representing a fluoride salt in a dipolar aprotic solvent;

B) 4 wt. % DBSA in dodecane, representing an acidic decuring agent in a non-protic solvent; and C) 4 wt. % TBAH in tert-butyl alcohol, representing a basic decuring agent in a protic solvent.

The colored hair tufts were placed in a mixing bowl and covered with about 5 ml of the coloring removal solutions. The tufts were thoroughly brushed with the aid of a dye brush with the removal solution to ensure their complete coverage thereby. Samples were taken out of the coloring removal solutions after 5 minutes rinsed thoroughly with tap water at about 35-40° C. The samples were subjected to a single standard shampooing treatment with Shea natural keratin shampoo (Gilam Cosmetics Ltd., Israel) and dried for approximately 30 seconds with a hair dryer. The efficacy of the removal of the double-coat was assessed by visual inspection of the dried hair tufts. All tested removal solutions were found efficacious within 5 minutes, suggesting that the removal solutions as herein disclosed as not particularly limited to single film coated fibers.

Example 12: Coloring Form

While in previous examples, the coloring or coating compositions, also simply referred to as the amino-silicone emulsions, generally displayed prior to curing a relatively low viscosity comparable to water, the present study demonstrates the ability to prepare similar compositions, but at an elevated viscosity. Such gel-like formulations are believed to have a longer contacting time with the hair to be coated than their non-thickened counterparts.

An amino-silicone blend was prepared by mixing condensation-curable amino-silicone monomers of Dynasylan® Sivo 210 (73 wt. %) with amino-silicone oils (GP-967 and GP-965, respectively at 20 wt. % and 7 wt. % of the total blend). 0.2 g of this first oily phase blend were added to 60 ml of aqueous forms. In a first reference sample, the amino-silicone blend (ASB) was added to plain distilled water (resulting in an emulsion having a pH of about 10). In additional samples, the water carrier was first supplemented with thickening agents, the ASB being subsequently added to an aqueous carrier having a gel form. A first thickened aqueous carrier was prepared by adding 0.5 wt. % Polyquaternium 7 (PQ-7) and 0.1 wt. % Polyquaternium 10 (PQ-10), per weight of distilled water. The Polyquaternium nomenclature is as assigned by the Cosmetic, Toiletry and Fragrance Association (CTFA) to most cationic conditioning polymers. PQ-7 is a poly(acrylamide-co-diallyl-dimethyl-ammonium chloride) copolymer and PQ-10 is a quaternized hydroxyethyl cellulose, both supplied by Dow. A second thickened aqueous carrier was prepared by further adding 0.1 wt. % Benecel™ K200 (an hydroxypropyl methylcellulose supplied by Ashland) to previous 0.5 wt. % PQ-7 and 0.1 wt. % PQ-10. A third thickened aqueous carrier was prepared by adding higher amounts of thickening agents, namely 0.5 wt. % Benecel™ K200, 0.5 wt. % PQ-10 and 2.5 wt. % PQ-7, per weight of distilled water. The various thickeners of the different mixtures were generally added one at a time under stirring conditions, as soon as the previous one(s) was/were evenly dissolved. The thickened samples yielded a pH of about 10.

All three thickened samples and aqueous control were manually shaken with the oil phase mixture to obtain four types of amino-silicone emulsions, derived from the same initial blend of materials. The viscosity of the reference sample (ASB in water) and of the thickened samples was measured at 25° C. using a Haake™ Mars™ III Rheometer with Spindle—C60 at a shear rate of 30 sec$^{-1}$. While the reference sample had a viscosity of about 0.89 mPa·s, the thickened counterparts respectively displayed a viscosity of about 20.1 mPa·s (0.5 wt. % PQ-7+0.1 wt. % PQ-10), a viscosity of about 56.7 mPa·s (0.5 wt. % PQ-7+0.1 wt. % PQ-10+0.1 wt. % Benecel™ K200M) and a viscosity of about 2,000 mPa·s (2.5 wt. % PQ-7+0.5 wt. % PQ-10+0.5 wt. % Benecel™ K200M). While for the sake of feasibility testing, the coating compositions were prepared without any coloring agent, it is expected that similar thickening can be obtained in presence of a pigment when coloration is desired.

The zeta potential of the reference sample emulsified in plain water was measured using a Zetasizer Nano Z (by Malvern Instruments) with a folded capillary cell DTS1070, and found to be of +4 mV. The oil phase blend, prior to its emulsification with the various aqueous carriers was analyzed by Differential Scanning calorimetry (DSC). The sample was tested between −80° C. and +80° C. at a heating rate of about 10° C./minute. The results were plotted in terms of heat flow (J/s) versus temperature (° C.) over the scanned range. As expected from materials lacking a sufficiently cross-linked network, a plotted flat curve indicated the absence of a glass transition temperature.

The average viscosity of the oil phase blend prior to emulsification was measured using a Haake Mars™ rheometer (geometry DG41) at a shear rate of 1 sec$^{-1}$, and found to be 6.1 mPa·s, demonstrating low viscosity of the oil phase.

Example 13: Bleach Resistance

It was already demonstrated that hair samples colored according to the present disclosure are resistant to a high number of shampooing cycles, to an extent allowing classifying coloring methods according to some embodiments of the present disclosure as permanent coloring. While shampooing can be considered as a chemical treatment of the hair fibers, it is typically intended to be a gentle one, not significantly damaging the hair, if at all. In the present study colored hair samples were subjected to a harsher chemical treatment, commonly used in the field and feared for the severe damages it causes, namely hair bleaching.

Hair tufts colored with a pigment-embedded amino-silicone emulsion as described herein were tested as follows. First, yak hair tufts were colored with an emulsion prepared substantially as described for sample BC of Example 3, the pigment now being Heliogen Blue D 7079 (BASF). The hair samples were dipped in the blue color emulsion (having a pH of about 10) while gently stirring for 45 seconds at ambient temperature. Following the coloration, the hair was washed with tap water and dried as previously detailed. Hair samples were allowed to fully cure before being subjected to the bleaching test.

Reference samples were prepared by coloring yak hair of a same source with a commercially available blue hair coloring product (Midnight Blue, La Riche, UK). The coloring of the reference samples was performed according to manufacturer's instructions, the semi-permanent color being brushed onto the hair and allowed to properly cover the hair fibers for 30 minutes. Following the reference coloration, the hair was washed with tap water and dried as previously detailed.

A bleaching composition was prepared by mixing in a coloring bowl: 20 g of hydrogen peroxide cream (L'Oréal Oxidant Cream (9%)) with 4 ml of a solution of ammonium hydroxide (at 25 wt. % concentration). Mixing was conducted with a coloring brush until a homogeneous viscous cream was obtained. The bleaching cream was then applied on the hair samples colored as contemplated herein or using commercially available reference product. Bleaching was allowed to proceed for 30 minutes at room temperature. The bleaching cream was then washed off from the hair samples, which were abundantly rinsed with tap water and dried with a hair dryer.

The OD of the various hair samples before and after bleaching was measured with a spectrophotometer using a cyan filter. The baseline OD for the reference colored by a commercial product was of 1.304, while the baseline OD for the hair samples colored according to the present teachings was of 1.650. The post-bleaching OD of the reference was of 1.048, whereas the post-bleaching OD of the inventive samples was of 1.696. These results first illustrate the strong coloring effect that can be achieved using the present method and compositions, the baseline OD of the inventive sample being about 27% higher than the OD of the commercial reference. Secondly, while the commercial product fails to maintain baseline value following bleaching, the OD of the bleached reference corresponding to about 80% of the unbleached reference, the OD of the hair samples coated with the inventive coloring compositions remained unaffected by this process.

As no visible changes in color are detected in the samples prepared by the present methods, when subjected to bleaching, the coatings formed with the present compositions are deemed suitable to protect the hair from harsh chemical treatment. It is therefore expected that such amino-silicone films can also afford protection of the hair fibers against milder chemical exposure (e.g., low concentrations of disinfecting agents found in swimming pools etc.).

Example 14: Hair Styling

Hair coated according to the present teachings can undergo further hair styling. Some hair styling processes may constitute a physical stress (i.e. heat and strokes of hair ironing), while others are considered to subject the hair to a chemical stress. Hair tufts colored with a pigment-embedded amino-silicone emulsion comprising Paliotol® Yellow D 1155, by BASF, prepared as described in Example 9, were tested as follows.

Hair Ironing

Following the coloration, the hair was washed with a cationic shampoo, rinsed, combed and dried as previously detailed. The dried colored hair tufts were then ironed at 140° C. for 10 strokes, using a BaByliss Pro™ ironing machine by BaByliss® Sarl, France. The resulting samples of ironed hair were found to have a straightened appearance, supporting the suitability for hair colored according to the present teachings to undergo further hair styling.

Permanent Curling

Hair samples colored, washed with a cationic shampoo, rinsed, combed and dried as previously detailed, were rolled over a 10 cm diameter roll to imitate professional hair perming rolls. The tip of the hair fibers was adhered to the rod to maintain the curled position of the fibers during the perming procedure which was carried out with a commercially available set (such as, Dulcia Advanced formula enriched with Ionène G, by L'Oréal SA, France). Ten drops of first step Dulcia G 0 perming composition were applied on the rolled hair, so as to fully cover all hair fibers. After 8 minutes of perming, the hair samples (still rolled on the rod) were abundantly rinsed with tap water. Then, 10 ml of second step neutralizing solution, Dulcia Neutraliser, were poured on the still rolled hair samples. Neutralization was allowed to proceed for 10 minutes. The hair samples were then removed from the supporting rod and massaged by hand for about 1 minute. Hair samples were then rinsed with water, shampooed once with Shea natural keratin shampoo and dried.

The permed hair samples displayed a stable curling/waving of the fibers supporting the suitability for hair colored according to the present teachings to undergo further hair styling as conventionally performed.

Example 15: Hair Appearance

Hair coated according to the present teachings were generally soft to the touch, displayed a shiny healthy appearance, as well in some instances as a volume improvement, as assessed by trained observers. The volume improvement was assessed against an uncoated reference and is believed to be due to the mild increase in hair diameter as a result of the thin amino-silicone film formed thereon. A film having a thickness of about 0.3-1.0 μm increases the diameter of the fiber by about 0.6-2.0 μm. Assuming an hair fiber having a diameter of about 50-100 μm, such coats provide for a diameter increase of approximately 0.5-5%.

In addition to satisfactory or even improved appearance, the hair samples coated according to the present disclosure were combable (the coating/coloring resulting in smooth individual fibers) and found to behave in this respect in a manner comparable to uncoated controls. Such findings (even made in control compositions devoid of coloring pigments) are notable, since conventional coloring methods generally tend to reduce the natural shine of the hair and/or are likely to weaken the hair fibers. In order to quantify such observations, hair samples coated/colored according to the present teachings can be subjected to the following assessment.

The coated hair samples are mounted and combed on a cylinder to align hair fibers. Shine can be monitored using a Samba hair system, Bossa Nova Technologies, USA, the measurements being collected using a polarized incident light for the identification between specular and diffused light on the cylinder mount on which samples are disposed. The shine parameter is the first reflection that carries the same polarization of the incident light. For each hair sample, including an uncoated control of the same hair type, gloss measurements are taken in at least three different areas of the tuft and averaged. Results are provided in Arbitrary Units (AU) of shine. For reference, changes in 1 AU or less are generally not detectable to the naked eye, while changes in 2 AU or less are considered tolerable for most colors. Advantageously the shine of hair fibers coated according to the present teachings will be stable as long as the coating is not removed from the fibers. The available qualitative results suggest that the present coloring method does not harm the hair fibers, and may even improve their volume.

Example 16: Hair Robustness

While conventional coloring methods, especially when a permanent effect is sought, generally damage the hair fiber and are likely to weaken it, reducing its mechanical resilience, hair samples coated according to the present teachings are believed to be at least as resistant as uncoated counterparts. The robustness of the hair was assessed as follows.

The hair samples were coated as described for sample BC of Example 3. Uncoated hair served as control. For each sample, individual hair fibers were tested in an LR X Plus test machine of Ametek Lloyd Instruments to assess the force applied at break point, the fiber being subjected to a load of 20 Newton at a load speed of 1 mm/min. The diameter of each tested fiber was measured using a handheld micrometer. The Force at Break Point (in N) was normalized to the diameter (in mm), and the results of 6 fibers were averaged. The normalized force at breakpoint of native uncoated hair fibers was found to be on average 14.78 with a standard deviation of 2.57. The normalized force at breakpoint of hair fibers coated according to the present teachings was found to be on average 14.20 with a standard deviation of 3.35. As can be seen from these results, coated and uncoated samples displayed similar behavior as far as resistance to tension and breakpoint force is concerned. This supports that the compositions according to the present teachings do not impair the mechanical properties of the hair, a damage frequently observed when coloration is performed by conventional dye methodology.

Example 17: Amino-Silicone Compositions Including a Reactive Filler

While in previous examples the cross linkers of the condensation-curable amino-silicone pre-polymers were typically miscible therewith and sometimes even amino-silicone reactants (e.g., amino-silane monomers), in the present study alternative compositions were prepared in which the cross-linkers (i.e., the three-dimensional (3D) network former) of the amino-silicone film included hydrophobic fumed silica, typically surface after treated. The surface treatment of the amorphous fumed silica, when known, consisted of one or more of silicone oils, poly siloxanes, hexamethyl disilazane (HMDS, as available for example under CAS No. 68909-20-6) and amino silanes. The particles of reactive fumed silica were provided either in dry form or in dispersions, the below amounts referring to the solid contents of the materials. The particles tested differed in their surface treatment and/or in their size (as estimated by their specific surface area). The particles tested had a specific surface area (as assessed by BET and reported by their respective manufacturers) between about 25 $m^2/g$ and about 245 $m^2/g$. All fillers were selected to have a refractive index identical or similar (±10%) to the refractive index of the amino-silicone matrix. Even in powder form the fumed silica may be provided with a residual water content of up to 2.5 wt. %.

The overall specific external and internal surface area of porous solids, such as fumed silica, can be determined by measuring the amount of physically adsorbed gas according to the Brunauer, Emmett and Teller (BET) method. In one embodiment, the surface area is determined according to ISO 9277.

In a vial, were mixed for about 5 seconds using a Vortex Genie 2 mixer (from Scientific Industries Inc., USA) the following series of formulations containing reactive hydrophobic fumed silica in the reactive oil phase:

First Series 0.012 g of condensation-curable amino-silicone pre-polymer, GP-397 (having an Amine Number of 116 and a MW ~3,754 g/mol) supplied by Genesee Polymers Corp., USA.
0.048 g of amino-functional silane reactive monomer, Dynasylan® SIVO 210 including a combination of three condensation-curable monomers each having MW between about 221 g/mol and about 425 g/mol, supplied by Evonik Industries AG, Germany, and serving herein as cross-linker.
0.02 g of an hydrophobic fumed silica (30 wt. % of the combined weight of the afore-listed amino-silicone pre-polymers) selected from Aerosil® R 8200, Aerosil® NA 50 H, Aerosil® R 812 S, and Aerosil® NA 50 Y, supplied by Evonik Resource Efficiency GmbH, 3650 and NanoBYK 3652, supplied by BYK USA Inc.

Second Series 0.04 g of condensation-curable amino-silicone pre-polymer, KF-857 (having an Amine Number of 127), supplied by Shin Etsu.
0.16 g of amino-functional silane cross-linker, Dynasylan® SIVO 210 (Evonik) or of (1-(3-triethoxysily)propyl)-2,2-diethoxy-1-aza-2-silacyclopentane (such as commercialized by Gelest as SIT8187.2).
0.006 g of condensation-curable amino-silicone pre-polymer being a slow cure amine/alkoxy end-blocked silicone, GP-145 (having an Amine Number of 11 and a MW of 18,000) by Genesee.
0.004 g, 0.006 g, 0.008 g or 0.012 g of Aerosil® R 8200 (corresponding to 10 wt. %, 15 wt. %, 20 wt. % or 30 wt. % by weight of KF-857).

Third Series

In a third series, a colored sample was prepared by adding 5 wt. % of Carbon Black nano-powder (Colour Black FW 182, Orion Engineered Carbons, CAS No. 1333-86-4) pre-milled with BYK LPX 21879 at a 1:1 weight ratio, to a blend of the second series including 0.04 g of KF-857, 0.16 g of Dynasylan® SIVO 210, 0.006 g of GP-145 and 0.031 g of Aerosil® R 8200.

The resulting curable amino-silicone blends (colored or uncolored ASBs) were further sonicated for 15 seconds at 30% of maximal amplitude of a Q700 sonicator (QSonica LLC, USA) until they formed a clear solution.

In a separate vessel, a 0.1 wt. % emulsifier dispersion was prepared by adding 0.06 g of polyoxyethylene (20) sorbitan monooleate surfactant (Tween® 80, CAS No. 9005-65-6, supplied by Sigma-Aldrich Co., USA) to 59.94 g of deionized water. The mix was manually shaken until a clear and homogeneous surfactant solution was obtained.

Unless otherwise stated, each Amino-Silicone Emulsion (ASE) was prepared by adding the total weight of each ASB clear blend into 60 g of the 0.1 wt. % surfactant solution and by sonicating the mixture for 15 seconds at 50% of maximal amplitude of a Q700 sonicator, until a homogeneous emulsion was obtained (all having a pH of about 10). The average size ($D_v50$) of the resulting emulsion droplets was measured using a laser diffraction particle size analyzer (Mastersizer AWA 2003 from Malvern Instruments Ltd., United Kingdom) and was found to be sub-micronic for all tested emulsions.

The zeta potential of the emulsion prepared with the ASB of the second series, wherein Aerosil® R 8200 was included at 10 wt. % by weight of KF-857, was measured as detailed in Example 12 and found to be of +6 mV. The same oil phase blend, prior to its emulsification, was analyzed by DSC as well as by a rheometer, as detailed in Example 12. No glass transition temperature could be detected, and the average viscosity was found to be 9.7 mPa·s, demonstrating low viscosity of the oil phase.

Hair samples were dipped in the various ASEs prepared with each of the afore-described hydrophobic fumed silica and rinsed as previously detailed. All samples provided for the formation of amino-silicone films which coated the hair fibers at least as well as their counterpart compositions devoid of fumed silica. Among the hydrophobic fumed silica samples tested, Aerosil® R 8200, surface treated with HMDS, was found particularly suitable.

The addition of a reactive filler in the reactive oil phase of compositions according to the present teachings, such as exemplified by the above-mentioned hydrophobic fumed silica, is expected to accelerate the curing of the amino-silicone film following its application on the hair fibers. In the event such materials are used as in the condensation-curable amino-silicones of the present coating compositions, then in a kit such reactive fillers will be preferably supplied in a compartment separate from the reactive amino-silicone pre-polymers.

Example 18: Desolubilizing Pre-Treatment of Coating Materials

While in previous examples, the amino-silicone pre-polymers used for the preparation of the condensation-curable amino-silicone coating compositions were preferably inherently water-insoluble (enabling the formation of an emulsion), the present study demonstrated that water-soluble pre-polymers (their solubility optionally resulting from hydrolysis), can also be used. However, the resulting relatively weak coloration prompted the inventors to prefer first rendering such relatively soluble materials less soluble or insoluble ahead of emulsification and application.

The "desolubilization" or "insolubilization" step was performed by mixing 20 wt. % of a water soluble aminopropyltriethoxysilane (APTES; CAS No. 919-30-2) (Dynasylan® AMEO from Evonik), with 70 wt. % of a water insoluble non-amine functionalized silane, methyltrimethoxysilane (MTMS; CAS No. 1185-55-3, purchased from Sigma Aldrich) and 10 wt. % distilled water, the constituents being added to a vial in the listed order. After a brief stirring by Vortex, the mixture was left to react in the open vial for two hours at ambient temperature. During such time, MTMS is expected to react with APTES forming condensation bonds therewith, so as to render APTES less water soluble. Following the reaction, the blend including the at least "desolubilized" material is mixed with hexamethyldisoxane (M2) in a w/w ratio of 2:1, and the two are stirred for about 5 sec at ambient temperature. 0.2 g of the resulting product (forming an ASB) was added to 60 g of distilled water and manually shaken for about 10 seconds. The resulting ASE was used to coat hair fibers as previously described. Briefly, hair tufts were dipped in this ASE, washed with tap water to remove excess, then dried using a hair dryer. The method provided coating of the fibers which was prolonged as compared to an amino-silicone film prepared with native APTES (detailed in Example 19).

Example 19: Preparation of Amino-Silicone Emulsions Lacking Reactive Amino-Silicone Polymers While in previous examples, the amino-silicone emulsions included an amino-silicone condensation-curable polymer, optionally in combination with condensation-curable amino-silicone monomers or oligomers, in the present example the amino-silicone film is achieved in absence of amino-silicone reactive polymers.

Exemplary formulations are provided in Table 16 where the amounts of the compounds are provided in grams. As the purpose of the present study was to establish suitability of various types of condensation-curable amino-silicone pre-polymers for the preparation of compositions able to coat hair fibers, the following compositions were devoid of pigment particles. Similar compositions including pigments were previously detailed.

In the table, M2 stands for hexamethyldisiloxane, a silicone oil having a MW of 162.38 and a RI of ~1.377 provided under CAS No. 107-46-0 by Gelest, and DMDES stands for diethoxydimethyl silane (a slow curing condensation-curable monomer having two silanol forming groups per molecule, a MW of 148.28 and an RI of ~1.381) provided under CAS No. 78-62-6 by Sigma-Aldrich.

TABLE 16

| Compound | ASE (NP) 1 | ASE (NP) 2 | ASE (NP) 3 | ASE (NP) 4 | ASE (NP) 5 | ASE (NP) 6 |
|---|---|---|---|---|---|---|
| Dynasylan ® SIVO 210 | 2.0 | 1.8 | 1.6 | 1.6 | | |
| Dynasylan ® 1146 | | | | | 2.0 | |
| Dynasylan ® AMEO | | | | | | 1.0 |
| Gelest SIO6629.1 | | 0.2 | | | | |
| Gelest DMS-S12 | | | | 0.4 | | |
| DMDES | | | 0.4 | | | |
| M2 | 8.0 | 8.0 | 8.0 | 8.0 | 8.0 | |
| Deionized Water | 10.0 | 10.0 | 10.0 | 10.0 | 10.0 | 10.0* |

*The deionized water included 50 wt. % water acidified to pH 4 with acetic acid.

In a vial, were mixed for about 5 seconds using a Vortex Genie 2 mixer (from Scientific Industries Inc., USA) all the materials listed for each ASE in the amounts reported in the table. The cross-linkable amino-silicone mixtures were then emulsified by sonication for 15 seconds at 50% of maximal amplitude of a Q700 sonicator, until a homogeneous emulsion was obtained in absence of added dedicated emulsifier. It should be noted that despite its denomination, ASE(NP)6 prepared using a relatively water-soluble pre-polymer, did not yield an emulsion. The average size ($D_v50$) of the resulting emulsion droplets of ASE(NP)1-5 was measured using a laser diffraction particle size analyzer (Mastersizer AWA 2003 from Malvern Instruments Ltd., United Kingdom) and was found to be in the low micronic range of about 1-2 µm.

As Dynasylan® SIVO 210 (having an estimated Amine Number of 370) contains, according to its supplier, a combination of reactive monomers individually commercially available as Dynasylan® AMEO from Evonik, SIB1824.5 and SIT8187.2 from Gelest, formulations similar to ASE (NP)1 wherein the 2 g of Dynasylan® SIVO 210 was replaced by 2 g of each of its constituent molecules were also prepared.

Dynasylan® 1146, used for the preparation of ASE(NP)5, is a condensation-curable oligomer having an Amine Number of 455 and more than three silanol-forming groups per molecule, purchased from Evonik. SIO6629.1, used for the preparation of ASE(NP)2, is a non-amino hydrophobic condensation-curable monomer having two silanol forming groups per molecule, a MW of ~359 and a RI of 1.443, supplied by Gelest under CAS No. 70851-50-2. DMS-S12, used for the preparation of ASE(NP)4, is a non-amino hydrophobic condensation-curable oligomer having a MW in the range of ~400-700 and a RI of ~1.401, supplied by Gelest under CAS No. 70131-67-8.

Hair samples were dipped in the ASEs prepared with each of the afore-described condensation-curable pre-polymers, excluding amino-silicone reactive polymers, and rinsed as previously detailed. All samples provided for the formation of amino-silicone films which coated the hair fibers at least as well as the formulations of Example 1 additionally comprising an amino-silicone reactive polymer. However the resulting films generally displayed a more brittle behavior. The ASE(NP)2 formulation displayed the best behavior amongst the presently tested series, providing for an acceptable feel to the touch. From the comparison of the results obtained with ASE(NP)1 formulation including Dynasylan® SIVO 210 and the comparative formulations each including one of the three molecules of the blend, it appeared that all constituents similarly provided a good initial adhesion to the hair fibers. However, the formulation consisting of relatively water-soluble Dynasylan® AMEO as the sole reactive amino-silicone pre-polymer, (see also ASE(NP)6) was later found to provide only transient coloration when used in combination with a pigment. Such lack of suitable coloration when using water soluble materials is expected, as water-soluble materials, in particular low MW monomers or oligomers, cannot sufficiently coat the pigment particles to form a layer of suitable optical density.

Water-solubility of a chemical compound, and, for instance, water insolubility of condensation-curable amino-silicone pre-polymers, can be provided by the supplier. It can also be confirmed or determined as follows. Water-solubility was assessed by mixing 1 wt. % of the material in near neutral (~pH7) distilled water at RT, followed by a brief vortex for homogeneity. A clear solution indicated a water-soluble material, whereas turbidity indicated an at least partly water-insoluble material. By this method, Dynasylan® AMEO was confirmed to be soluble, while SIB1824.5 and SIT8187.2 (as well as parent Dynasylan® SIVO 210) were found to be insoluble.

Reactive condensation-curable amino-silicone pre-polymers (KF-857, GP-145) and amino-silicone oils (GP-965, GP-967) were similarly tested and yielded a turbid dispersion at 1 wt. % in water. For comparison, reactive silanes having, as Dynasylan® AMEO (MW 221), a relatively low molecular weight, namely 3-aminopropyldimethylethoxysilane (MW 161) and N-(2-aminoethyl)-3-aminopropyltriethoxysilane (MW 264) were found water soluble, forming clear solutions at 1 wt. %, by same method.

Example 20: Preparation of Comparative Aqueous Compositions or Emulsions

In the present example, the reactive condensation-curable amino-silicone pre-polymers were replaced by related materials. While the purpose of the comparative compositions prepared therefrom is to isolate a particular parameter providing or not satisfactory coloration (or any other desired outcome), it can be readily appreciated that this approach may fail to address complex requirements of combination of parameters.

It should be noted, that as incorporating pigments into a reactive phase can be a complicated process, in particular with silicones, in the following series of comparative examples the pigment was introduced in the aqueous phase to provide a readily detectable marker. Pigment Blue 15:3 (Heliogen Blue K7090, BASF) was size reduced with a dispersant (Metolat® 392, Munzing Chemie) as above described, at a pigment: dispersant w/w ratio of 70:30. The dispersed pigment was added to distilled water, so that the pigment constituted 5 wt. % of the aqueous carrier, resulting in "blue water". 0.2 g of tested comparative material were dissolved or dispersed in 60 ml blue water, including 5 wt. % of pigment. The resulting comparative compositions were mixed to homogeneity by vortex and readily used for coloring tests.

White Yak hair tufts were dipped for one minute in the comparative samples, with gentle stirring, then rinsed with tap water at ambient temperature and dried with a hair dryer. Coloration, if any, was visually assessed and feel was assessed by touch.

The results are presented in the following table. Solubility was tested as detailed above. No coloration relates to the fact that while dipping the hair in the comparative compositions may have transiently tinted the hair with a blue wet coat, such color readily washed-off when the hair samples were rinsed and dried.

TABLE 17

| Comparative Material | Material Type | Coloration | Feel |
|---|---|---|---|
| None | NR | None | NR |
| 3-Aminopropylmethyl-diethoxysilane | Reactive amino silane (soluble) | None | NR |
| N-(2-aminoethyl)-3-aminopropyl triethoxysilane | Reactive amino silane (soluble) | None | NR |
| Bis[methyldiethoxysilyl-propyl] amine | Reactive amino silane (non soluble) | None | NR |
| Decamethylcyclopenta-siloxane | Non-reactive non-amino siloxane (soluble) | None | NR |

TABLE 17-continued

| Comparative Material | Material Type | Color-ation | Feel |
|---|---|---|---|
| DC Q2-7406 (MQ resin and dimethiconol gum) | Non-reactive non-amino siloxane (non soluble) | Hetero-geneously colored | Sticky lump of hair |
| Silicone Fluid 500,000 Cs | Non-reactive non-amino siloxane (non soluble) | Hetero-geneously colored | Sticky lump of hair |

A few observations can be made in connection with the Table 17. Apparently water-soluble materials, even if reactive amino-silanes prospectively capable of condensation curing, cannot properly wet or remain on the hair fibers to enable detectable film formation. The water-insolubility of a material is, however, insufficient to provide for an acceptable coloration. Some of the non-reactive non-amino siloxane tested provided a non-uniform coloring which resisted the unique water rinsing step of the experimental setup. But the silicone resins (supplied as cross-linked materials) failed to provide even such heterogeneous coats in an individual manner, the hair fibers being stuck one to another following "coloration" with these materials. Such coloration detached fairly easily from the hair fibers, rubbing off by contact with fingers even after a week following coloration.

Example 21: Additional Amino-Silicone Emulsions

In the present example, five amino-silicone blends were prepared by mixing condensation-curable amino-silicone monomers (Dynasylan® Sivo 210, SIB1824.5 or SIT8187.2) or oligomers (Silquest® VX-225 or Silquest® Y-15744, Momentive Performance Materials), each of these pre-polymers being present at 73 wt. % of the respective total blend, with amino-silicone oils (GP-967 and GP-965, respectively at 20 wt. % and 7 wt. % of the total blend). 0.2 g of each of the reactive oil phase blend were added to 60 ml of distilled water. Hair samples were coated with the pigment-less ASEs as herein described and all five provided for a non-sticky coat. As explained, pigment-less coats may serve to improve hair volume.

In the description and claims of the present disclosure, each of the verbs, "comprise" "include" and "have", and conjugates thereof, are used to indicate that the object or objects of the verb are not necessarily a complete listing of members, components, elements, steps or parts of the subject or subjects of the verb.

As used herein, the singular form "a", "an" and "the" include plural references and mean "at least one" or "one or more" unless the context clearly dictates otherwise.

Unless otherwise stated, the use of the expression "and/or" between the last two members of a list of options for selection indicates that a selection of one or more of the listed options is appropriate and may be made.

In the discussion, unless otherwise stated, adjectives such as "substantially" and "about" that modify a condition or relationship characteristic of a feature or features of an embodiment of the present technology, are to be understood to mean that the condition or characteristic is defined to within tolerances that are acceptable for operation of the embodiment for an application for which it is intended, or within variations expected from the measurement being performed and/or from the measuring instrument being used. Furthermore, unless otherwise stated, the terms used in this disclosure should be construed as having tolerances which may depart from the precise meaning of the relevant term but would enable the present disclosure or the relevant portion thereof to operate and function as described, and as understood by a person skilled in the art.

When the term "about" precedes a numerical value, it is intended to indicate +/−10%, or +/−5%, or +/−1%, and in all instances is meant to include the precise value.

While this disclosure has been described in terms of certain embodiments and generally associated methods, alterations and permutations of the embodiments and methods will be apparent to those skilled in the art. The present disclosure is to be understood as not limited by the specific embodiments described herein.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method of coating mammalian hair, the method comprising:
    (a) applying, on an external surface of individual hairs of the mammalian hair, an oil-in-water emulsion comprising:
    (A) an aqueous phase comprising water; and
    (B) an oil phase comprising a pre-polymer that, subsequent to condensation curing, forms an elastomer;
    wherein:
    (i) the pre-polymer is aminopropyltriethoxysilane and present in within said oil phase in an amount of from about 15% to about 95% by weight of said oil phase, and
    (ii) said oil phase further comprises a non-amino cross-linking agent to cure said pre-polymer, wherein said non-amino cross-linking agent is methyltrimethoxysilane wherein a total concentration of said non-amino cross-linking agent within said oil phase is at most about 35% by weight;
    (b) after partial condensation curing of said pre-polymer has occurred so as to form an at least partially cured film on the external surface of the individual hairs, washing the hair with a rinsing liquid to remove any excess of said oil-in-water emulsion.

2. A method according to claim 1 said oil-in-water emulsion further comprising an organic solvent, wherein a total concentration of organic solvent within said oil phase, on a weight basis, is at most about 10%.

3. A method according to claim 1, said oil-in-water emulsion further comprising a solid, hydrophobic reactive inorganic filler, said reactive inorganic filler disposed within said oil phase, said filler adapted to facilitate curing of said reactive inorganic aminopropyltriethoxysilane.

4. A method according to claim 3, wherein said reactive inorganic filler comprises a hydrophobic fumed silica.

5. A method according to claim 1, wherein said washing of hair is performed within about 30 minutes after said applying of oil-in-water emulsion has been completed.

6. A method according to claim 1, further comprising, within at least two days of said washing of hair, treating the hair with a hair formulation comprising a cationic surfactant.

7. A method according to claim 1, wherein the prepolymer is a liquid at 25° C.

8. A method according to claim 1 said oil-in-water emulsion further comprising an amino-silicone oil, wherein a total concentration of amino-silicone oil within said oil phase, by weight, is at most about 40%.

9. A method according to claim 1 said oil-in-water emulsion further comprising a non-amino-silicone oil, wherein a total concentration of non-amino-silicone oil within said oil phase, by weight, is at most about 15%.

10. A method according to claim 1, wherein the mammalian hair to which said oil-in-water emulsion is applied is dry or non-wetted mammalian hair, or pre-dyed hair.

11. A method according to claim 1, wherein the mammalian hair to which said oil-in-water emulsion is applied is at least one of unpre-degreased, unpre-shampooed, and unpre-bleached.

12. A method according to claim 1, said oil phase further comprising a pigment.

\* \* \* \* \*